(12) United States Patent
Bai et al.

(10) Patent No.: US 7,422,884 B2
(45) Date of Patent: Sep. 9, 2008

(54) FEEDBACK-RESISTANT MEVALONATE KINASES

(75) Inventors: Renyuan Bai, Baltimore, MD (US); Markus Huembelin, Basel (CH); Martin Lehmann, Grenzach-Wyhlen (DE); Rual Lopez-Ulibarri, Sisseln (CH); Markus Wyss, Liestal (CH)

(73) Assignee: DSM IP Assetts B.V., Heerlen (NL)

( * ) Notice: Subject to any disclaimer, the term of this patent is extended or adjusted under 35 U.S.C. 154(b) by 92 days.

(21) Appl. No.: 10/560,726

(22) PCT Filed: Jun. 10, 2004

(86) PCT No.: PCT/CH2004/000353

§ 371 (c)(1),
(2), (4) Date: Dec. 8, 2005

(87) PCT Pub. No.: WO2004/111214

PCT Pub. Date: Dec. 23, 2004

(65) Prior Publication Data

US 2007/0141685 A1  Jun. 21, 2007

(30) Foreign Application Priority Data

Jun. 12, 2003  (EP) .................... 03012294

(51) Int. Cl.
| | |
|---|---|
| C12N 9/12 | (2006.01) |
| C12N 15/63 | (2006.01) |
| C12N 1/20 | (2006.01) |
| C12N 1/15 | (2006.01) |
| C07H 21/04 | (2006.01) |
| C12P 21/00 | (2006.01) |
| C12P 21/06 | (2006.01) |

(52) U.S. Cl. ............... 435/194; 536/23.2; 536/23.1; 435/71.1; 435/320.1; 435/252.3; 435/252.33; 435/254.2; 435/68.1

(58) Field of Classification Search ............ None
See application file for complete search history.

(56) References Cited

U.S. PATENT DOCUMENTS 6,284,506 B1  9/2001  Hoshino et al.

FOREIGN PATENT DOCUMENTS

WO  WO 02/099095 A2  12/2002

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
S.M. Houten et al., "Biochemical and genetic aspects of mevalonate kinase and its deficiency," *Biochimica et Biophysica Acta*, vol. 1529, No. 1-3, pp. 19-32 (2000).
M. Hümbelin et al., "Genetics of isoprenoid biosynthesis in Paracoccus zeaxanthinifaciens," *Gene*, vol. 297, No. 1-2, pp. 129-139 (2002).

* cited by examiner

*Primary Examiner*—Sheridan Swope
(74) *Attorney, Agent, or Firm*—Bryan Cave LLP

(57) ABSTRACT

The present invention relates to modified mevalonate kinases that are less sensitive to feedback inhibition, and to polynucleotides encoding them. The invention further pertains to vectors comprising these polynucleotides and host cells containing such vectors. The invention provides a method for producing the modified enzyme and a method for producing isoprenoid compounds.

18 Claims, 4 Drawing Sheets

Figure 2:
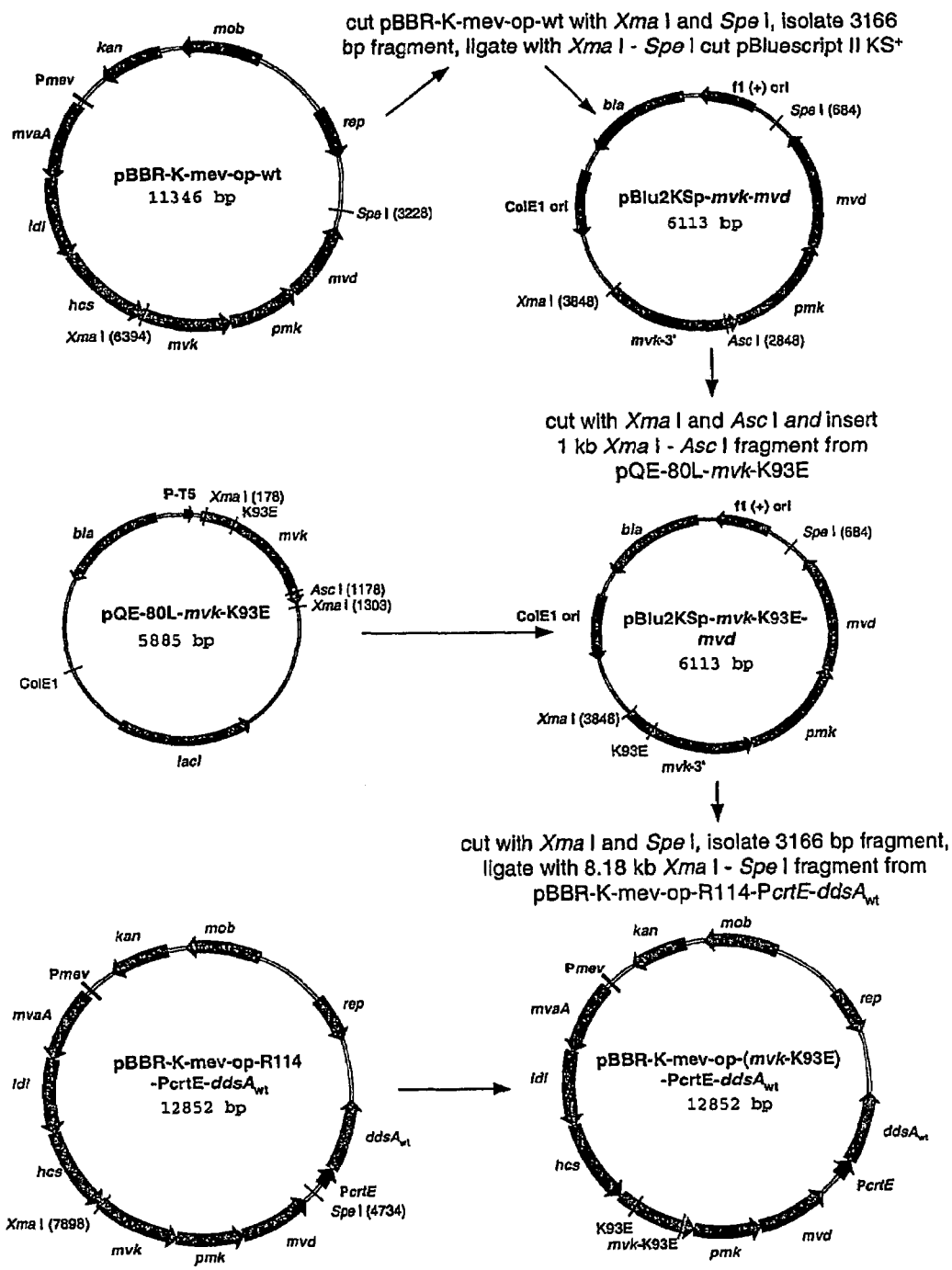

Figure 1.

```
Name: SW_ROD_KIME_MOUSE    oo  Len: 468  Check: 7988  Weight: 1.00
Name: SW_ROD_KIME_RAT      oo  Len: 468  Check: 7364  Weight: 1.00
Name: SW_HUM_KIME_HUMAN    oo  Len: 468  Check: 8275  Weight: 1.00
Name: SW_OTHER_KIME_PYRAB  oo  Len: 468  Check: 8911  Weight: 1.00
Name: SW_OTHER_KIME_PYRHO  oo  Len: 468  Check:  673  Weight: 1.00
Name: SW_OTHER_KIME_PYRFU  oo  Len: 468  Check: 8129  Weight: 1.00
Name: SW_OTHER_KIME_ARATH  oo  Len: 468  Check: 9149  Weight: 1.00
Name: SW_OTHER_KIME_METTH  oo  Len: 468· Check: 6345  Weight: 1.00
Name: SW_OTHER_KIME_ARCFU  oo  Len: 468  Check: 5101  Weight: 1.00
Name: SW_OTHER_KIME_AERPE  oo  Len: 468  Check: 3583  Weight: 1.00
Name: SW_OTHER_KIME_SCHPO  oo  Len: 468  Check: 9129  Weight: 1.00
Name: SW_OTHER_KIME_YEAST  oo  Len: 468  Check: 1853  Weight: 1.00
Name: SW_OTHER_KIME_METJA  oo  Len: 468  Check: 8449  Weight: 1.00
Name: PARACOCCUS           oo  Len: 468  Check: 7087  Weight: 1.00

//

SW_ROD_KIME_MOUSE     ..MLSEALLV SAPGKVILHG EHAVVHGKVA LAAALN.LRT FLLLRP....
SW_ROD_KIME_RAT       ..MLSEVLLV SAPGKVILHG EHAVVHGKVA LAVALN.LRT FLVLRP....
SW_HUM_KIME_HUMAN     ..MLSEVLLV SAPGKVILHG EHAVVHGKVA LAVSLN.LRT FLRLQP....
SW_OTHER_KIME_PYRAB   ...MPRLVLA SAPAKIILFG EHSVVYGKPA IASAID.LRT YVRAEF....
SW_OTHER_KIME_PYRHO   ...MVKYVLA SAPAKVILFG EHSVVYGKPA IASAIE.LRT YVRAQF....
SW_OTHER_KIME_PYRFU   .....MKVIA SAPAKVILFG EHSVVYGKPA IAAAID.LRT FVEAEL....
SW_OTHER_KIME_ARATH   .....MEVKA RAPGKIILAG EHAVVHGSTA VAAAID.LYT YVTLRFPLPS
SW_OTHER_KIME_METTH   ......MKSSA SAPAKAILFG EHAVVYSKPA IAAAID.RRV TVTVSE....
SW_OTHER_KIME_ARCFU   ........MIA SAPGKIILFG EHAVVYGRHA VVSAIN.LRC RVSVRK....
SW_OTHER_KIME_AERPE   ...MRRAARA SAPGKVIIVG EHFVVRGSLA IVAAIG.RRL RVTVRS....
SW_OTHER_KIME_SCHPO   ...MSKSLIV SSPGKTILFG EHAVVGATA LAAAVS.LRS YCKLQT....
SW_OTHER_KIME_YEAST   ...MSLPFLT SAPGKVIIFG EHSAVYNKPA VAASVSALRT YLLISE....
SW_OTHER_KIME_METJA   .......MII ETPSKVILFG EHAVVYGYRA ISMAID.LTS TIEIKETQ..
PARACOCCUS            MSTGRPEAGA HAPGKLILSG EHSVLYGAPA LAMAIA.RYT EVWFTP....
Numbering             1                                                   45

SW_ROD_KIME_MOUSE     .QSNGKVSVN LPNIGIKQVW DVGML...QR LDTSFLEQGD VSVPTLE.QL
SW_ROD_KIME_RAT       .QSNGKVSLN LPNVGIKQVW DVATL...QL LDTGFLEQGD VPAPTLE.QL
SW_HUM_KIME_HUMAN     .HSNGKVDLS LPNIGIKRAW DVARL...QS LDTSFLEQGD VTTPTSE.QV
SW_OTHER_KIME_PYRAB   .NDSGNIKIE AHDIKTP... ........G  LIVSFSED.. .KIYFET.DY
SW_OTHER_KIME_PYRHO   .NDSGNIKIE AHDIKTP... ........G  LIVSFSED.. .KIYFET.DY
SW_OTHER_KIME_PYRFU   .IREKKIRIE AHDIKVP... ........G  LTVSFSEN.. .EIYFET.DY
SW_OTHER_KIME_ARATH   AENNDRLTLQ LKDISLEFSW SLARIKEAIP YDSSTLCR... .STPASC.SE
SW_OTHER_KIME_METTH   ...SSSTHVT IPSLGIR... ........H  SSER...... ..........
SW_OTHER_KIME_ARCFU   ....SDRFLI RSSLGES... ........G  LDYQ...... ..........
SW_OTHER_KIME_AERPE   ..GGKGIVLE SSMLGRHS.. ........AP LPGQ...... ..........
SW_OTHER_KIME_SCHPO   .TNNNEIVIV MSDIGTERRW N......LQS LPWQHVTVEN VQHPASSPNL
SW_OTHER_KIME_YEAST   SSAPDTIELD FPDISFNHKW SINDFNAITE DQVNSQKLAK AQQATDGLSQ
SW_OTHER_KIME_METJA   ...EDEIILN LNDLNKS... ........LG LNLNEIKN.. .INPN...NF
PARACOCCUS            LGIGEGIRTT FANLSGGATY S.......LK LLSGFKSRLD RRFEQFLNGD
Numbering             46                                                  88

SW_ROD_KIME_MOUSE     EKLKKMGDLP RD.RAGNEGM ALLA...FLY LYLAICRKQR TLPSLDMVVW
SW_ROD_KIME_RAT       EKLKKVAGLP RD.CVGNEGL SLLA...FLY LYLAICRKQR TLPSLDIMVW
SW_HUM_KIME_HUMAN     EKLKEVAGLP DD.CAVTERL AVLA...FLY LYLSICRKQR ALPSLDIVVW
SW_OTHER_KIME_PYRAB   GKAAEVLSYV R......... ..HA...IEL VLEEADKR.. ..TGVSVSIT
SW_OTHER_KIME_PYRHO   GKAAEVLSYV R......... ..YA...IEL ALEEESDKR.. ..VGIDVSIT
SW_OTHER_KIME_PYRFU   GKAAEVLSYV R......... ..EA...INL VLEEADKKN. ..VGIKVSIT
SW_OTHER_KIME_ARATH   ETLKSIAVLV EEQNLPKEKM WLSS...GIS TFLWLYTRII GFNPATVVIN
SW_OTHER_KIME_METTH   P.SGGILDYI G......... ...R...CLE LYHDAS.... ..PLDIRVE
SW_OTHER_KIME_ARCFU   R.HPYVVQAV K......... .......... RFGELRN... .IPGAEIEIE
SW_OTHER_KIME_AERPE   GAAAKVSPVL EP........ .......YIA VLRSLAARGY SVVPHTILVE
SW_OTHER_KIME_SCHPO   DLLQGLGELL KNEENGLIHS AMLC...TLY LFTSLSSPS. .QGCTLTIS
SW_OTHER_KIME_YEAST   BLVSLLDPLL AQLSESFHYH AAFC...FLY MFVCLCPHA. ..KNIKFSLK
SW_OTHER_KIME_METJA   GDFKYCLCAI KN........ ........TL DYLNIEPK.. ..TGFKINIS
PARACOCCUS            LKVHKVLTHP DDLAVYALAS LLHDKPPGTA AMPGIGAMHH LPRPGELGSR
Numbering             89                                                 138
```

Figure 1 (continued)

```
SW_ROD_KIME_MOUSE     SELPPGAGLG SSAAYSVCLA AALLTACEEV SNPLKDGVSV SRWPEEDLKS
SW_ROD_KIME_RAT       SELPPGAGLG SSAAYSVCVA AALLTACEEV TNPLKDRGSI GSWPEEDLKS
SW_HUM_KIME_HUMAN     SELPPGAGLG SSAAYSVCLA AALLTVCEEI PNPLKDGDCV NRWTKEDLEL
SW_OTHER_KIME_PYRAB   SQIPVGAGLG SSAAVAVATI GAVSKLLDLE LS........ ...KEE....
SW_OTHER_KIME_PYRHO   SQIPVGAGLG SSAAVAVATI GAVSRLLGLE LS........ ...KEE....
SW_OTHER_KIME_PYRFU   SQIPVGAGLG SSAAVAVATI GAVSKLLGLE LS........ ...KEE....
SW_OTHER_KIME_ARATH   SELPYGSGLG SSAALCVALT AALLASSISE KTR...GNGW SSLDETNLEL
SW_OTHER_KIME_METTH   MEIPAGSGLG SSAALTVALI GALDRYHGRD HG........ ...PGE....
SW_OTHER_KIME_ARCFU   SEIPIGSGLG SSAAVIVATI AALNAEFDGD MD........ ...KEA....
SW_OTHER_KIME_AERPE   SGIPPRAGLG SSAASMVAYA LSYSAMHGDP IS........ ...AED....
SW_OTHER_KIME_SCHPO   SQVPLGAGLG SSATISVVVA TSLLLAFGNI EPP...SSN. SLQNNKALAL
SW_OTHER_KIME_YEAST   STLPIGAGLG SSASISVSLA LAMAYLGGLI GS.....NDL EKLSENDKHI
SW_OTHER_KIME_METJA   SKIPISCGLG SSASITIGTI KAVSGFYNKE LK........ ...DDE....
PARACOCCUS            TELPIGAGMG SSAAIVAATT VLFETLLDRP KT........ ...PEQ....
Numbering             139                                                173
```

```
SW_ROD_KIME_MOUSE      INKWAFEGER VIHGNPSGVD NAVSTWGGAL RFQ....QGT ..MSSLKSLP
SW_ROD_KIME_RAT        INKWAYEGER VIHGNPSGVD NSVSTWGGAL RYQ....QGK ..MSSLKRLP
SW_HUM_KIME_HUMAN      INKWAFQGER MIHGNPSGVD NAVSTWGGAL RYH....QGK ..ISSLKRSP
SW_OTHER_KIME_PYRAB    IAKMGHKVEL LVQGASSGID PTVSAIGGFL YYK....QGE ..PEHLP.PV
SW_OTHER_KIME_PYRHO    IAKLGHKVEL LVQGASSGID PTVSAVGGFL YYK....QGK ..PEPLP.FM
SW_OTHER_KIME_PYRFU    IAKMGHKTEL LVQGASSGID PTVSAIGGFI FYE....KGK ..FEHLP.FM
SW_OTHER_KIME_ARATH    LNKWAFEGEK IIHGKPSGID NTVSAYGNMI KFC....SGE ..ITRLQSNM
SW_OTHER_KIME_METTH    TAARAHRVEV DVQGAASPLD TAISTYGGLV YLDS...QRR ..VRQFE.AD
SW_OTHER_KIME_ARCFU    IFQMAKQVEI DVQGRASGID PFISTFGGSW LFP....ERR ..KVEMP...
SW_OTHER_KIME_AERPE    LYSVAMEGEK IAHGKPSGVD VTIAVRGGVL AYR....RGE NPVDIRPGLT
SW_OTHER_KIME_METTH    IEAWSFLGEC CIHGTPSGID NAVATNGGLI AFR....KAT AHQSAMKEFL
SW_OTHER_KIME_YEAST    VNQWAFIGEK CIHGTPSGID NAVATYGNAL LPEKDSHNGT INTNNFKFLD
SW_OTHER_KIME_METJA    IAKLGYMVEK EIQGKASITD TSTITYKGIL EIKNN..KFR KIKGEFEEFL
PARACOCCUS             RFDRVRFCER LKHGKAGPID AASVVRGGLV RVGGNG.PGS ISSFDLPEDH
Numbering              174                                                 222

SW_ROD_KIME_MOUSE      ....SLQILL TNTKV.PRST KALVAAVRSR L.TKFPEIVA PLLTSIDAIS
SW_ROD_KIME_RAT        ....ALQILL TNTKV.PRST KALVAGVRSR L.IKFPEIMA PLLTSIDAIS
SW_HUM_KIME_HUMAN      ....ALQILL TNTKV.PRNT RALVAGVRNR L.LKFPEIVA PLLTSIDAIS
SW_OTHER_KIME_PYRAB    ....ELPIVV GYTGS.SGST KELVAMVRRR Y.EEMPELIE PILESMGKLV
SW_OTHER_KIME_PYRHO    ....ELPIVV GYTGS.TGST KELVAMVRKR Y.EEMPELVE PILEAMGKLV
SW_OTHER_KIME_PYRFU    ....ELPIVV GYTGS.SGPT KELVAMVRKR Y.EEMPELIV PILEAMGKVV
SW_OTHER_KIME_ARATH    ....PLRMLI TNTRV.GRNT KALVSGVSQR A.VRHPDAMK SVFNAVDSIS
SW_OTHER_KIME_METTH    ....LGDLVI AHLDY.SGET ARMVAGVAER F.RRFPDIMG RIMDTVESIT
SW_OTHER_KIME_ARCFU    .....FKFPV INFG..SRST AEMVAKVAEL R.ERHPEVVD KIFDAIDAIS
SW_OTHER_KIME_AERPE    ....GVTLLV ADTGV.ERRT RDVVEHVLSI A.DALGEAST YIYRAADLIA
SW_OTHER_KIME_SCHPO    KPKDTLSVMI TDTKQ.PKST KKLVQGVFEL K.ERLPTVID SIIDAIDGIS
SW_OTHER_KIME_YEAST    DFP.AIPMIL TYTRI.PRST KDLVARVRVL VTEKFPEVMK PILDAMGECA
SW_OTHER_KIME_METJA    K...NCKPLI VYAEKRKKKT AELVNEVAKI E......NKD EIFKEIDKVI
PARACOCCUS             DLVAGRGWYW VLHGRPVSGT GECVSAVAAA H...G..RDA ALWDAFAVCT
Numbering              223                                                 267

SW_ROD_KIME_MOUSE      LECERVLGEM VAAP...... ...VPEQYLV LEELIDMNQH HLNALGVGHN
SW_ROD_KIME_RAT        LECERVLGEM AAAP...... ...VPEQYLV LEELMDMNQH HLNALGVGHA
SW_HUM_KIME_HUMAN      LECERVLGEM GEAP...... ...APEQYLV LEELIDMNQH HLNALGVGHA
SW_OTHER_KIME_PYRAB    DKAKEVIISK LDE....... ....EEKFLK LGELMNINHG LLDALGVSTK
SW_OTHER_KIME_PYRHO    DKAKEIILSK LDE....... ....EEKLTK LGELMNINHG LLDALGVSTK
SW_OTHER_KIME_PYRFU    EKAKDVILSN VDK....... ....EEKFER LGVLMNINHG LLDALGVSTK
SW_OTHER_KIME_ARATH    KELAAIIQSK DETS...... ...VTEKEER IKELMEMNQG LLLSMGVSHS
SW_OTHER_KIME_METTH    NTAYRELLRN NTEP...... .......... LGELMNLNQG LLDSMGVSTR
SW_OTHER_KIME_ARCFU    LEASDVG..S AER....... .......... LEELIAINQS LLRAIGVSNP
SW_OTHER_KIME_AERPE    REALHAIE.K GDA....... .......ER LGLIMNAAQG LLSSLGASSL
SW_OTHER_KIME_SCHPO    KSAVLALTSE SDK....... ....NSSAKK LGEFIVLNQK LLECLGVSHY
SW_OTHER_KIME_YEAST    LQGLEIMTKL SKCKGTDDEA VETNNELYEQ LLELIRINHG LLVSIGVSHP
SW_OTHER_KIME_METJA    DEALKIK..N KED....... .......... FGKLMTKNHE LLKKLNISTP
PARACOCCUS             RALEAALLSG GSP....... .......... .DAAITENQR LLERIGVVPA
Numbering              268                                                 299
```

Figure 1 (continued)

```
SW_ROD_KIME_MOUSE      SLDQLCQVTA AHG.LHSKLT GAG.....GG GCGITLLKPG LEQATVEAAK
SW_ROD_KIME_RAT        SLDQLCQVTA AHG.LHSKLT GAG.....GG GCGITLLKPG LERAKVEAAK
SW_HUM_KIME_HUMAN      SLDQLCQVTR ARG.LHSKLT GAG.....GG GCGITLLKPG LEQPEVEATK
SW_OTHER_KIME_PYRAB    KLSELVYAAR TAGAIGAKLT GAG.....GG GC.MYALAPG KQRE....VA
SW_OTHER_KIME_PYRHO    KLGELVYAAR TAGAIGAKLT GAG.....GG GC.MYALAPG RQRE....VA
SW_OTHER_KIME_PYRFU    KLSELVYAAR VAGALGAKIT GAG.....GG GC.MYALAPN KQRE....VA
SW_OTHER_KIME_ARATH    SIEAVILTTV KHK.LVSKLT GAG.....GG GCVLTLLPTG TVVDK....VV
SW_OTHER_KIME_METTH    ELSMMVYEAR NAGAAGSKIT GAG.....GG GS.IIAHCPG CVDD....VV
SW_OTHER_KIME_ARCFU    EIDRTIAELE RMG.LHSKLT GAG.....GG GC.IFGLFKG EKPK......
SW_OTHER_KIME_AERPE    EIETLVYRMR SAGALGAKLT GAG.....WG GCVIGLFKEG EVERG....LE
SW_OTHER_KIME_SCHPO    SIDRVLQATK SIG..WTKLT GAG.....GG GCTITLLTPE CKEEEFKLCK
SW_OTHER_KIME_YEAST    GLELIKNLSD DLRIGSTKLT GAG.....GG GCSLTLLRRD ITQEQIDSFK
SW_OTHER_KIME_METJA    KLDRIVDIGN RFG.FGAKLT GAG.....GG GCVIILVNEE KEKE......
PARACOCCUS             ATQALVAQIE EAG.GAAKIC GAGSVRGDHG GAVLVRIDDA QAMASVMARH
Numbering              300                                                 348

SW_ROD_KIME_MOUSE      QALTSCG.FD CWETSIGAPG VSTHSAAAVG DPVRQAL.GL ..........
SW_ROD_KIME_RAT        QALTGCG.FD CWETSIGAPG VSMHSATSIE DPVRQAL.GL ..........
SW_HUM_KIME_HUMAN      QALTSCG.FD CLETSIGAPG VSIHSATSLD SRVQQALDGL ..........
SW_OTHER_KIME_PYRAB    TAIKIAG.GT PMITRISKEG LRIEEVRE.. .......... ..........
SW_OTHER_KIME_PYRHO    TAIKIAG.GI PMITRVSREG LRIEEVSR.. .......... ..........
SW_OTHER_KIME_PYRFU    TAIRIAG.GT PMITEISREG LKIEEVIK.. .......... ..........
SW_OTHER_KIME_ARATH    EELESSG.PQ CFTALIGGNG AQICY..... .......... ..........
SW_OTHER_KIME_METTH    TALNRN..WK AMRAEFSVKG LI........ .......... ..........
SW_OTHER_KIME_ARCFU    ........G SFIVEPEKEG VRIEE..... .......... ..........
SW_OTHER_KIME_AERPE    SVVESSS..Q APTASIAEEG ARLEEF.... .......... ..........
SW_OTHER_KIME_SCHPO    ESLLAHK.NS IYDVQLGGPG VSVVTDSDSF FPQYESDFDF KKLNLLSKFN
SW_OTHER_KIME_YEAST    KKLQDDFSYE TFETDLGGTG CCLLSAKNLN KDLKIKSLVF QLFENKTTTK
SW_OTHER_KIME_METJA    .......... .LLKELNKED VRIFNCRMMN .......... ..........
PARACOCCUS             PDLDWAPLRM SRTGAAPGPA PRAQPLPGQG .......... ..........
Numbering              349                 378

SW_ROD_KIME_MOUSE      .......... ........
SW_ROD_KIME_RAT        .......... ........
```

```
SW_HUM_KIME_HUMAN       ..........  ........
SW_OTHER_KIME_PYRAB     ..........  ........
SW_OTHER_KIME_PYRHO     ..........  ........
SW_OTHER_KIME_PYRFU     ..........  ........
SW_OTHER_KIME_ARATH     ..........  ........
SW_OTHER_KIME_METTH     ..........  ........
SW_OTHER_KIME_ARCFU     ..........  ........
SW_OTHER_KIME_AERPE     ..........  ........
SW_OTHER_KIME_SCHPO     KYYI......  ........
SW_OTHER_KIME_YEAST     QQIDDLLLPG  NTNLPWTS
SW_OTHER_KIME_METJA     ..........  ........
PARACOCCUS              ..........  ........
```

FEEDBACK-RESISTANT MEVALONATE KINASES

This application is the National Stage of International Application No. PCT/CH2004/000353, filed Jun. 10, 2004.

The present invention provides modified mevalonate kinases that are less sensitive to feedback inhibition. The modified enzymes and polynucleotides encoding the same can be used for the production of isoprenoid compounds, for the treatment of disorders that are characterized by decreased mevalonate kinase activity, and for diagnostic purposes.

Mevalonate kinase (MK) is an essential enzyme in the mevalonate pathway which leads to the production of numerous cellular isoprenoids. Isopentenyl diphosphate (IPP), the product of the mevalonate pathway, and the isomeric compound, dimethylallyl diphosphate (DMAPP), are the fundamental building blocks of isoprenoids in all organisms. The isoprenoids include more than 23,000 naturally occurring molecules of both primary and secondary metabolism. The chemical diversity of this natural product class reflects their wide-ranging physiological roles in all living systems. Isoprenoids include, e.g., hopane triterpenes, ubiquinones and menaquinones in bacteria, carotenoids, plastoquinones, mono-, sesqui-, di-, and tri-terpenes, and the prenyl side chains of chlorophylls in plants, and heme A, quinones, dolichols, sterols/steroids and retinoids in mammals. In addition, isoprenoids are involved in isopentenyl tRNAs, in protein prenylation and in cholesterol modification of, e.g., the hedgehog class of cell signaling proteins.

The MK enzyme has been characterized both at the biochemical and the molecular level in a variety of organisms (Houten et al., Biochim. Biophys. Acta 1529, 19-32, 2000). Already now, the DNA and amino acid sequences of many mevalonate kinases are known (e.g., Swiss-Prot accession numbers/IDs P07277/kime_yeast; Q9R008/kime_mouse; P17256/kime_rat; Q03426/kime_human; P46086/kime_arath; Q09780/kime_schpo; Q9V187/kime_pyrab; O59291/kime_pyrho; Q8U0F3/kime_pyrfu; Q50559/kime_metth; O27995/kime_arcfu; Q58487/kime_metja; Q9Y946/kime_aerpe), and every month, new entries can be added to the list of known mevalonate kinase sequences. The above sequences which have been obtained from genome sequencing projects have been assigned putative mevalonate kinase function based on sequence similarity with known mevalonate kinases. However, for those skilled in the art, it is straightforward to prove that these sequences in fact code for proteins with mevalonate kinase activity.

In terms of regulation, HMG-CoA reductase is considered broadly to be the rate-determining enzyme in the mevalonate pathway (e.g., Goldstein and Brown, Nature 343, 425-430, 1990; Weinberger, Trends Endocrinol. Metab. 7, 1-6, 1996; Hampton et al., Trends Biochem. Sci. 21, 140-145, 1996; Houten et al., J. Biol. Chem. 278, 5736-5743, 2003). In line with this view, supplementation of the culture medium with mevalonate has been shown to stimulate carotenoid production in both *Phaffia rhodozyma* (Calo et al., Biotechnol. Lett. 17, 575-578, 1995) and *Haematococcus pluvialis* (Kobayashi et al., J.

Ferment. Bioeng. 71, 335-339, 1991). Increasing evidence in recent years, however, indicates that mevalonate kinase is subject to feedback inhibition by, e.g., the down-stream products geranyldiphosphate, farnesyldiphosphate and geranylgeranyldiphosphate. This feedback inhibition may also contribute to regulation and rate limitation of the mevalonate pathway and, thus, of isoprenoid biosynthesis in general.

In humans, the importance of mevalonate kinase was demonstrated by the identification of its deficiency as the biochemical and molecular cause of the inherited human disorders mevalonic aciduria and hyperimmunoglobulinemia D and periodic fever syndrome (Houten et al., 2000; Nwokoro et al., Mol. Genet. Metab. 74, 105-119, 2001). The pathophysiology of these disorders is not yet understood, but eventually will give insight into the in vivo role of mevalonate kinase and isoprenoid biosynthesis with respect to the acute phase response and fever. Mevalonate kinase deficiency also seems to be involved, e.g., in Zellweger syndrome and in rhizomelic chondrodysplasia punctata, a disorder of peroxisomal biogenesis wherein a subset of peroxisomal enzymes, including mevalonate kinase, is not transported into peroxisomes (Kelley and Herman, Annu. Rev. Genomics Hum. Genet. 2, 299-341, 2001). Finally, mevalonate kinase was proposed to play a role in cellular proliferation, cell cycle regulation and/or cellular transformation (see Graef et al., Virology 208, 696-703, 1995; Hinson et al., J. Biol. Chem. 272, 26756-26760, 1997).

All mevalonate kinases investigated so far are feedback-inhibited by downstream products of the pathway. No mevalonate kinase has so far been described to be resistant to feedback inhibition by, e.g., farnesyl pyrophosphate or geranylgeranyl pyrophosphate. Feedback-resistant mevalonate kinase enzymes may have industrial potential, e.g., (1) in the biotechnological production of all kinds of isoprenoid compounds (e.g., carotenoids, coenzyme Q10, vitamin D, sterols, etc.), (2) as diagnostic enzymes for, e.g., enzymatic measurement of mevalonate concentrations in biological fluids, or (3) as therapeutic enzymes for lowering mevalonate concentrations in patients with mevalonic aciduria. Feedback-resistant MKs are particularly suited for biotechnological production of isoprenoids, since they may allow a larger flux through the mevalonate pathway and, thus, higher isoprenoid productivity.

As used herein, the term "mevalonate kinase" shall mean any enzyme that is capable of catalyzing the phosphorylation of mevalonate (mevalonic acid) to 5-phosphomevalonate (5-phosphomevalonic acid), or of mevalonate analogues (as, e.g., described by Wilde and Eggerer, Eur. J. Biochem. 221, 463-473, 1994) to the corresponding phosphorylated compounds. To afford phosphorylation of mevalonate (or mevalonate analogues), the enzyme requires additionally a suitable phosphate donor. As phosphate donors for mevalonate kinase, different compounds are conceivable. The most preferred phosphate donor is ATP (adenosine 5'-triphosphate). Other preferred phosphate donors are TTP, ITP, GTP, UTP, or CTP (see Gibson et al., Enzyme 41, 47-55, 1989). A "mevalonate kinase" may be homologous to one or more of the enzymes the amino acid sequences of which are shown in SEQ ID NOs:1 to 14. "Homologous" refers to a mevalonate kinase that is at least about 60% identical, preferably at least about 70% identical, more preferably at least about 80% identical, even more preferably at least about 90% identical, most preferably at least about 95% identical to one or more of the amino acid sequences as shown in SEQ ID NOs:1 to 14 and 30.

The term "% identity", as known in the art, means the degree of relatedness between polypeptide or polynucleotide sequences, as the case may be, as determined by the match between strings of such sequences. "Identity" can be readily determined by known methods, e.g., with the program GAP (GCG Wisconsin Package, version 10.2, Accelrys Inc., 9685 Scranton Road, San Diego, Calif. 92121-3752, USA) using the following parameters: gap creation penalty 8, gap extension penalty 2 (default parameters).

"Wild-type enzyme" or "wild-type mevalonate kinase" shall mean any mevalonate kinase homologous to any one of SEQ ID Nos:1-14 and 30 that is used as starting point for designing (more) feedback resistant mutants according to the present invention. Inherently, this definition implies that such a "wild-type enzyme" or "wild-type mevalonate kinase" is sensitive to inhibition to physiologically or industrially relevant concentrations of a downstream product of the mevalonate pathway, e.g., FPP or GGPP. "Wild-type" in the context of the present invention shall not restrict the scope of the invention to only mevalonate kinases/mevalonate kinase sequences only derivable from nature. It shall be explicitly stated here that also variants of synthetic mevalonate kinases (as long as they are homologous to any one of SEQ ID Nos:1-14 and 30) are termed "wild-type", if they can be made (more) feedback resistant by any of the teachings of the present invention. The terms "wild-type mevalonate kinase" and "non-modified mevalonate kinase" are used interchangeably herein.

A "mutant", "mutant enzyme", or "mutant mevalonate kinase" shall mean any variant derivable from a given wild-type enzyme/mevalonate kinase (according to the above definition) according to the teachings of the present invention and being (more) feedback resistant than the respective wild-type enzyme. For the scope of the present invention, it is not relevant how the mutant(s) are obtained; such mutants can be obtained, e.g., by site-directed mutagenesis, saturation mutagenesis, random mutagenesis/directed evolution, chemical or UV mutagenesis of entire cells/organisms, etc. These mutants can also be prepared, e.g., by designing synthetic genes, and/or by in vitro (cell-free) translation (see, e.g., Jermutus et al., Curr. Opin. Biotechnol. 9, 534-548, 1998; Betton, Curr. Prot. Pept. Sci. 4, 73-80, 2003; Martin et al., Biotechniques 31, 948-, 2001). For testing of feedback resistance, mutants can be generated by methods known to those skilled in the art (e.g. by site-directed mutagenesis or by designing synthetic genes).

"Isoprenoid" in the context of this patent application shall include any and all metabolite(s) and prenylated macromolecule(s) derivable from mevalonate by either natural or non-natural pathways (i.e., pathways not occurring in nature, but engineered biotechnologically), preferably biochemical pathways. Isoprenoids include but are not limited to hopane triterpenes, ubiquinones and menaquinones in bacteria, carotenoids, plastoquinones, mono-, sesqui-, di-, and tri-terpenes, and the prenyl side chains of chlorophylls in plants, and heme A, quinones, coenzyme Q10, dolichols, sterols/steroids, vitamin D, retinoids, and the like.

It is in general an object of the present invention to provide a mevalonate kinase which has been modified in a way that its catalytic properties are more favorable (i.e., less sensitive to feedback inhibition) than those of the non-modified mevalonate kinase.

The invention relates to a modified mevalonate kinase which exhibits a sensitivity to feedback inhibition which is reduced in comparison to the corresponding non-modified mevalonate kinase wherein
(i) the amino acid sequence of the modified mevalonate kinase contains at least one mutation when compared with the amino acid sequence of the corresponding non-modified mevalonate kinase and
(ii) the at least one mutation is at one or more amino acid positions selected from the group consisting of amino acid positions corresponding to positions 17, 47, 93, 94, 132, 167, 169, 204, and 266 of the amino acid sequence of *Paracoccus zeaxanthinifaciens* mevalonate kinase as shown in SEQ ID NO:1.

As used herein, the term "feedback inhibition" denotes the inhibition of enzymatic activity of mevalonate kinase by a metabolite downstream of mevalonate in isoprenoid biosynthesis. Metabolites downstream of mevalonate in isoprenoid biosynthesis include but are not limited to 5-phosphomevalonate, isopentenyl diphosphate (IPP), 3,3-dimethylallyl diphosphate (DMAPP), geranyl diphosphate (GPP), farnesyl diphosphate (FPP), geranylgeranyl diphosphate (GGPP), farnesol, dolichol phosphate, and phytyl-pyrophosphate (Dorsey and Porter, J. Biol. Chem. 243, 4667-4670, 1968; Flint, Biochem. J. 120, 145-150, 1970; Gray and Kekwick, Biochim. Biophys. Acta 279, 290-296, 1972; Hinson et al., J. Lipid Res. 38, 2216-2223, 1997). It is believed that feedback inhibition of mevalonate kinase is based on allosteric regulation of mevalonate kinase by binding to the enzyme of the metabolite downstream of mevalonate in isoprenoid biosynthesis.

Preferably, the feedback inhibition is feedback inhibition by farnesyl diphosphate (FPP) or geranylgeranyl diphosphate (GGPP).

According to the present invention the modified mevalonate kinase exhibits a sensitivity to feedback inhibition which is reduced in comparison to the corresponding non-modified mevalonate kinase. Preferably, the sensitivity to feedback inhibition of the modified mevalonate kinase of the invention is reduced by at least 5% in comparison to the corresponding non-modified mevalonate kinase (for measurement and quantification of feedback resistance, see below).

"Feedback resistance" shall mean any increase in resistance to "feedback inhibition" (as defined above). Feedback resistance can be analyzed in different ways known to those skilled in the art. An appropriate approach shall be described here shortly: mevalonate kinase activity is measured in an activity assay similar to the one described in Example 2 at non-saturating concentrations of ATP (or of another phosphate donor) and mevalonate (or mevalonate analogue), i.e., at ATP (or phosphate donor) and mevalonate (or mevalonate analogue) concentrations around which the reaction rate is sensitive to changes of these substrate concentrations, e.g. at concentrations around the respective $K_m$ values of the enzyme under investigation for these substrates. The activities of both wild-type mevalonate kinase and of a variant/mutant of this enzyme are measured under otherwise identical conditions both in the absence and presence of a relevant concentration of a feedback inhibitor, i.e., at a concentration of feedback inhibitor affording significant inhibition of the wild-type mevalonate kinase. If the extent of inhibition (e.g., % inhibition) by the feedback inhibitor is lower for the mutant than for the wild-type enzyme, then the mutant is "feedback resistant" in the context of the present patent application. Once a "feedback resistant" variant/mutant has been identified, the same procedure as described above can be applied to identify further improved mutants, i.e., mutants that are even more feedback resistant. Feedback resistance (%) is calculated as follows: if a and b are the measured mevalonate kinase activities of the wild-type enzyme in the absence and presence, respectively, of the feedback inhibitor (e.g., FPP), and if c and d are the measured mevalonate kinase activities of the mutant enzyme in the absence and presence, respectively, of the same feedback inhibitor, then % feedback resistance is:

$$\% \text{ resistance} = 100 \cdot ((d/c) - (b/a))/(1 - (b/a))$$

Preferably, the feedback resistance refers to the experimental conditions described in Example 2 of this application. Approximately 3-30 mU/ml (corresponding to approx. 1-10 µg/ml of *Paracoccus zeaxanthinifaciens* mevalonate kinase), preferably approx. 10-20 mU/ml of mevalonate kinase activity, and optionally 46 µM FPP were present in the assay mixture, and the reaction was carried out at 30° C.

The modified mevalonate kinase of the invention exhibits a feedback resistance of at least 5%, preferably at least about 10%, more preferably at least about 25%, even more preferably at least about 40%, still more preferably at least about 60%, most preferably at least about 70% when compared with the corresponding non-modified mevalonate kinase.

The amino acid sequence of the modified mevalonate kinase of the invention contains at least one mutation when compared with the amino acid sequence of the corresponding non-modified mevalonate kinase. The mutation may be an addition, deletion and/or substitution. Preferably, the mutation is an amino acid substitution wherein a given amino acid present in the amino acid sequence of the non-modified mevalonate kinase is replaced with a different amino acid in the amino acid sequence of the modified mevalonate kinase of the invention. The amino acid sequence of the modified mevalonate kinase may contain at least one amino acid substitution when compared with the amino acid sequence of the corresponding non-modified mevalonate kinase. In further embodiments, the modified mevalonate kinase contains at least two, at least three, at least four or at least five substitutions when compared with the amino acid sequence of the corresponding non-modified mevalonate kinase. In other embodiments of the invention, the modified mevalonate kinase contains one to ten, one to seven, one to five, one to four, two to ten, two to seven, two to five, two to four, three to ten, three to seven, three to five or three to four amino acid substitutions when compared with the amino acid sequence of the corresponding non-modified mevalonate kinase.

The one or more mutation(s) may be at one or more amino acid position(s) selected from the group consisting of amino acid positions corresponding to positions 17, 47, 93, 94, 132, 167, 169, 204, and 266 of the amino acid sequence of *Paracoccus zeaxanthinifaciens* mevalonate kinase as shown in SEQ ID NO:1.

Preferably, the at least one mutation is at one or more amino acid positions selected from the group consisting of amino acid positions corresponding to positions 17, 47, 93, 94, 132, 167, and 266 of the amino acid sequence of *Paracoccus zeaxanthinifaciens* mevalonate kinase as shown in SEQ ID NO:1. In another preferred embodiment the at least one mutation is at one or more amino acid positions selected from the group consisting of amino acid positions corresponding to positions 17, 47, 93, 94, 132, 167, and 169 of the amino acid sequence of *Paracoccus zeaxanthinifaciens* mevalonate kinase as shown in SEQ ID NO:1.

If the modified mevalonate kinase contains only a single amino acid substitution when compared to the corresponding non-modified mevalonate kinase it is preferred that the single amino acid substitution is at a position selected from the group consisting of positions corresponding to the amino acid positions 17, 47, 93, 94, 204 and 266 of SEQ ID N O:1. More preferably, the substitution is I17T, G47D, K93E, V94I, R204H or C266S.

In a particularly preferred embodiment, the mutation is a substitution which affects the amino acid position corresponding to amino acid position 17 of the amino acid sequence as shown in SEQ ID NO:1. The amino acid present in the non-modified mevalonate kinase is preferably isoleucine. The amino acid in the sequence of the non-modified mevalonate kinase may be changed to either threonine or alanine. Most preferably, the substitution at the amino acid position corresponding to position 17 of the sequence as shown in SEQ ID NO:1 consists of the replacement of isoleucine with threonine.

If the modified mevalonate kinase contains at least two mutations when compared to the corresponding non-modified mevalonate kinase, one of the mutations may be at the amino acid position corresponding to position 375 of SEQ ID NO:1. If the modified mevalonate kinase contains two amino acid substitutions when compared to the corresponding non-modified mevalonate kinase it is preferred that the amino acid substitutions are at positions corresponding to combinations of positions 132/375, 167/169, 17/47 or 17/93 of SEQ ID NO:1. Most preferred are the combinations P132A/P375R, R167W/K169Q, I17T/G47D or I17T/K93E.

If the modified mevalonate kinase contains three amino acid substitutions when compared to the corresponding non-modified mevalonate kinase it is preferred that the amino acid substitutions are at positions corresponding to combinations of positions 17/167/169, 17/132/375, 93/132/375, or 17/47/93 of SEQ ID NO:1. Most preferred are the combinations I17T/R167W/K169Q, I17T/P132A/P375R, K93E/P132A/P375R, I17T/R167W/K169H, I17T/R167T/K169M, I17T/R167T/K169Y, I17T/R167F/K169Q, I17T/R167T/K169N, I17T/R167H/K169Y, I17T/G47D/K93E or I17T/G47D/K93Q.

If the modified mevalonate kinase contains four amino acid substitutions when compared to the corresponding non-modified mevalonate kinase it is preferred that the amino acid substitutions are at positions corresponding to combinations of positions 17/47/93/132 of SEQ ID NO:1. Most preferred are the combinations I17T/G47D/K93E/P132A or I17T/G47D/K93E/P132S.

Most preferred are the combinations of mutations disclosed in Table 1, 2, 3 or 4 (see infra). The amino acid positions identified in these examples may be transferred to mevalonate kinases of different origin.

The modified mevalonate kinase of the invention may be obtained by introducing a mutation to the corresponding non-modified mevalonate kinase. A non-modified mevalonate kinase may be any mevalonate kinase which exhibits sensitivity to feedback inhibition. Non-modified mevalonate kinases include but are not limited to mevalonate kinases derivable from nature. Non-modified mevalonate kinases further include mevalonate kinases which are homologous to any one of the amino acid sequences as shown in SEQ ID NOs:1 to 14 and 30.

Preferred non-modified mevalonate kinases include those having a sequence selected from the group consisting of the amino acid sequences as shown in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14 and SEQ ID NO:30.

The non-modified mevalonate kinase may be of eukaryotic or prokaryotic, preferably fungal or bacterial origin, more preferably *Aspergillus* or *Saccharomyces* or *Paracoccus* or *Phaffia* and most preferably *Aspergillus niger* or *Saccharomyces cerevisiae* or *Paracoccus zeaxanthinifaciens* or *Phaffia rhodozyma*, origin. In one embodiment, the non-modified mevalonate kinase is of prokaryotic, preferably bacterial origin, more preferably *Paracoccus* and most preferably *Paracoccus zeaxanthinifaciens* origin.

Preferably, the feedback inhibition of the non-modified mevalonate kinase by FPP is at least 10%, more preferably at least 20%, still more preferably at least 30%, even more preferably at least 40%, most preferably at least 50% as determined in an assay described in Example 2 (0 or 46 µM FPP).

The modified mevalonate kinase of the invention may comprise foreign amino acids, preferably at its N- or C-terminus.

"Foreign amino acids" mean amino acids which are not present in a native (occurring in nature) mevalonate kinase, preferably a stretch of at least about 3, at least about 5 or at least about 7 contiguous amino acids which are not present in a native mevalonate kinase. Preferred stretches of foreign amino acids include but are not limited to "tags" that facilitate purification of the recombinantly produced modified mevalonate kinase. Examples of such tags include but are not limited to a "His$_6$" tag, a FLAG tag, a myc tag, and the like.

In another embodiment the modified mevalonate kinase may contain one or more, e.g. two, deletions when compared with the amino acid sequence of the corresponding non-modified mevalonate kinase. Preferably, the deletions affect N- or C-terminal amino acids of the corresponding non-modified mevalonate kinase and do not significantly reduce the functional properties, e.g., the specific activity, of the enzyme.

The modified mevalonate kinase of the invention usually is a non-naturally occurring mevalonate kinase. Preferably, the specific activity of the modified mevalonate kinase is at least 10%, more preferably at least 20%, still more preferably at least 35%, even more preferably at least 50%, most preferably at least 75% of the specific activity of the corresponding non-modified mevalonate kinase.

The modified mevalonate kinase of the invention may be an isolated polypeptide. As used herein, the term "isolated polypeptide" refers to a polypeptide that is substantially free of other polypeptides. An isolated polypeptide is preferably greater than 80% pure, preferably greater than 90% pure, more preferably greater than 95% pure, most preferably greater than 99% pure. Purity may be determined according to methods known in the art, e.g., by SDS-PAGE and subsequent protein staining. Protein bands can then be quantified by densitometry. Further methods for determining the purity are within the level of ordinary skill.

The invention further relates to a polynucleotide comprising a nucleotide sequence which codes for a modified mevalonate kinase according to the invention. "Polynucleotide" as used herein refers to a polyribonucleotide or polydeoxyribonucleotide that may be unmodified RNA or DNA or modified RNA or DNA. Polynucleotides include but are not limited to single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. The term "polynucleotide" includes DNA or RNA that comprises one or more unusual bases, e.g., inosine, or one or more modified bases, e.g., tritylated bases.

The polynucleotide of the invention can easily be obtained by modifying a polynucleotide sequence which codes for a non-modified mevalonate kinase. Examples of such polynucleotide sequences encoding non-modified mevalonate kinases are shown in SEQ ID NOs:16 to 29 and 31. Methods for introducing mutations, e.g., additions, deletions and/or substitutions into the nucleotide sequence coding for the non-modified mevalonate kinase include but are not limited to site-directed mutagenesis and PCR-based methods.

The principles of the polymerase chain reaction (PCR) method are outlined, e.g., by White et al., Trends Genet. 5, 185-189, 1989, whereas improved methods are described, e.g., in Innis et al. [PCR Protocols: A guide to Methods and Applications, Academic Press, Inc. (1990)].

DNA sequences of the present invention can be constructed starting from genomic or cDNA sequences coding for mevalonate kinases known in the state of the art [for sequence information see, e.g., the relevant sequence databases, for example Genbank (Intelligenetics, California, USA), European Bioinformatics Institute (Hinston Hall, Cambridge, GB), NBRF (Georgetown University, Medical Centre, Washington D.C., USA) and Vecbase (University of Wisconsin, Biotechnology Centre, Madison, Wis., USA) or the sequence information disclosed in the figures and sequence listing] by methods of in vitro mutagenesis [see e.g. Sambrook et al., Molecular Cloning, Cold Spring Harbor Laboratory Press, New York]. A widely used strategy for such "site directed mutagenesis", as originally outlined by Hutchison and Edgell (J. Virol. 8, 181-189, 1971), involves the annealing of a synthetic oligonucleotide carrying the desired nucleotide substitution to a target region of a single-stranded DNA sequence wherein the mutation should be introduced (for review see Smith, Annu. Rev. Genet. 19, 423-462, 1985; and for improved methods see references 2-6 in Stanssen et al., Nucl. Acids Res. 17, 4441-4454, 1989). Another possibility of mutating a given DNA sequence which is also preferred for the practice of the present invention is mutagenesis by using the polymerase chain reaction (PCR). DNA as starting material can be isolated by methods known in the art and described, e.g., in Sambrook et al. (Molecular Cloning) from the respective strains/organisms. It is, however, understood that DNA encoding a mevalonate kinase to be constructed/mutated in accordance with the present invention can also be prepared on the basis of a known DNA sequence, e.g. by construction of a synthetic gene by methods known in the art (as described, e.g., in EP 747 483 and by Lehmann et al., Prot. Eng. 13, 49-57, 2000).

Non-limiting examples of polynucleotides encoding modified mevalonate kinases according to the invention are shown in SEQ ID NO: 32 and 33.

The polynucleotide of the invention may be an isolated polynucleotide. The term "isolated polynucleotide" denotes a polynucleotide that is substantially free from other nucleic acid sequences such as but not limited to other chromosomal and extrachromosomal DNA and RNA. Conventional nucleic acid purification methods known to skilled artisans may be used to obtain isolated polynucleotides. The term also embraces recombinant polynucleotides and chemically synthesized polynucleotides.

In yet another embodiment the invention pertains to a vector or plasmid comprising a polynucleotide according to the invention. The vector or plasmid preferably comprises at least one marker gene. The vector or plasmid may further comprise regulatory elements operably linked to the polynucleotide of the invention. The term "operably linked" as used herein refers to the association of nucleic acid sequences on a single nucleic acid fragment so that the function of one is affected by the other. For example, a promoter is operably linked with a coding sequence when it is capable of affecting the expression of that coding sequence, i.e., the coding sequence is under the transcriptional control of the promoter. Coding sequences can be operably linked to regulatory sequences in sense or antisense orientation. The term "expression" denotes the transcription of a DNA sequence into mRNA and/or the translation of mRNA into an amino acid sequence. The term "overexpression" means the production of a gene product in a modified organism (e.g., modified by transformation or transfection) that exceeds levels of production in the corresponding non-modified organism.

Once complete DNA sequences of the present invention have been obtained they can be integrated into vectors by methods known in the art and described in, e.g., Sambrook et al. (s.a.) to (over-) express the encoded polypeptide in appropriate host systems. However, a man skilled in the art knows that also the DNA sequences themselves can be used to transform the suitable host systems of the invention to get (over-) expression of the encoded polypeptide. Appropriate host systems are for example fungi, like Aspergilli, e.g. *Aspergillus niger* or *Aspergillus oryzae*, or like *Trichoderma*, e.g. *Trichoderma reesei*, or yeasts like *Saccharomyces*, e.g. *Saccharomyces cerevisiae*, or *Pichia*, like *Pichia pastoris*, or *Hansenula polymorpha*, e.g. *H. polymorpha* (DSM5215). A man skilled in the art knows that such microorganisms are available from depository authorities, e.g. the American Type Culture Collection (ATCC), the Centraalbureau voor Schimmelcultures (CBS) or the Deutsche Sammlung für Mikroorganismen und Zellkulturen GmbH (DSMZ) or any other depository authority as listed in the Journal "Industrial Property" (vol. 1, pages 29-40, 1991) or in the Official Journal of the European Patent Office (vol. 4, pages 155/156, 2003).

Bacteria which can be used are, e.g., *Paracoccus*, as e.g. *Paracoccus zeaxanthinifaciens, E. coli*, Bacilli as, e.g., *Bacillis subtilis* or *Streptomyces*, e.g. *Streptomyces lividans* (see e.g. Anné and van Mellaert in FEMS Microbiol. Lett. 114, 121-128, 1993. *E. coli* which could be used are, e.g., *E. coli* K12 strains, e.g. M15 (described as DZ 291 by Villarejo et al. in J. Bacteriol. 120, 466-474, 1974), HB 101 (ATCC No. 33694) or *E. coli* SG13009 (Gottesman et al., J. Bacteriol. 148, 265-273, 1981).

Vectors which can be used for expression in fungi are known in the art and described e.g. in EP 420 358, or by Cullen et al. (Bio/Technology 5, 369-3.76, 1987), Ward (in Molecular Industrial Mycology, Systems and Applications for Filamentous Fungi, Marcel Dekker, New York, 1991), Upshall et al. (Bio/Technology 5, 1301-1304, 1987), Gwynne et al. (Bio/Technology 5, 71-79, 1987), or Punt et al. (J. Biotechnol. 17, 19-34, 1991), and for yeast by Sreekrishna et al. (J. Basic Microbiol. 28, 265-278, 1988; Biochemistry 28, 4117-4125, 1989), Hitzemann et al. (Nature 293, 717-722, 1981) or in EP 183 070, EP 183 071, EP 248 227, EP 263 311. Suitable vectors which can be used for expression in *E. coli* are mentioned, e.g., by Sambrook et al. [s.a.] or by Fiers et al. in Proc. 8th Int. Biotechnol. Symp. [Soc. Franc. de Microbiol., Paris (Durand et al., eds.), pp. 680-697, 1988], Bujard et al. (in Meth. Enzymol., eds. Wu and Grossmann, Academic Press, Inc., Vol. 155, 416-433, 1987), or Stüber et al. (in Immunological Methods, eds. Lefkovits and Pernis, Academic Press, Inc., Vol. IV, 121-152, 1990). Vectors which could be used for expression in Bacilli are known in the art and described, e.g. in EP 207 459 or EP 405 370, by Yansura and Henner in Proc. Natl. Acad. Sci. USA 81, 439-443 (1984), or by Henner, Le Grice and Nagarajan in Meth. Enzymol. 185, 199-228, 1990. Vectors which can be used for expression in *H. polymorpha* are known in the art and described, e.g., in Gellissen et al., Biotechnology 9, 291-295, 1991.

Either such vectors already carry regulatory elements, e.g. promoters, or the DNA sequences of the present invention can be engineered to contain such elements. Suitable promoter elements which can be used are known in the art and are, e.g., for *Trichoderma reesei* the cbh1- (Haarki et al., Biotechnology 7, 596-600, 1989) or the pki1-promoter (Schindler et al., Gene 130, 271-275, 1993), for *Aspergillus oryzae* the amy-promoter [Christensen et al., Abstr. 19th Lunteren Lectures on Molecular Genetics F23 (1987); Christensen et al., Biotechnology 6, 1419-1422, 1988; Tada et al., Mol. Gen. Genet. 229, 301-306, 1991], for *Aspergillus niger* the glaA- (Cullen et al., Bio/Technology 5, 369-376, 1987; Gwynne et al., Bio/Technology 5, 713-719, 1987; Ward in Molecular Industrial Mycology, Systems and Applications for Filamentous Fungi, Marcel Dekker, New York, 83-106, 1991), alcA- (Gwynne et al., Bio/Technology 5, 718-719, 1987), suc1- (Boddy et al., Curr. Genet. 24, 60-66, 1993), aphA- (MacRae et al., Gene 71, 339-348, 1988; MacRae et al., Gene 132, 193-198, 1993), tpiA- (McKnight et al., Cell 46, 143-147, 1986; Upshall et al., Bio/Technology 5, 1301-1304, 1987), gpdA- (Punt et al., Gene 69, 49-57, 1988; Punt et al., J. Biotechnol. 17, 19-37, 1991) and the pkiA-promoter (de Graaff et al., Curr. Genet. 22, 21-27, 1992). Suitable promoter elements which could be used for expression in yeast are known in the art and are, e.g., the pho5-promoter (Vogel et al., Mol. Cell. Biol. 9, 2050-2057, 1989; Rudolf and Hinnen, Proc. Natl. Acad. Sci. USA 84, 1340-1344, 1987) or the gap-promoter for expression in *Saccharomyces cerevisiae*, and e.g. the aox1-promoter for *Pichia pastoris* (Koutz et al., Yeast 5, 167-177, 1989; Sreekrishna et al., J. Basic Microbiol. 28, 265-278, 1988), or the FMD promoter (Hollenberg et al., EPA No. 0299108) or MOX promoter (Ledeboer et al., Nucleic Acids Res. 13, 3063-3082, 1985) for *H. polymorpha*.

Suitable promoters and vectors for bacterial expression include, e.g., a synthetic promoter described by Giacomini et al. (Gene 144, 17-24, 1994). Appropriate teachings for expression of the claimed (mutant) mevalonate kinases in bacteria, either by appropriate plasmids or through integration of mevalonate kinase-encoding DNA sequences into the chromosomal DNA, can be found in many places, e.g., U.S. Pat. No. 6,322,995.

The invention further concerns a host cell comprising the vector or plasmid of the invention. Suitable host cells may be eukaryotic or prokaryotic cells. Examples of suitable host cells include but are not limited to bacterial cells, such as cells of streptococci, staphylococci, enterococci, *E. coli, Streptomyces*, cyanobacteria, *Bacillus subtilis*, and *Streptococcus pneumoniae*; fungal cells, such as cells of a yeast *Kluyveromyces, Saccharomyces*, a basidiomycete, *Candida albicans* and *Aspergillus*; insect cells such as cells of *Drosophila* S2 and *Spodoptera* Sf9; animal cells such as CHO, COS, HeLa, 3T3, BHK, 293, CV-1; and plant cells, such as cells of a gymnosperm or angiosperm.

Accordingly, vectors comprising a polynucleotide of the present invention, preferably for the expression of said polynucleotides in bacterial, fungal, yeast or plant hosts, and such transformed bacteria or fungal, yeast or plant hosts are also an object of the present invention.

The invention further relates to a method for producing an isoprenoid compound comprising:
(a) culturing the host cell of the invention in a suitable medium under conditions that allow expression of the modified mevalonate kinase in the host cell; and
(b) optionally separating the isoprenoid compound from the medium.

Such a method can be used for the biotechnological production of any type of isoprenoid compound or isoprenoid-derived compound: e.g., carotenoids such as, but not limited to, phytoene, lycopene, α-, β- and γ-carotene, lutein, zeaxanthin, β-cryptoxanthin, adonixanthin, echinenone, canthaxanthin, astaxanthin and derivatives thereof (Misawa & Shimada, J. Biotechnol. 59, 169-181, 1998; Miura et al., Appl. Environ. Microbiol. 64, 1226-1229, 1998; Hirschberg, Curr. Opin. Biotechnol. 10, 186-191, 1999; Margalith, Appl. Microbiol. Biotechnol. 51, 431-438, 1999; Schmidt-Dannert, Curr. Opin. Biotechnol. 11, 255-261, 2000; Sandmann, Arch. Biochem. Biophys. 385, 4-12, 2001; Lee & Schmidt-Dannert, Appl. Microbiol. Biotechnol. 60, 1-11, 2002); quinones such as, but not limited to, ubiquinone (=coenzyme Q), menaquinone, plastoquinones and anthraquinones, preferably coenzyme Q6, coenzyme Q7, coenzyme Q8, coenzyme Q9, coenzyme Q10 or coenzyme Q11, most preferably coenzyme Q10 (Clarke, Protoplasma 213, 134-147, 2000;

Han et al., Plant Cell Tissue Organ Culture 67,201-220, 2001; Kawamukai, J. Biosci. Bioeng. 94, 511-517, 2002); rubber and rubber derivatives, preferably natural rubber (=cis-1,4-polyisoprene; Mooibroek & Cornish, Appl. Microbiol. Biotechnol. 53, 355-365, 2000); sterols and sterol derivatives such as, but not limited to, ergosterol, cholesterol, hydrocortisone (Ménard Szczebara et al., Nature Biotechnol. 21, 143-149, 2003), vitamin D, 25-hydroxy-vitamin D3, dietary phytosterols (Ling & Jones, Life Sci. 57, 195-206, 1995) and natural surfactants (Holmberg, Curr. Opin. Colloid. Interface Sci. 6, 148-159, 2001); and a large number of other isoprenoids such as, but not limited to, monoterpenes, diterpenes, sesquiterpenes and triterpenes, e.g., taxol (Jennewein & Croteau, Appl. Microbiol. Biotechnol. 57, 13-19, 2001) and gibberellins (Bruckner & Blechschmidt, Crit. Rev. Biotechnol. 11, 163-192, 1991).

Suitable host cells are all types of organisms that are amenable to genetic modification such as, but not limited to, bacteria, yeasts, fungi, algae, plants or animal cells. Methods of genetic and metabolic engineering are known to the man skilled in the art (e.g., Verpoorte et al., Biotechnol. Lett. 21, 467-479, 1999; Verpoorte et al., Transgenic Res. 9, 323-343, 2000; Barkovich & Liao, Metab. Eng. 3, 27-39, 2001). Similarly, (potentially) suitable purification methods for isoprenoids and isoprenoid-derived compounds and/or molecules are well known in the area of fine chemical biosynthesis and production.

It is understood that a method for biotechnological production of an isoprenoid or isoprenoid-derived compound and/or molecule according to the present invention is not limited to whole-cellular fermentation processes as described above, but may also use, e.g., permeabilized host cells, crude cell extracts, cell extracts clarified from cell remnants by, e.g., centrifugation or filtration, or even reconstituted reaction pathways with isolated enzymes. Also combinations of such processes are in the scope of the present invention.

In the case of cell-free biosynthesis (such as with reconstituted reaction pathways), it is irrelevant whether the isolated enzymes have been prepared by and isolated from a host cell, by in vitro transcription/translation, or by still other means.

The invention further relates to a method for producing a modified mevalonate kinase of the invention comprising:
(a) culturing a host cell of the invention under conditions that allow expression of the modified mevalonate kinase of the invention; and
(b) recovering the modified mevalonate kinase from the cells or from the media.

The modified mevalonate kinases of the invention may be prepared from genetically engineered host cells comprising expression systems.

For recombinant production of the polypeptides of the invention, host cells can be genetically engineered to incorporate polynucleotides or vectors or plasmids of the invention. Introduction of a polynucleotide or vector into the host cell can be effected by methods described in many standard laboratory manuals [e.g., Davis et al., Basic Methods in Molecular Biology (1986), and Sambrook et al., Molecular Cloning: A Laboratory Manual, 2nd Ed., Cold Spring Harbor Laboratory Press, Cold Spring Harbor, N.Y. (1989)] such as calcium phosphate transfection, DEAE-dextran mediated transfection, microinjection, cationic lipid-mediated transfection, electroporation, transduction, ballistic introduction and infection.

A great variety of expression systems can be used to produce the modified mevalonate kinases of the invention. Such vectors include, among others, those described supra. Generally, any system or vector suitable to maintain, propagate or express polynucleotides and/or to express a polypeptide in a host may be used for expression in this regard.

In recombinant expression systems in eukaryotes, for secretion of a translated protein into the lumen of the endoplasmic reticulum, into the periplasmic space or into the extracellular environment appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, and hydroxyapatite chromatography. In one embodiment, high performance liquid chromatography is employed for purification. Well known techniques for protein refolding may be employed to regenerate active conformation when the polypeptide is denatured during isolation and/or purification. Methods of protein purification are described in, e.g., Deutscher, Protein Purification, Academic Press, New York, 1990; and Scopes, Protein Purification, Springer Verlag, Heidelberg, 1994.

Mevalonate kinases of the present invention can be also expressed in plants according to methods as described, e.g., by Pen et al. in Bio/Technology 11, 811-814, 1994 or in EP 449 375, preferably in seeds as described, e.g., in EP 449 376. Some suitable examples of promoters and terminators include those from nopaline synthase (nos), octopine synthase (ocs) and cauliflower mosaic virus (CaMV) genes. One type of efficient plant promoter that may be used is a high level plant promoter. Such promoters, in operable linkage with the genetic sequences of the present invention should be capable of promoting expression of the present gene product. High level plant promoters that may be used in this invention include the promoter of the small subunit (ss) of the ribulose-1,5-bisphosphate carboxylase, for example from soybean (Berry-Lowe et al., J. Mol. Appl. Genet. 1, 483-498, 1982), and the promoter of the chlorophyll a/b binding protein. These two promoters are known to be light-induced in plant cells (see, for example, Genetic Engineering of Plants, an Agricultural Perspective, A. Cashmore, Plenum Press, NY (1983), pages 29-38; Coruzzi et al., J. Biol. Chem. 258,1399-1402, 1983; and Dunsmuir et al., J. Mol. Appl. Genet. 2,285-300, 1983).

Where commercial production of the instant proteins is desired, a variety of culture methodologies may be applied. For example, large-scale production of a specific gene product, overexpressed from a recombinant microbial host may be produced by both batch or continuous culture methodologies. Batch and fed-batch culturing methods are common and well known in the art and examples may be found in Thomas D. Brock in Biotechnology: A Textbook of Industrial Microbiology, Second Edition (1989) Sinauer Associates, Inc., Sunderland, Mass., or Deshpande, Appl. Biochem. Biotechnol. 36, 227-234, 1992. Methods of modulating nutrients and growth factors for continuous culture processes as well as techniques for maximizing the rate of product formation are well known in the art of industrial microbiology and a variety of methods are detailed by Brock, supra.

Fermentation media must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks. It is contemplated that the source of carbon utilized in the present invention may encompass a wide variety of carbon containing substrates and will only be limited by the choice of organism.

The invention further relates to a method for the preparation of a mevalonate kinase having reduced sensitivity to feedback inhibition, comprising the following steps:
(a) providing a polynucleotide encoding a first mevalonate kinase which exhibits sensitivity to feedback inhibition;
(b) introducing one or more mutations into the polynucleotide sequence such that the mutated polynucleotide sequence encodes a second mevalonate kinase which contains at least one amino acid mutation when compared to the first mevalonate kinase wherein the at least one amino acid mutation is at one or more amino acid positions selected from the group consisting of amino acid positions corresponding to positions 17, 47, 93, 94, 132, 167, 169, 204, and 266 of the amino acid sequence as shown in SEQ ID NO:1;
(c) optionally inserting the mutated polynucleotide in a vector or plasmid;
(d) introducing the polynucleotide or the vector or plasmid into a suitable host cell; and
(e) culturing the host cell under conditions that allow expression of the modified mevalonate kinase.

The preferred embodiments of this method correspond to the preferred embodiments of the modified mevalonate kinase, the polynucleotides encoding them, the vectors and plasmids, the host cells, and the methods described herein. The first and second mevalonate kinase correspond to the non-modified and modified mevalonate kinase, respectively (see supra).

Another aspect of the invention is the use of a modified mevalonate kinase of the invention or a polynucleotide of the invention for the manufacture of a medicament for the treatment of a disorder associated with decreased activity of mevalonate kinase. Such disorders include but are not limited to mevalonic aciduria, hyperimmunoglobulinemia D and periodic fever syndrome. It is preferred that a modified mevalonate kinase of the invention is administered as a therapeutic enzyme. The mode of administration includes oral, parenteral, intraperitoneal and/or subcutaneous administration. The modified mevalonate kinases of the invention and salts thereof can be formulated as pharmaceutical compositions (e.g. granules, enzyme crystals, tablets, pills, capsules, injections, solutions, and the like) comprising at least one such enzyme alone or in admixture with pharmaceutically acceptable carriers, excipients and/or diluents. The pharmaceutical compositions can be formulated in accordance with a conventional method. Specific dose levels for any particular patient will be employed depending upon a variety of factors including the activity of specific compounds employed, the age, body weight, general health, sex, diet, time of administration, route of administration, rate of excretion, drug combination, and the severity of the particular disease undergoing therapy.

The polynucleotides of the invention may be used in a gene therapy protocol.

Yet another aspect of the invention is the use of a modified mevalonate kinase of the invention or a polynucleotide of the invention for determining the concentration of mevalonate in biological fluids. Non-limiting examples of biological fluids are blood, serum, plasma, cerebrospinal fluid, urine, tears, sweat, as well as any other intracellular, intercellular and/or extracellular fluids.

It is an object of the present invention to provide a polynucleotide comprising a nucleic acid sequence coding for a modified mevalonate kinase as described above, a vector, preferably an expression vector, comprising such a polynucleotide, a host cell which has been transformed by such a polynucleotide or vector, a process for the preparation of a mevalonate kinase of the present invention wherein the host cell as described before is cultured under suitable culture conditions and the mevalonate kinase is isolated from such host cell or the culture medium by methods known in the art, and a process for the biotechnological production of isoprenoid(s) based on a host cell which has been transformed by such a polynucleotide or vector, and/or which may have stably integrated such a polynucleotide into its chromosome(s).

It is also an object of the present invention to provide (i) a DNA sequence which codes for a mevalonate kinase carrying at least one of the specific mutations of the present invention and which hybridizes under standard conditions with any of the DNA sequences of the specific modified mevalonate kinases of the present invention, or (ii) a DNA sequence which codes for a mevalonate kinase carrying at least one of the specific mutations of the present invention but, because of the degeneracy of the genetic code, does not hybridize but which codes for a polypeptide with exactly the same amino acid sequence as a DNA sequence which hybridizes under standard conditions with any of the DNA sequences of the specific modified mevalonate kinases of the present invention, or (iii) a DNA sequence which is a fragment of such DNA sequences which maintains the activity properties of the polypeptide of which it is a fragment.

"Standard conditions" for hybridization mean in the context the conditions which are generally used by a man skilled in the art to detect specific hybridization signals and which are described, e.g. by Sambrook et al., "Molecular Cloning", second edition, Cold Spring Harbor Laboratory Press 1989, New York, or preferably so-called stringent hybridization and non-stringent washing conditions or more preferably so-called stringent hybridization and stringent washing conditions a man skilled in the art is familiar with and which are described, e.g., in Sambrook et al. (s.a.). A specific example of stringent hybridization conditions is overnight incubation (e.g., 15 hours) at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 µg/ml of denatured, sheared salmon sperm DNA, followed by washing the hybridization support in 0.1×SSC at about 65° C.

It is furthermore an object of the present invention to provide a DNA sequence which can be obtained by the so-called polymerase chain reaction method ("PCR") by PCR primers designed on the basis of the specifically described DNA sequences of the present invention. It is understood that the so obtained DNA sequences code for mevalonate kinases with at least the same mutation as the ones from which they are designed and show comparable activity properties.

The various embodiments of the invention described herein may be cross-combined.

FIG. 1: Multiple sequence alignment calculated with the program ClustalW of mevalonate kinase sequences from mouse (SEQ ID NO: 3), rat (SEQ ID NO: 4), man (SEQ ID NO: 2), yeast (SEQ ID NO: 6), *Arabidopsis thaliana* (ARATH) (SEQ ID NO: 5), *Schizosaccharomyces pombe* (SCHPO) (SEQ ID NO: 7), *Pyrococcus abyssi* (PYRAB) (SEQ ID NO: 8), *Pyrococcus honkoshii* (PYRHO) (SEQ ID NO: 9), *Pyrococcus furiosus* (PYRFU) (SEQ ID NO: 10), *Methanobactenum thermoautotrophicum* (METTH) (SEQ ID NO: 11), *Archaeoglobus fulgidus* (ARCFU) (SEQ ID NO: 12), *Methanococcus jannaschii* (METJA) (SEQ ID NO: 13), *Aeropyrum pemix* (AERPE) (SEQ ID NO: 14), and *Paracoccus zeaxanthinifaciens* (PARACOCCUS) (SEQ ID NO: 1).

Numbering is according to the amino acid sequence of *Paracoccus zeaxanthinifaciens* mevalonate kinase.

FIG. 2: Introduction of the K93E mevalonate kinase mutation into the mevalonate operon on a pBBR-K-based plasmid. See text for details.

The following non-limiting examples further illustrate the invention.

EXAMPLE 1

Multiple Sequence Alignment

A multiple amino acid sequence alignment of different mevalonate kinases (see FIG. 1) can be calculated, e.g., with the program "PILEUP" (GCG Wisconsin Package, version 10.2, Accelrys Inc., 9685 Scranton Road, San Diego, Calif. 92121-3752, USA) using the following parameters: gap creation penalty 12, gap extension penalty 4, and blosum62.cmp matrix (default parameters); or with the program ClustalW (Version 1.7, EMBL, Heidelberg, Germany) using BLOSUM exchange matrix. Such sequence alignments are routinely performed by the man skilled in the art (e.g., Cho et al., J. Biol. Chem. 276, 12573-12578, 2001).

Homologous mevalonate kinases in the context of the present invention may show sequence similarity with any of the mevalonate kinases shown in FIG. 1. FIG. 1 gives an example of a multiple sequence alignment for the mevalonate kinase amino acid sequences of mouse, rat, man, *Arabidopsis thaliana* (ARATH), *Schizosaccharomyces pombe* (SCHPO), yeast (YEAST), *Pyrococcus abyssi* (PYRAB), *Pyrococcus horikoshii* (PYRHO), *Pyrococcus furiosus* (PYRFU), *Methanobacterium thermoautotrophicum* (METTH), *Archaeoglobus fulgidus* (ARCFU), *Methanococcus jannaschii* (METJA), *Aeropyrum pernix* (AERPE), and *Paracoccus zeaxanthinifaciens* (PARACOCCUS) which latter sequence is also used as the reference for amino acid numbering to which the positions of the other sequences, e.g. the ones named before, are referred to. Furthermore the modified rat mevalonate kinase with the E6V mutation means nothing else than the mevalonate kinase of the rat wherein at position 6 according to the assignment as defined above (which is in fact position 4 of the rat mevalonate kinase amino acid sequence), the naturally occurring Glu ("E" refers to the standard IUPAC one letter amino acid code) has been replaced by Val ("V"). All mutants/variants of the present invention are designated in this way.

EXAMPLE 2

Measurement of Mevalonate Kinase Activity and of Inhibition by Feedback Inhibitors Enzymatic assays for measuring mevalonate kinase activity have been described, e.g., by Popák (Meth. Enzymol. 15, 393-, 1969), Gibson et al. (Enzyme 41, 47-55, 1989), Hinson et al. (J. Lipid Res. 38, 2216-2223, 1997), Schulte et al. (Anal. Biochem. 269, 245-254, 1999), or Cho et al. (J. Biol. Chem. 276, 12573-12578, 2001). For preparing mevalonate as substrate, 130 mg of DL-mevalonate lactone (FLUKA Chemie AG, Buchs, Switzerland) were dissolved in 5.5 ml of 0.2 M KOH and incubated for 15 min at 50° C. The solution was then adjusted to pH 7.0 by addition of 0.1 M HCl at room temperature (RT). Except if stated otherwise (see Example 3), the assay mixture consists of 100 mM $K_2HPO_4/KH_2PO_4$ (pH 7.0), 1 mM ATP, 2 mM $MgCl_2$, 1 mM mevalonate, 0.5 mM phosphoenolpyruvate (PEP), 0.32 mM NADH, 20 U/ml pyruvate kinase and 27 U/ml lactate dehydrogenase (Sigma-Aldrich, St. Louis, Mo., USA). FPP, GGPP, IPP, DMAPP and GPP tested as inhibitors in the assay mixtures (at concentrations of 0-100 µM) were all purchased from Sigma. Upon addition of purified ($His_6$-tagged) mevalonate kinase, enzymatic reaction reflected by consumption of NADH was followed by photometric measurement at 340 nm. One unit (1 U) of mevalonate kinase activity catalyzes the phosphorylation of 1 µmol of mevalonate per min.

EXAMPLE 3

Testing of the Quality of the Enzymatic Assay

An optimal assay should fulfill a number of requirements, such as linearity with enzyme concentration and linearity with time. In addition, in the context of the present invention, the assay should allow to quantify inhibition of mevalonate kinase by feedback inhibitors. In the experiments of this Example, the following assay conditions were used: 100 mM $KH_2PO_4$, pH 7.0, 0.125-4 mM ATP, 1.125-5 mM $MgCl_2$ (always 1 mM in excess of ATP!), 0.25-3 mM mevalonate, 0 or 46 µM FPP, 0.16 mM NADH, 0.5 mM PEP, 20 U/ml pyruvate kinase, 27 U/ml lactate dehydrogenase, 30° C. Different amounts of purified $His_6$-tagged *Paracoccus zeaxanthinifaciens* mevalonate kinase were used.

The experiments of this example show that the mevalonate kinase activity assay, in fact, is linear with time and enzyme (mevalonate kinase) concentration, and that under the given conditions for *Paracoccus zeaxanthinifaciens*, MgATP and mevalonate concentrations of 1 mM each may be optimal to allow reliable measurement of feedback inhibition by FPP.

EXAMPLE 4

Mutagenesis of *Paracoccus zeaxanthinifaciens* Mevalonate Kinase to Obtain Feedback-resistant Mutants The cDNA of mevalonate kinase from *Paracoccus zeaxanthinifaciens* R114 is amplified by PCR using a primer encoding an EcoRI restriction site along with a sequence of 6×His as well as a piece of the 5'-end sequence of mevalonate kinase without the ATG start codon, and a primer containing the 3'-end sequence of mevalonate kinase including the stop codon and a BamHI restriction site. After purification by agarose gel electrophoresis, the PCR product is digested by EcoRI and BamHI and ligated into pQE-80L (Qiagen, Hilden, Germany), which is digested with the same enzymes. pQE-80L contains a T5 promoter regulated by a lac operator element, which can be cis-inhibited by the lac repressor also encoded by pQE-80L. The plasmid is then transformed into *E. coli* DH5α of Invitrogen (Carlsbad, Calif., USA) according to the supplier's protocol. Upon addition of 100 µM IPTG at an $OD_{600\,nm}$ of 0.6 during exponential growth phase of *E. coli*, $His_6$-tagged mevalonate kinase is induced at 30° C. for 4 h by shaking at 250 rpm. Purification of $His_6$-tagged mevalonate kinase and of $His_6$-tagged mevalonate kinase mutant enzymes is done with Ni-NTA chromatography using the QIAexpress system/reagents of Qiagen.

Mutagenesis of $His_6$-tagged mevalonate kinase is achieved by the so-called "two step PCR" using Turbo-Pfu DNA polymerase of Stratagene (La Jolla, Calif., USA). The first PCR is performed with a primer containing the mutated codons (primer M) and the primer pQE-5' corresponding to a piece of sequence at the 5'-end of the multiple cloning sites (MCS) of pQE-80L. The template is pQE-80L-His-Mvk. The PCR product is purified by agarose gel electrophoresis and used as a primer for the second PCR reaction also containing the primer pQE-3' encompassing a piece of the 3'-end sequence of the MCS and the wild-type pQE-80L-His-Mvk as template. The PCR product is purified by agarose gel electrophoresis and digested by EcoRI and BamHI, with which the His-Mvk is subcloned in pQE-80L. Finally, the digested fragment is purified by agarose electrophoresis and ligated into pQE-80L linearized by the same restriction enzymes.

EXAMPLE 5

Feedback Resistance of Mutants of *Paracoccus zeaxanthinifaciens* Mevalonate Kinase Mevalonate was prepared as described in Example 2. The assay mixture consists of 100 mM $K_2HPO_4/KH_2PO_4$ (pH 7.0), 1 mM ATP, 1 mM mevalonate, 2 mM $MgCl_2$, 0.5 mM phosphoenolpyruvate (PEP), 0.32 mM NADH, 20 U/ml pyruvate kinase and 27 U/ml lactate dehydrogenase (Sigma-Aldrich, St. Louis, Mo., USA). FPP, GGPP, IPP, DMAPP and GPP tested as inhibitors in the assay mixtures were all purchased from Sigma. 92 µM FPP or 17.6 µM GGPP were used for inhibition assays performed with the mevalonate kinase mutants. For the comparison of inhibition by FPP, GGPP, IPP, DMAPP and GPP, 138 µM of these intermediates were added (Example 9). Upon addition of purified (HiS6-tagged) mevalonate kinase, enzymatic reaction reflected by consumption of NADH was followed by photometric measurement at 340 nm.

Feedback resistance (%) is calculated as follows: if a and b are the measured mevalonate kinase activities of the wild-type enzyme in the absence and presence, respectively, of the feedback inhibitor (in this case, FPP), and if c and d are the measured mevalonate kinase activities of the mutant enzyme in the absence and presence, respectively, of the same feedback inhibitor, then % feedback resistance is:

% resistance=$100 \cdot ((d/c)-(b/a))/(1-(b/a))$

TABLE 1

Impact of mutagenesis of *Paracoccus zeaxanthinifaciens* mevalonate kinase on the specific activity and the feedback resistance of the enzyme.

| Mutant | Specific activity (% of wild-type) | Feedback resistance (%) |
|---|---|---|
| WT | 100 | 0 |
| I17T | 95 | 46 |
| G47D | 121 | 32 |
| K93E | 109 | 33 |
| V94I | 96 | 22 |
| P132A, P375R | 158 | 35 |
| R167W, K169Q | 50 | 43 |
| R204H | 83 | 7 |
| C266S | 64 | 14 |
| I17T, G47D | 77 | 42 |
| I17T, K93E | 72 | 51 |
| I17T, R167W, K169Q | 37 | 71 |
| I17T, P132A, P375R | 62 | 56 |
| K93E, P132A, P375R | 111 | 57 |

WT represents the mevalonate kinase with SEQ ID No: 15 (with $His_6$-tag).

That these mutations have an impact on feedback inhibition of mevalonate kinase is surprising. Previously, a conserved, hydrophobic stretch from residue 133 to residue 156 of human mevalonate kinase has been proposed to be a good candidate for isoprenoid binding (Riou et al., Gene 148, 293-297, 1994; Houten et al., Biochim. Biophys. Acta 1529, 19-32, 2000). However, none of the above mutations is located in the corresponding stretch of *Paracoccus zeaxanthinifaciens* mevalonate kinase (residues 137-160).

A considerable number of mutations have been proposed to decrease or even destroy mevalonate kinase activity and, thus, to cause the human diseases mevalonic aciduria and hyperimmunoglobulinemia D and periodic fever syndrome (e.g., K13X, H20P, H20N, L39P, W62X, S135L, A148T, Y149X, S150L, P165L, P167L, G202R, T209A, R215Q, T243I, L264F, L265P, I268T, S272F, R277C, N301T, G309S, V310M, G326R, A334T, V377I, and R388X; all in human mevalonate kinase; Houten et al., Eur. J. Hum. Genet. 9, 253-259, 2001; Cuisset et al., Eur. J. Hum. Genet. 9,260-266, 2001). Of these, only two (i.e., P165L and R215Q) occur at residues corresponding in position within the amino acid sequence alignment with residues of *Paracoccus zeaxanthinifaciens* mevalonate kinase shown to have an impact on feedback resistance (i.e., residues 169 and 204, respectively). However, the previously described mutations in human mevalonate kinase were not shown to have an effect on feedback resistance, but were rather suggested to negatively impact the (specific) activity of the enzyme.

EXAMPLE 6

Saturated Mutagenesis of *Paracoccus zeaxanthinifaciens* Mevalonate Kinase at Amino Acid Residues/Positions Previously Identified to Have an Impact on the Resistance of the Enzyme to Feedback Inhibition Saturated mutagenesis was done in the same way as described above for mutagenesis, except that the mutagenesis primer was synthesized in a way that the codons subject to saturated mutagenesis were made of randomized sequence.

TABLE 2

Saturated mutagenesis of residues 167 and 169 in the *Paracoccus zeaxanthinifaciens* mevalonate kinase mutant I17T, and impact on specific activity and feedback resistance of the enzyme.

| Mutant | Specific activity (% of wild-type) | Feedback resistance (%) |
|---|---|---|
| WT | 100 | 0 |
| I17T, R167W, K169Q | 37 | 71 |
| I17T, R167W, K169H | 43 | 67 |
| I17T, R167T, K169M | 54 | 57 |
| I17T, R167T, K169Y | 40 | 66 |
| I17T, R167F, K169Q | 43 | 77 |
| I17T, R167I, K169N | 35 | 73 |
| I17T, R167H, K169Y | 54 | 64 |

WT represents the mevalonate kinase with SEQ ID NO: 15 (with $His_6$-tag).

TABLE 3

Saturated mutagenesis of residue 93 in the *Paracoccus zeaxanthinifaciens* mevalonate kinase mutant I17T, G47D.

| Mutant | Specific activity (% of wild-type) | Feedback resistance (%) |
|---|---|---|
| I17T, G47D, K93E | 76 | 78 |
| I17T, G47D, K93Q | 83 | 76 |

TABLE 4

Saturated mutagenesis of residue 132 in the *Paracoccus zeaxanthinifaciens* mevalonate kinase mutant I17T, G47D, K93E.

| Mutant | Specific activity (% of wild-type) | Feedback resistance (%) |
|---|---|---|
| I17T, G47D, K93E | 76 | 78 |
| I17T, G47D, K93E, P132A | 90 | 79 |
| I17T, G47D, K93E, P132S | 100 | 83 |

EXAMPLE 7

Improved Production of the Isoprenoid Compound Coenzyme Q10 Using a Feedback Inhibition-resistant Mevalonate Kinase To test the in vivo effect of mutations affecting feedback inhibition of mevalonate kinase, the *Paracoccus zeaxanthinifaciens* mevalonate kinase mutant K93E was introduced into a functional mevalonate operon cloned in a broad host range vector capable of replicating in *Paracoccus zeaxanthinifaciens*. The production of the isoprenoid compound coenzyme Q10 was compared directly in two recombinant strains of *P. zeaxanthinifaciens* that differ only by the presence or absence of the K93E mutation.

Plasmid Constructions

The plasmid constructions are depicted diagrammatically in FIG. 2. The details of the cloning were as follows. *E. coli* strains were grown at 37° C. in LB medium (Becton Dickinson, Sparks, Md., USA). For maintenance of plasmids in recombinant *E. coli* strains, ampicillin (100 µg/ml) and/or kanamycin (25-50 µg/ml, depending on the experiment) were added to the culture medium. Agar (1.5% final concentration) was added for solid media. Liquid cultures were grown in a rotary shaker at 200 rpm.

Plasmid pBBR-K-mev-op-wt (FIG. 2) contains the mevalonate operon, including its promoter region, from *P. zeaxanthinifaciens* strain ATCC 21588, inserted between the SacI and NsiI sites of plasmid pBBR1MCS-2 (Kovach et al., Gene 166, 175-176, 1995). The cloned mevalonate operon corresponds to the sequence from nucleotides 2469 to 9001 of the sequence having the GenBank/EMBL accession number AJ431696. Between the SacI site and the mevalonate operon sequence there is a short linker sequence, which is derived from plasmid pCR®2.1-TOPO (Invitrogen, Carlsbad, Calif., USA) and corresponds to the sequence from the SacI site to the PCR fragment insertion site. It should be noted that the sequence with accession number AJ431696 is from *P. zeaxanthinifaciens* strain R114 (ATCC PTA-3335), not from *P. zeaxanthinifaciens* strain ATCC 21588. The only difference between the mevalonate operon sequences of the *P. zeaxanthinifaciens* strains ATCC 21588 and R114 is a mutation in the mvk gene from strain R114. This mutation results in a change of amino acid 265 in the mevalonate kinase from alanine to valine (A265V). Because the mevalonate operon in pBBR-K-mev-op-wt is from ATCC 21588, it does not contain the mutation, thus codon 265 in mvk is GCC (and not GTC as in accession number AJ431696).

A plasmid analogous to pBBR-K-mev-op-wt but with the mvk gene from strain R114 was also constructed and was designated pBBR-K-mev-op-R114. Introduction of a ddsA gene from *P. zeaxanthinifaciens* strain ATCC 21588 under the control of the crtE promoter region between the Ecl136 II and the SpeI sites of pBBR-K-mev-op-R114 resulted in pBBR-K-mev-op-R114-PcrtE-ddsA$_{wt}$ (FIG. 2).

The final step was to create a plasmid identical to pBBR-K-mev-op-R114-PcrtE-ddsA$_{wt}$, but containing the K93E mutation in the mvk gene. The plasmid pBlu2SP-mvk-mvd (FIG. 2) was constructed by subcloning the 3166 bp XmaI-SpeI fragment in the XmaI-SpeI cut vector pBluescript II KS+ (Stratagene, La Jolla, Calif., USA). Plasmid pBlu2SP-mvk-mvd has the convenient unique restriction endonuclease sites XmaI and AscI for the introduction of the mutated mvk gene into the 3' end of the mevalonate operon. Plasmid pQE-80L-mvk-K93E was cut with XmaI and AscI and the 1 kb fragment carrying most of mvk, including the K93E mutation, was ligated with the XmaI-AscI cut backbone of pBlu2SP-mvk-mvd resulting in pBlu2KSp-mvk-K93E-mvd. To reconstitute the full-length mevalonate operon with the K93E mutation in mvk, pBlu2KSp-mvk-K93E-mvd was cut with XmaI and SpeI and the 3166 bp fragment ligated with the 8.18 kb XmaI-SpeI fragment from pBBR-K-mev-op-R114-PcrtE-ddsA$_{wt}$, resulting in pBBR-K-mev-op-(mvk-K93E)-PctE-ddsA$_{wt}$. The codon 265 of the mvk gene in this plasmid is GTC, because the mvk gene in pQE-80L-mvk-K93E is derived from *P. zeaxanthinifaciens* strain R114 (ATCC PTA-3335).

In summary, plasmids pBBR-K-mev-op-R14-PcrtE-ddsAwt and pBBR-K-mev-op-(mvk-K93E)-PcrtE-ddsA$_{wt}$ are identical except for the presence of the K93E mutation in the latter plasmid.

Construction of Recombinant *P. zeaxanthinifaciens* Strains

*P. zeaxanthinifaciens* strains were grown at 28° C. The compositions of the media used for *P. zeaxanthinifaciens* are described below. All liquid cultures of *P. zeaxanthinifaciens* grown in flasks were shaken in a rotary shaker at 200 rpm unless specified otherwise. Agar (2% final concentration) was added for solid medium. When media were sterilized by autoclaving, the glucose was added (as a concentrated stock solution) after sterilization to achieve the desired final concentration. F-Medium contains (per liter distilled water): tryptone, 10 g; yeast extract, 10 g; NaCl, 30 g; D-glucose-H$_2$O, 10 g; MgSO$_4$.7H$_2$O, 5 g. The pH is adjusted to 7.0 before sterilization by filtration or autoclaving. Medium 362F/2 contains (per liter distilled water): D-glucose-H$_2$O, 33 g; yeast extract, 10 g; tryptone, 10 g; NaCl, 5 g; MgSO$_4$.7H$_2$O, 2.5 g. The pH of the medium is adjusted to 7.4 before sterilization by filtration or autoclaving. Following sterilization, 2.5 ml each of microelements solution, NKP solution and CaFe solution are added. The latter three solutions are sterilized by filtration. Microelements solution contains (per liter distilled water): (NH$_4$)$_2$Fe(SO$_4$)$_2$.6H$_2$O, 80 g; ZnSO$_4$.7H$_2$O, 6 g; MnSO$_4$.H$_2$O, 2 g; NiSO$_4$.6H$_2$O, 0.2 g; EDTA, 6 g. NKP solution contains (per liter distilled water): K$_2$HPO$_4$, 250 g; (NH$_4$)$_2$PO$_4$, 300 g. CaFe solution contains (per liter distilled water): CaCl$_2$.2H$_2$O, 75 g; FeCl$_3$.6H$_2$O, 5 g; concentrated HCl, 3.75 ml.

Preparation of electrocompetent cells of *P. zeaxanthinifaciens* strain R114 and electroporation was performed as follows: 100 ml F medium was inoculated with 1.5 ml of a stationary phase culture of *P. zeaxanthinifaciens* strain R114 and grown at 28° C., 200 rpm until an optical density at 660 nm of about 0.5 was reached. The cells were harvested by centrifugation for 15 minutes at 4° C., 7000×g and washed twice in 100 ml ice-cold HEPES buffer, pH 7. The final pellet was resuspended in 0.1 ml ice-cold HEPES buffer, pH 7 and the cells were either used immediately for electroporation or glycerol was added to a final concentration of 15% and the cells were stored in 50 µl aliquots at −80° C. One to five µl plasmid DNA was added in salt-free solution and electroporations were performed at 18 kV/cm and 129 Ohms in ice-cooled 1-mm cuvettes. Pulse lengths were typically between 4 and 5 milliseconds. One ml of P medium was added and the cells were incubated for 1 hour at 28° C. Dilutions were spread onto F-agar plates containing 25-50 µg/ml kanamycin and incubated at 28° C. Putative transformants were confirmed to contain the desired plasmid by PCR analysis.

Culture Conditions for Evaluating Coenzyme Q10 Production

Coenzyme Q10 production was tested in fed-batch cultivations of *P. zeaxanthinifaciens* strains R114/pBBR-K-mev-opR114-PcrtE-dds$A_{wt}$ and R114/pBBR-K-mev-op-(mvk-K93E)-PcrtE-dds$A_{wt}$. All cultures were initiated from frozen cell suspensions (stored as 25% glycerol stocks at −80° C.). The precultures for the fed-batch fermentations were prepared in duplicate 2-liter baffled shake flasks containing 200 ml of 362F/2 medium each. Two milliliters of thawed cell suspension were used as inoculum for each flask. The initial pH of the precultures was 7.2. The precultures were incubated at 28° C. with shaking at 250 rpm for 28 hours, after which time the optical density at 660 nm ($OD_{660}$) was between 14 and 22 absorbance units, depending on the strain used. Main cultures were grown in Biostat ED Bioreactors (B. Braun Biotech International, Melsungen, Germany) containing medium having the following composition (per liter distilled water): D-glucose-$H_2O$, 25 g; yeast extract (Tastone 900), 17 g; NaCl, 4.0 g; $MgSO_4.7H_2O$, 6.25 g; $(NH_4)_2Fe(SO_4)_2.6H_2O$, 0.5 g; $ZnSO_4.7H_2O$, 0.038 g; $MnSO_4.H_2O$, 0.013 g; $NiSO_4.6H_2O$, 0.001 g; $CaCl_2.2H_2O$, 0.47 g; $FeCl_{3.6}H_2O$, 0.062 g; niacin, 0.01 g; $NH_4Cl$, 0.5 g; antifoam, 0.1 ml; KP solution, 3.5 ml. The composition of KP solution is (per liter distilled water): $K_2HPO_4$, 250 g; $NaH_2PO_4.2H_2O$, 200 g; $(NH_4)_2HPO_4$, 100 g. kanamycin (50 mg/l final concentration) was added to the medium for plasmid-carrying strains. The feeding solution used in all processes had the following composition (per liter distilled water): D-glucose-$H_2O$, 550 g; KP solution, 18.25 ml. The initial volume in the bioreactor (after inoculation) was 8.0 L. Precultures were diluted as needed with sterile water such that addition of 400 ml to the bioreactor achieved an initial $OD_{660}$ value of 0.5. Fermentation conditions were automatically controlled as follows: 28° C., pH 7.2 (pH controlled with addition of 28% $NH_4OH$), dissolved oxygen controlled at a minimum of 40% relative value (in cascade with agitation), minimum agitation of 300 rpm and an aeration rate of 1 v.v.m. (relative to final volume). The cultivations proceeded under these conditions without addition of feed solution for about 20 hours (batch phase). After this time, a decrease in agitation speed, cessation of base consumption, a sharp pH increase and a decrease in $CO_2$ production were the indication that the initial glucose was exhausted and the feeding was started. A standard feed profile was defined as follows (from feeding start point): ramp from 50 g/h to 80 g/h in 17 hours, continue at 80 g/h for 7 hours then ramp down to 55 g/h in 11 hours and continue at 55 g/h for the rest of the fermentation (total fermentation time=70 hours). The final volumes of the main cultures were about 10 liters.

Analytical Methods

Reagents. Acetonitrile, dimethylsulfoxide (DMSO), tetrahydrofuran (THF), tert-butyl methyl ether (TBME) and butylated hydroxytoluene (BHT) were puriss., p.a. or HPLC grade and were obtained from Fluka (Switzerland). Coenzyme Q10 was purchased from Fluka. Methanol (Lichrosolv) was purchased from Merck, Darmstadt, Germany. Carotenoid standards were obtained from the Chemistry Research Department, Roche Vitamins Ltd., Switzerland.

Sample preparation and extraction. Four hundred microliters of whole broth were transferred to a disposable 15 ml polypropylene centrifuge tube. Four milliliters of stabilized extraction solution (0.5 g/l BHT in 1:1 (v/v) DMSO/THF) were added and the samples were mixed for 20 minutes in a laboratory shaker (IKA, Germany) to enhance extraction. Finally, the samples were centrifuged and the supernatants were transferred to amber glass vials for analysis by high performance liquid chromatography (HPLC).

HPLC. A reversed phase HPLC method was developed for the simultaneous determination of ubiquinones and their corresponding hydroquinones. The method is able to clearly separate the carotenoids zeaxanthin, phytoene, β-cryptoxanthin, β-carotene and lycopene from coenzyme Q10. Chromatography was performed using an Agilent 1100 HPLC system equipped with a temperature-controlled autosampler and a diode array detector. The method parameters were as follows:

| | |
|---|---|
| Column | YMC Carotenoid C30 column |
| | 3 micron, steel, 150 mm length × 3.0 mm I.D. |
| | (YMC, Part No. CT99S031503QT) |
| Guard column | Security Guard C18 (ODS, Octadecyl) |
| | 4 mm length × 3.0 mm I.D. |
| | (Phenomenex, Part No. AJO-4287) |
| Typical column pressure | 60 bar at start |
| Flow rate | 0.5 ml/min |
| Mobile phase | Mixture of acetonitrile(A):methanol(B):TBME(C) |
| Gradient profile | Time (min)   % A   % B   % C |
| | 0   60   15   25 |
| | 13   60   15   25 |
| | 20   0   0   100 |
| | 22   60   15   25 |
| | 22   60   15   25 |
| Post time | 4 minutes |
| Injection volume | 10 µl |
| Column temperature | 15° C. |
| Detection | Three wavelengths were used for detection of specific compounds according to Table 5. |

TABLE 5

HPLC retention times and wavelengths used.

| Compound | Wavelength (nm) | Retention times (min) |
|---|---|---|
| Zeaxanthin (Z-isomers) | 450 | 4.2, 6.4 |
| E-Zeaxanthin | 450 | 5.2 |
| Phytoene | 280 | 7.7 |
| β-Cryptoxanthin | 450 | 8.6 |
| Ubiquinol 10 | 210 | 11.4 |
| Coenzyme Q10 | 210 | 12.8 |
| β-Carotene | 450 | 14.5 |
| Lycopene | 450 | 22.0 |

Calculations, selectivity, linearity, limit of detection and reproducibility. Calculations were based on peak areas. The selectivity of the method was verified by injecting standard solutions of the relevant reference compounds. The target compounds (coenzyme Q10 and ubiquinol 10) were completely separated and showed no interference. A dilution series of coenzyme Q10 in extraction solution (see above) was prepared and analyzed. A linear range was found from 5 mg/l to 50 mg/l. The correlation coefficient was 0.9999. The limit of detection for coenzyme Q10 by this HPLC method was determined to be 4 mg/l. The reproducibility of the method including the extraction procedure was checked. Ten individual sample preparations were compared. The relative standard deviation was determined to be 4%.

Coenzyme Q10 Production Results

Under the fed-batch cultivation conditions described above, the final concentration of coenzyme Q10 produced by *P. zeaxanthinifaciens* strain R114/pBBR-K-mev-op-(mvk-K93E)-PcrtE-ddsA$_{wt}$ was 34% higher than observed for strain R114/pBBR-K-mev-opR114-PcrtE-ddsA$_{wt}$. This difference was not attributable simply to differences in the growth of the two strains, as strain R114/pBBR-K-mev-op-(mvk-K93E)-PcrtE-ddsA$_{wt}$ also showed a 12% higher specific coenzyme Q10 production (units coenzyme Q10/gram cell dry mass/hour) compared to strain R114/pBBR-K-mev-opR114-PcrtE-ddsA$_{wt}$. Further, strain R114/pBBR-K-mev-op-(mvk-K93E)-PcrtE-ddsA$_{wt}$ also showed a 31% decrease on mevalonate accumulation in the broth compared to strain R1114/pBBR-K-mev-opR114-PcrtE-ddsA$_{wt}$. This comparison showed that the K93E mutation in plasmid pBBR-K-mev-op-(mvk-K93E)-PcrtE-ddsA$_{wt}$ is directly responsible for the improved production of coenzyme Q10.

EXAMPLE 8

Effect of the I17T Mutation on the Solubility of *Paracoccus zeaxanthinifaciens* Mevalonate Kinase For human mevalonate kinase, mutants E19A, E19Q and H20A were shown to be completely insoluble after IPTG-induction of *E. coli* transformants (Potter and Miziorko, J. Biol. Chem. 272, 25449-25454, 1997). The His$_6$-tagged *Paracoccus zeaxanthinifaciens* R114 mevalonate kinase (SEQ ID NO:15) also displayed a pronounced tendency to aggregate/precipitate, in particular in buffer solutions with rather high ionic strength (e.g., 50 mM NaH$_2$PO$_4$, pH 8.0, 300 mM NaCl, 250 mM imidazole). Surprisingly, the His$_6$-tagged *Paracoccus zeaxanthinifaciens* R114 mevalonate kinase mutant I17T was completely soluble and stable under the same conditions, so that this mutant enzyme is much better suited for applications requiring soluble mevalonate kinase.

EXAMPLE 9

Feedback Inhibition of Mevalonate Kinase with Different Downstream Products of the Pathway Different mevalonate kinases were previously reported to be sensitive to feedback inhibition by the following downstream products of the mevalonate pathway: IPP, DMAPP, GPP, FPP, GGPP, phytyl-PP, farnesol, dolichol phosphate. At 138 μM of GGPP, FPP, GPP, IPP, or DMAPP, the activity of His$_6$-tagged *Paracoccus zeaxanthinifaciens* mevalonate kinase was inhibited by 98%, 80.1%, 18.6%, 16.3% and 14.7%, respectively. The resistance of the *Paracoccus zeaxanthinifaciens* mevalonate kinase mutant I17T/G47D/K93E/P132S to feedback inhibition by FPP (92 μM) or GGPP (17.6 μM) was 83% and 92%, respectively.

EXAMPLE 10

Identification of Corresponding Residues in Mevalonate Kinases that are Homologous to *Paracoccus zeaxanthinifaciens* Mevalonate Kinase With the sequence alignment program GAP (GCG Wisconsin Package, version 10.2, Accelrys Inc., 9685 Scranton Road, San Diego, Calif. 92121-3752, USA; gap creation penalty 8; gap extension penalty 2), the following residues corresponding to specific amino acid positions of the amino acid sequence of *Paracoccus zeaxanthinifaciens* mevalonate kinase (SEQ ID NO:1) were identified:

| SEQ ID NO: | Amino acid position | | | | | | | | |
|---|---|---|---|---|---|---|---|---|---|
| 1  | I17 | G74  | K93  | V94  | P132 | R167 | K169 | R204 | C266 |
| 2  | I15 | S45  | K90  | V94  | (—)  | E163 | P165 | R215 | C275 |
| 3  | I15 | S45  | P83  | T84  | P127 | P167 | K169 | R215 | C275 |
| 4  | I15 | S45  | K93  | V94  | L129 | R171 | S173 | R215 | C275 |
| 5  | I12 | P43  | S83  | T84  | P131 | E167 | E179 | K215 | D269 |
| 6  | I14 | S45  | Q93  | E94  | N131 | L172 | K174 | K216 | C279 |
| 7  | I14 | N44  | V76  | Q77  | P120 | P162 | S164 | R208 | I268 |
| 8  | I14 | G46  | E80  | V81  | (—)  | L136 | L138 | Y173 | S238 |
| 9  | I14 | G46  | E80  | V81  | (—)  | L136 | L138 | Y173 | S238 |
| 10 | I12 | (—)  | K78  | A79  | (—)  | L135 | L137 | F172 | V227 |
| 11 | I12 | T37  | (—)  | (—)  | P80  | R115 | H117 | Y152 | I208 |
| 12 | I10 | S35  | (—)  | (—)  | G76  | G111 | M113 | (—)  | D197 |
| 13 | I10 | Q40  | (—)  | (—)  | T93  | K129 | L131 | E166 | I220 |
| 14 | I14 | (—)  | S58  | A59  | P93  | D128 | L130 | A165 | I223 |
| 15 | I26 | G56  | K102 | V103 | P141 | R176 | K178 | R213 | C275 |
| 30 | I13 | (—)  | S86  | I87  | P135 | R178 | T184 | K224 | C290 |

Amino acid numbering according to the respective sequences SEQ ID NOs: 1-15 and 30.
(—) No homologous residue has been identified.

Examples of amino acid sequences of non-modified mevalonate kinases include but are not limited to the following amino acid sequences (SEQ ID NOs: 1-15 and 30). The nucleotide sequences encoding the non-modified mevalonate kinases (SEQ ID NOs:1-14 and 30) are shown in SEQ ID NOs:16-29 and 31, respectively.

SEQ ID No:1: Amino acid sequence of *Paracoccus zeaxanthinifaciens* mevalonate kinase.

SEQ ID NO:2: Amino acid sequence of human mevalonate kinase (Swiss-Prot accession no. Q03426).

SEQ ID NO:3: Amino acid sequence of mouse mevalonate kinase (Swiss-Prot accession no. Q9R008).

SEQ ID NO:4: Amino acid sequence of rat mevalonate kinase (Swiss-Prot accession no. P17256).

SEQ ID NO:5: Amino acid sequence of *Arabidopsis thaliana* mevalonate kinase (Swiss-Prot accession no. P46086).

SEQ ID NO:6: Amino acid sequence of yeast mevalonate kinase (Swiss-Prot accession no. P07277).

SEQ ID NO:7: Amino acid sequence of *Schizosaccharomyces pombe* mevalonate kinase (Swiss-Prot accession no. Q09780).

SEQ ID NO:8: Amino acid sequence of *Pyrococcus abyssi* mevalonate kinase (Swiss-Prot accession no. Q9V187).

SEQ ID NO:9: Amino acid sequence of *Pyrococcus horikoshii* mevalonate kinase (Swiss-Prot accession no. O59291).

SEQ ID NO:10: Amino acid sequence of *Pyrococcus furiosus* mevalonate kinase (Swiss-Prot accession no. Q8U0F3).

SEQ ID NO:11: Amino acid sequence of *Methanobacterium thermoautotrophicum* mevalonate kinase (Swiss-Prot accession no. Q50559).

SEQ ID NO:12: Amino acid sequence of *Archaeoglobus fulgidus* mevalonate kinase (Swiss-Prot accession no. O27995).

SEQ ID NO:13: Amino acid sequence of *Methanococcus jannaschii* mevalonate kinase (Swiss-Prot accession no. Q58487).

SEQ ID NO:13: Amino acid sequence of *Methanococcus jannaschii* mevalonate kinase (Swiss-Prot accession no. Q58487).

SEQ ID NO:14: Amino acid sequence of *Aeropyrum pernix* mevalonate kinase (Swiss-Prot accession no. Q9Y946).

SEQ ID NO:15: Amino acid sequence of His$_6$-tagged mevalonate kinase of *Paracoccus zeaxanthinifaciens*.

SEQ ID NO:16: DNA sequence of *Paracoccus zeaxanthinifaciens* mevalonate kinase.

SEQ ID NO:17: DNA sequence of human mevalonate kinase (Genbank accession no. M88468).

SEQ ID NO:18: DNA sequence of mouse mevalonate kinase (Genbank accession no. AF137598).

SEQ ID NO:19: DNA sequence of rat mevalonate kinase (Genbank accession no. M29472).

SEQ ID NO:20: DNA sequence of *Arabidopsis thaliana* mevalonate kinase (Genbank accession no. X77793).

SEQ ID NO:21: DNA sequence of yeast mevalonate kinase (Genbank accession no. X06114).

SEQ ID NO:22: DNA sequence of *Schizosaccharomyces pombe* mevalonate kinase (Genbank accession no. AB000541).

SEQ ID NO:23: DNA sequence of *Pyrococcus abyssi* mevalonate kinase (Genbank accession no. AJ248284).

SEQ ID NO:24: DNA sequence of *Pyrococcus horikoshii* mevalonate kinase (Genbank accession no. AB009515; reverse direction).

SEQ ID NO:25: DNA sequence of *Pyrococcus furiosus* mevalonate kinase (Genbank accession no. AE010263; reverse direction).

SEQ ID NO:26: DNA sequence of *Methanobacterium thermoautotrophicum* mevalonate kinase (Genbank accession no. U47134).

SEQ ID NO:27: DNA sequence of *Archaeoglobus fulgidus* mevalonate kinase (Genbank accession no. AE000946; reverse direction).

SEQ ID NO:28: DNA sequence of *Methanococcus jannaschii* mevalonate kinase (Genbank accession no. U67551).

SEQ ID NO:29: DNA sequence of *Aeropyrum pernix* mevalonate kinase (Genbank accession no. AP000064).

SEQ ID NO:30: Amino acid sequence of *Phaffia rhodozyma* ATCC96594 mevalonate kinase.

SEQ ID NO:31: Gene (DNA) sequence of *Phaffia rhodozyma* ATCC96594 mevalonate kinase. The mevalonate kinase gene consists of 4 introns and 5 exons.

| | |
|---|---|
| Exon 1: | 1021-1124 |
| Intron 1: | 1125-1630 |
| Exon 2: | 1631-1956 |
| Intron 2: | 1957-2051 |
| Exon 3: | 2052-2366 |
| Intron 3: | 2367-2446 |
| Exon 4: | 2447-2651 |
| Intron 4: | 2652-2732 |
| Exon 5: | 2733-3188 |
| PolyA site: | 3284 |

SEQ ID NO:32: DNA sequence of the His$_6$-tagged *Paracoccus zeaxanthinifaciens* mevalonate kinase mutant I17T.

SEQ ID NO:33: DNA sequence of the His$_6$-tagged *Paracoccus zeaxanthinifaciens* mevalonate kinase mutant I17T/G47D/K93E/P132S.

The invention claimed is:

1. An isolated modified mevalonate kinase which exhibits a sensitivity to feedback inhibition which is reduced in comparison to the corresponding non-modified mevalonate kinase wherein the non-modified mevalonate kinase is a naturally occurring fungal or bacterial mevalonate kinase;
the modified mevalonate kinase contains a mutation when compared with the amino acid sequence of the corresponding non-modified mevalonate kinase wherein the mutation is at the amino acid position corresponding to amino acid position 17 of the sequence as shown in SEQ ID NO:1, and
wherein the modified mevalonate kinase is at least 95% homologous to SEQ ID NO:1.

2. The modified mevalonate kinase according to claim 1 wherein said feedback inhibition is feedback inhibition by farnesyl diphosphate or geranylgeranyl diphosphate.

3. The modified mevalonate kinase according to claim 1 wherein the modified mevalonate kinase exhibits a feedback resistance of at least 10% in comparison to the corresponding non-modified mevalonate kinase.

4. The modified mevalonate kinase according to claim 1 wherein the mutation is an amino acid substitution.

5. A modified mevalonate kinase according to claim 1 wherein the modified mevalonate kinase contains two amino acid substitutions when compared with the amino acid sequence of the corresponding non-modified mevalonate kinase.

6. A modified mevalonate kinase according to claim 1 wherein the modified mevalonate kinase contains three amino acid substitutions when compared with the amino acid sequence of the corresponding non-modified mevalonate kinase.

7. A modified mevalonate kinase according to claim 1 wherein the modified mevalonate kinase contains four amino acid substitutions when compared with the amino acid sequence of the corresponding non-modified mevalonate kinase.

8. The modified mevalonate kinase according to claim 4 wherein the substitution at the amino acid position corresponding to position 17 of the sequence as shown in SEQ ID NO:1 consists of the replacement of isoleucine with threonine.

9. A polynucleotide comprising a nucleotide sequence which codes for the modified mevalonate kinase according to claim 1.

10. The polynucleotide according to claim 9 wherein the nucleotide sequence which codes for the modified mevalonate kinase according to claim 1 is selected from the group consisting of the nucleotide sequences SEQ ID NOs: 32 and 33.

11. A vector or plasmid comprising the polynucleotide according to claim 9.

12. The vector or plasmid according to claim 11 further comprising at least one marker gene.

13. A host cell comprising the vector or plasmid according to claim 11.

14. The host cell according to claim 13 which is selected from the group consisting of *E. coli, Paracoccus zeaxanthinifaciens, Rhodobacter*, and *Saccharomyces cerevisiae*.

15. A method for producing an isoprenoid compound comprising:
(a) culturing the host cell according to claim 13 in a suitable medium; and
(b) optionally separating the isoprenoid compound from the medium.

16. A method according to claim 15 wherein the isoprenoid compound is coenzyme Q10.

17. A method for producing the modified mevalonate kinase according to claim 1 comprising:
(a) culturing in a suitable medium a population of host cells, which comprise a vector or plasmid that comprises a polynucleotide that encodes the modified mevalonate kinase wherein
the modified mevalonate kinase contains a mutation when compared with the amino acid sequence of the corresponding non-modified mevalonate kinase wherein the mutation is at the amino acid position corresponding to amino acid position 17 of the sequence as shown in SEQ ID NO:1 and the modified mevalonate kinase is at least 95% homologous to SEQ ID NO:1
(b) optionally recovering the modified mevalonate kinase from the cells or from the medium.

18. A method for the preparation of a mevalonate kinase having reduced sensitivity to feedback inhibition, comprising the following steps:
(a) providing a polynucleotide encoding a first mevalonate kinase which exhibits sensitivity to feedback inhibition, wherein the first mevalonate kinase is a naturally occurring fungal or bacterial mevalonate kinase (b) introducing a mutation into the polynucleotide sequence such that the mutated polynucleotide sequence encodes a second mevalonate kinase which contains a mutation when compared to the first mevalonate kinase wherein the mutation is at the amino acid position corresponding to amino acid position 17 of the sequence as shown in SEQ ID NO:1, and wherein the second mevalonate kinase is at least 95% homologous to SEQ ID NO:1;

(c) optionally inserting the mutated polynucleotide in a vector or plasmid;

(d) introducing the mutated polynucleotide or the vector or plasmid into a suitable host cell; and (e) culturing the host cell under conditions that allow expression of the second mevalonate kinase.

* * * * *

SEQUENCE LISTING

```
<160> NUMBER OF SEQ ID NOS: 33

<210> SEQ ID NO 1
<211> LENGTH: 378
<212> TYPE: PRT
<213> ORGANISM: Paracoccus zeaxanthinifaciens

<400> SEQUENCE: 1

Met Ser Thr Gly Arg Pro Glu Ala Gly Ala His Ala Pro Gly Lys Leu
1               5                   10                  15

Ile Leu Ser Gly Glu His Ser Val Leu Tyr Gly Ala Pro Ala Leu Ala
            20                  25                  30

Met Ala Ile Ala Arg Tyr Thr Glu Val Trp Phe Thr Pro Leu Gly Ile
        35                  40                  45

Gly Glu Gly Ile Arg Thr Thr Phe Ala Asn Leu Ser Gly Gly Ala Thr
    50                  55                  60

Tyr Ser Leu Lys Leu Leu Ser Gly Phe Lys Ser Arg Leu Asp Arg Arg
65                  70                  75                  80

Phe Glu Gln Phe Leu Asn Gly Asp Leu Lys Val His Lys Val Leu Thr
                85                  90                  95

His Pro Asp Asp Leu Ala Val Tyr Ala Leu Ala Ser Leu Leu His Asp
            100                 105                 110

Lys Pro Gly Thr Ala Ala Met Pro Gly Ile Gly Ala Met His His
        115                 120                 125

Leu Pro Arg Pro Gly Glu Leu Gly Ser Arg Thr Glu Leu Pro Ile Gly
    130                 135                 140

Ala Gly Met Gly Ser Ser Ala Ala Ile Val Ala Ala Thr Thr Val Leu
```

```
                145                 150                 155                 160
        Phe Glu Thr Leu Leu Asp Arg Pro Lys Thr Pro Glu Gln Arg Phe Asp
                        165                 170                 175

Arg Val Arg Phe Cys Glu Arg Leu Lys His Gly Lys Ala Gly Pro Ile
                    180                 185                 190

Asp Ala Ala Ser Val Val Arg Gly Gly Leu Val Arg Val Gly Gly Asn
                    195                 200                 205

Gly Pro Gly Ser Ile Ser Ser Phe Asp Leu Pro Glu Asp His Asp Leu
                210                 215                 220

Val Ala Gly Arg Gly Trp Tyr Trp Val Leu His Gly Arg Pro Val Ser
        225                 230                 235                 240

Gly Thr Gly Glu Cys Val Ser Ala Val Ala Ala His Gly Arg Asp
                        245                 250                 255

Ala Ala Leu Trp Asp Ala Phe Ala Val Cys Thr Arg Ala Leu Glu Ala
                    260                 265                 270

Ala Leu Leu Ser Gly Gly Ser Pro Asp Ala Ala Ile Thr Glu Asn Gln
                    275                 280                 285

Arg Leu Leu Glu Arg Ile Gly Val Val Pro Ala Ala Thr Gln Ala Leu
                290                 295                 300

Val Ala Gln Ile Glu Glu Ala Gly Ala Ala Lys Ile Cys Gly Ala
        305                 310                 315                 320

Gly Ser Val Arg Gly Asp His Gly Gly Ala Val Leu Val Arg Ile Asp
                        325                 330                 335

Asp Ala Gln Ala Met Ala Ser Val Met Ala Arg His Pro Asp Leu Asp
                    340                 345                 350

Trp Ala Pro Leu Arg Met Ser Arg Thr Gly Ala Ala Pro Gly Pro Ala
                    355                 360                 365

Pro Arg Ala Gln Pro Leu Pro Gly Gln Gly
                370                 375

<210> SEQ ID NO 2
<211> LENGTH: 396
<212> TYPE: PRT
<213> ORGANISM: homo sapiens

<400> SEQUENCE: 2

Met Leu Ser Glu Val Leu Leu Val Ser Ala Pro Gly Lys Val Ile Leu
1               5                   10                  15

His Gly Glu His Ala Val Val His Gly Lys Val Ala Leu Ala Val Ser
                20                  25                  30

Leu Asn Leu Arg Thr Phe Leu Arg Leu Gln Pro His Ser Asn Gly Lys
            35                  40                  45

Val Asp Leu Ser Leu Pro Asn Ile Gly Ile Lys Arg Ala Trp Asp Val
        50                  55                  60

Ala Arg Leu Gln Ser Leu Asp Thr Ser Phe Leu Glu Gln Gly Asp Val
65                  70                  75                  80

Thr Thr Pro Thr Ser Glu Gln Val Glu Lys Leu Lys Glu Val Ala Gly
                85                  90                  95

Leu Pro Asp Asp Cys Ala Val Thr Glu Arg Leu Ala Val Leu Ala Phe
            100                 105                 110

Leu Tyr Leu Tyr Leu Ser Ile Cys Arg Lys Gln Arg Ala Leu Pro Ser
            115                 120                 125

Leu Asp Ile Val Val Trp Ser Glu Leu Pro Pro Gly Ala Gly Leu Gly
        130                 135                 140
```

Ser Ser Ala Ala Tyr Ser Val Cys Leu Ala Ala Leu Leu Thr Val
145                 150                 155                 160

Cys Glu Glu Ile Pro Asn Pro Leu Lys Asp Gly Asp Cys Val Asn Arg
            165                 170                 175

Trp Thr Lys Glu Asp Leu Glu Leu Ile Asn Lys Trp Ala Phe Gln Gly
        180                 185                 190

Glu Arg Met Ile His Gly Asn Pro Ser Gly Val Asp Asn Ala Val Ser
    195                 200                 205

Thr Trp Gly Gly Ala Leu Arg Tyr His Gln Gly Lys Ile Ser Ser Leu
210                 215                 220

Lys Arg Ser Pro Ala Leu Gln Ile Leu Leu Thr Asn Thr Lys Val Pro
225                 230                 235                 240

Arg Asn Thr Arg Ala Leu Val Ala Gly Val Arg Asn Arg Leu Leu Lys
                245                 250                 255

Phe Pro Glu Ile Val Ala Pro Leu Leu Thr Ser Ile Asp Ala Ile Ser
            260                 265                 270

Leu Glu Cys Glu Arg Val Leu Gly Glu Met Gly Glu Ala Pro Ala Pro
        275                 280                 285

Glu Gln Tyr Leu Val Leu Glu Glu Leu Ile Asp Met Asn Gln His His
    290                 295                 300

Leu Asn Ala Leu Gly Val Gly His Ala Ser Leu Asp Gln Leu Cys Gln
305                 310                 315                 320

Val Thr Arg Ala Arg Gly Leu His Ser Lys Leu Thr Gly Ala Gly Gly
                325                 330                 335

Gly Gly Cys Gly Ile Thr Leu Leu Lys Pro Gly Leu Glu Gln Pro Glu
            340                 345                 350

Val Glu Ala Thr Lys Gln Ala Leu Thr Ser Cys Gly Phe Asp Cys Leu
        355                 360                 365

Glu Thr Ser Ile Gly Ala Pro Gly Val Ser Ile His Ser Ala Thr Ser
    370                 375                 380

Leu Asp Ser Arg Val Gln Gln Ala Leu Asp Gly Leu
385                 390                 395

<210> SEQ ID NO 3
<211> LENGTH: 395
<212> TYPE: PRT
<213> ORGANISM: mouse

<400> SEQUENCE: 3

Met Leu Ser Glu Ala Leu Leu Val Ser Ala Pro Gly Lys Val Ile Leu
1               5                   10                  15

His Gly Glu His Ala Val Val His Gly Lys Val Ala Leu Ala Ala Ala
            20                  25                  30

Leu Asn Leu Arg Thr Phe Leu Leu Arg Pro Gln Ser Asn Gly Lys
        35                  40                  45

Val Ser Val Asn Leu Pro Asn Ile Gly Ile Lys Gln Val Trp Asp Val
    50                  55                  60

Gly Met Leu Gln Arg Leu Asp Thr Ser Phe Leu Glu Gln Gly Asp Val
65                  70                  75                  80

Ser Val Pro Thr Leu Glu Gln Leu Glu Lys Leu Lys Lys Met Gly Asp
                85                  90                  95

Leu Pro Arg Asp Arg Ala Gly Asn Glu Gly Met Ala Leu Leu Ala Phe
            100                 105                 110

Leu Tyr Leu Tyr Leu Ala Ile Cys Arg Lys Gln Arg Thr Leu Pro Ser
        115                 120                 125

```
Leu Asp Met Val Val Trp Ser Glu Leu Pro Gly Ala Gly Leu Gly
    130                 135                 140

Ser Ser Ala Ala Tyr Ser Val Cys Leu Ala Ala Leu Leu Thr Ala
145                 150                 155                 160

Cys Glu Glu Val Ser Asn Pro Leu Lys Asp Gly Val Ser Val Ser Arg
                    165                 170                 175

Trp Pro Glu Glu Asp Leu Lys Ser Ile Asn Lys Trp Ala Phe Glu Gly
                180                 185                 190

Glu Arg Val Ile His Gly Asn Pro Ser Gly Val Asp Asn Ala Val Ser
            195                 200                 205

Thr Trp Gly Gly Ala Leu Arg Phe Gln Gln Gly Thr Met Ser Ser Leu
    210                 215                 220

Lys Ser Leu Pro Ser Leu Gln Ile Leu Leu Thr Asn Thr Lys Val Pro
225                 230                 235                 240

Arg Ser Thr Lys Ala Leu Val Ala Ala Val Arg Ser Arg Leu Thr Lys
                245                 250                 255

Phe Pro Glu Ile Val Ala Pro Leu Leu Thr Ser Ile Asp Ala Ile Ser
                260                 265                 270

Leu Glu Cys Glu Arg Val Leu Gly Glu Met Val Ala Ala Pro Val Pro
            275                 280                 285

Glu Gln Tyr Leu Val Leu Glu Glu Leu Ile Asp Met Asn Gln His His
    290                 295                 300

Leu Asn Ala Leu Gly Val Gly His Asn Ser Leu Asp Gln Leu Cys Gln
305                 310                 315                 320

Val Thr Ala Ala His Gly Leu His Ser Lys Leu Thr Gly Ala Gly Gly
                325                 330                 335

Gly Gly Cys Gly Ile Thr Leu Leu Lys Pro Gly Leu Glu Gln Ala Thr
                340                 345                 350

Val Glu Ala Ala Lys Gln Ala Leu Thr Ser Cys Gly Phe Asp Cys Trp
            355                 360                 365

Glu Thr Ser Ile Gly Ala Pro Gly Val Ser Thr His Ser Ala Ala Ala
    370                 375                 380

Val Gly Asp Pro Val Arg Gln Ala Leu Gly Leu
385                 390                 395

<210> SEQ ID NO 4
<211> LENGTH: 395
<212> TYPE: PRT
<213> ORGANISM: rat

<400> SEQUENCE: 4

Met Leu Ser Glu Val Leu Leu Val Ser Ala Pro Gly Lys Val Ile Leu
1               5                   10                  15

His Gly Glu His Ala Val Val His Gly Lys Val Ala Leu Ala Val Ala
            20                  25                  30

Leu Asn Leu Arg Thr Phe Leu Val Arg Pro Gln Ser Asn Gly Lys
        35                  40                  45

Val Ser Leu Asn Leu Pro Asn Val Gly Ile Lys Gln Val Trp Asp Val
    50                  55                  60

Ala Thr Leu Gln Leu Leu Asp Thr Gly Phe Leu Glu Gln Gly Asp Val
65                  70                  75                  80

Pro Ala Pro Thr Leu Glu Gln Leu Glu Lys Leu Lys Lys Val Ala Gly
                85                  90                  95

Leu Pro Arg Asp Cys Val Gly Asn Glu Gly Leu Ser Leu Leu Ala Phe
```

```
                100                 105                 110
Leu Tyr Leu Tyr Leu Ala Ile Cys Arg Lys Gln Arg Thr Leu Pro Ser
            115                 120                 125

Leu Asp Ile Met Val Trp Ser Glu Leu Pro Pro Gly Ala Gly Leu Gly
            130                 135                 140

Ser Ser Ala Ala Tyr Ser Val Cys Val Ala Ala Leu Leu Thr Ala
145                 150                 155                 160

Cys Glu Glu Val Thr Asn Pro Leu Lys Asp Arg Gly Ser Ile Gly Ser
                165                 170                 175

Trp Pro Glu Glu Asp Leu Lys Ser Ile Asn Lys Trp Ala Tyr Glu Gly
            180                 185                 190

Glu Arg Val Ile His Gly Asn Pro Ser Gly Val Asp Asn Ser Val Ser
            195                 200                 205

Thr Trp Gly Gly Ala Leu Arg Tyr Gln Gln Gly Lys Met Ser Ser Leu
            210                 215                 220

Lys Arg Leu Pro Ala Leu Gln Ile Leu Leu Thr Asn Thr Lys Val Pro
225                 230                 235                 240

Arg Ser Thr Lys Ala Leu Val Ala Gly Val Arg Ser Arg Leu Ile Lys
                245                 250                 255

Phe Pro Glu Ile Met Ala Pro Leu Leu Thr Ser Ile Asp Ala Ile Ser
            260                 265                 270

Leu Glu Cys Glu Arg Val Leu Gly Glu Met Ala Ala Pro Val Pro
            275                 280                 285

Glu Gln Tyr Leu Val Leu Glu Glu Leu Met Asp Met Asn Gln His His
            290                 295                 300

Leu Asn Ala Leu Gly Val Gly His Ala Ser Leu Asp Gln Leu Cys Gln
305                 310                 315                 320

Val Thr Ala Ala His Gly Leu His Ser Lys Leu Thr Gly Ala Gly Gly
                325                 330                 335

Gly Gly Cys Gly Ile Thr Leu Leu Lys Pro Gly Leu Glu Arg Ala Lys
            340                 345                 350

Val Glu Ala Ala Lys Gln Ala Leu Thr Gly Cys Gly Phe Asp Cys Trp
            355                 360                 365

Glu Thr Ser Ile Gly Ala Pro Gly Val Ser Met His Ser Ala Thr Ser
            370                 375                 380

Ile Glu Asp Pro Val Arg Gln Ala Leu Gly Leu
385                 390                 395

<210> SEQ ID NO 5
<211> LENGTH: 378
<212> TYPE: PRT
<213> ORGANISM: Arabidopsis thaliana

<400> SEQUENCE: 5

Met Glu Val Lys Ala Arg Ala Pro Gly Lys Ile Ile Leu Ala Gly Glu
1               5                   10                  15

His Ala Val Val His Gly Ser Thr Ala Val Ala Ala Ile Asp Leu
            20                  25                  30

Tyr Thr Tyr Val Thr Leu Arg Phe Pro Leu Pro Ser Ala Glu Asn Asn
            35                  40                  45

Asp Arg Leu Thr Leu Gln Leu Lys Asp Ile Ser Leu Glu Phe Ser Trp
        50                  55                  60

Ser Leu Ala Arg Ile Lys Glu Ala Ile Pro Tyr Asp Ser Ser Thr Leu
65                  70                  75                  80
```

```
Cys Arg Ser Thr Pro Ala Ser Cys Ser Glu Glu Thr Leu Lys Ser Ile
                85                  90                  95

Ala Val Leu Val Glu Glu Gln Asn Leu Pro Lys Glu Lys Met Trp Leu
            100                 105                 110

Ser Ser Gly Ile Ser Thr Phe Leu Trp Leu Tyr Thr Arg Ile Ile Gly
            115                 120                 125

Phe Asn Pro Ala Thr Val Val Ile Asn Ser Glu Leu Pro Tyr Gly Ser
        130                 135                 140

Gly Leu Gly Ser Ser Ala Ala Leu Cys Val Ala Leu Thr Ala Ala Leu
145                 150                 155                 160

Leu Ala Ser Ser Ile Ser Glu Lys Thr Arg Gly Asn Gly Trp Ser Ser
                165                 170                 175

Leu Asp Glu Thr Asn Leu Glu Leu Leu Asn Lys Trp Ala Phe Glu Gly
            180                 185                 190

Glu Lys Ile Ile His Gly Lys Pro Ser Gly Ile Asp Asn Thr Val Ser
        195                 200                 205

Ala Tyr Gly Asn Met Ile Lys Phe Cys Ser Gly Glu Ile Thr Arg Leu
    210                 215                 220

Gln Ser Asn Met Pro Leu Arg Met Leu Ile Thr Asn Thr Arg Val Gly
225                 230                 235                 240

Arg Asn Thr Lys Ala Leu Val Ser Gly Val Ser Gln Arg Ala Val Arg
                245                 250                 255

His Pro Asp Ala Met Lys Ser Val Phe Asn Ala Val Asp Ser Ile Ser
            260                 265                 270

Lys Glu Leu Ala Ala Ile Ile Gln Ser Lys Asp Glu Thr Ser Val Thr
        275                 280                 285

Glu Lys Glu Glu Arg Ile Lys Glu Leu Met Glu Met Asn Gln Gly Leu
    290                 295                 300

Leu Leu Ser Met Gly Val Ser His Ser Ser Ile Glu Ala Val Ile Leu
305                 310                 315                 320

Thr Thr Val Lys His Lys Leu Val Ser Lys Leu Thr Gly Ala Gly Gly
                325                 330                 335

Gly Gly Cys Val Leu Thr Leu Leu Pro Thr Gly Thr Val Val Asp Lys
            340                 345                 350

Val Val Glu Glu Leu Glu Ser Ser Gly Phe Gln Cys Phe Thr Ala Leu
        355                 360                 365

Ile Gly Gly Asn Gly Ala Gln Ile Cys Tyr
    370                 375

<210> SEQ ID NO 6
<211> LENGTH: 443
<212> TYPE: PRT
<213> ORGANISM: Saccharomyces cerevisiae

<400> SEQUENCE: 6

Met Ser Leu Pro Phe Leu Thr Ser Ala Pro Gly Lys Val Ile Ile Phe
1               5                   10                  15

Gly Glu His Ser Ala Val Tyr Asn Lys Pro Ala Val Ala Ala Ser Val
            20                  25                  30

Ser Ala Leu Arg Thr Tyr Leu Leu Ile Ser Glu Ser Ser Ala Pro Asp
        35                  40                  45

Thr Ile Glu Leu Asp Phe Pro Asp Ile Ser Phe Asn His Lys Trp Ser
    50                  55                  60

Ile Asn Asp Phe Asn Ala Ile Thr Glu Asp Gln Val Asn Ser Gln Lys
65                  70                  75                  80
```

```
Leu Ala Lys Ala Gln Gln Ala Thr Asp Gly Leu Ser Gln Glu Leu Val
                85                  90                  95

Ser Leu Leu Asp Pro Leu Leu Ala Gln Leu Ser Glu Ser Phe His Tyr
            100                 105                 110

His Ala Ala Phe Cys Phe Leu Tyr Met Phe Val Cys Leu Cys Pro His
        115                 120                 125

Ala Lys Asn Ile Lys Phe Ser Leu Lys Ser Thr Leu Pro Ile Gly Ala
    130                 135                 140

Gly Leu Gly Ser Ser Ala Ser Ile Ser Val Ser Leu Ala Leu Ala Met
145                 150                 155                 160

Ala Tyr Leu Gly Gly Leu Ile Gly Ser Asn Asp Leu Glu Lys Leu Ser
                165                 170                 175

Glu Asn Asp Lys His Ile Val Asn Gln Trp Ala Phe Ile Gly Glu Lys
            180                 185                 190

Cys Ile His Gly Thr Pro Ser Gly Ile Asp Asn Ala Val Ala Thr Tyr
        195                 200                 205

Gly Asn Ala Leu Leu Phe Glu Lys Asp Ser His Asn Gly Thr Ile Asn
    210                 215                 220

Thr Asn Asn Phe Lys Phe Leu Asp Asp Phe Pro Ala Ile Pro Met Ile
225                 230                 235                 240

Leu Thr Tyr Thr Arg Ile Pro Arg Ser Thr Lys Asp Leu Val Ala Arg
                245                 250                 255

Val Arg Val Leu Val Thr Glu Lys Phe Pro Glu Val Met Lys Pro Ile
            260                 265                 270

Leu Asp Ala Met Gly Glu Cys Ala Leu Gln Gly Leu Glu Ile Met Thr
        275                 280                 285

Lys Leu Ser Lys Cys Lys Gly Thr Asp Asp Glu Ala Val Glu Thr Asn
    290                 295                 300

Asn Glu Leu Tyr Glu Gln Leu Leu Glu Leu Ile Arg Ile Asn His Gly
305                 310                 315                 320

Leu Leu Val Ser Ile Gly Val Ser His Pro Gly Leu Glu Leu Ile Lys
                325                 330                 335

Asn Leu Ser Asp Asp Leu Arg Ile Gly Ser Thr Lys Leu Thr Gly Ala
            340                 345                 350

Gly Gly Gly Gly Cys Ser Leu Thr Leu Arg Arg Asp Ile Thr Gln
        355                 360                 365

Glu Gln Ile Asp Ser Phe Lys Lys Leu Gln Asp Asp Phe Ser Tyr
    370                 375                 380

Glu Thr Phe Glu Thr Asp Leu Gly Gly Thr Gly Cys Cys Leu Leu Ser
385                 390                 395                 400

Ala Lys Asn Leu Asn Lys Asp Leu Lys Ile Lys Ser Leu Val Phe Gln
                405                 410                 415

Leu Phe Glu Asn Lys Thr Thr Thr Lys Gln Gln Ile Asp Asp Leu Leu
            420                 425                 430

Leu Pro Gly Asn Thr Asn Leu Pro Trp Thr Ser
        435                 440

<210> SEQ ID NO 7
<211> LENGTH: 404
<212> TYPE: PRT
<213> ORGANISM: Schizosaccharomyces pombe

<400> SEQUENCE: 7

Met Ser Lys Ser Leu Ile Val Ser Ser Pro Gly Lys Thr Ile Leu Phe
```

```
              1               5              10              15

Gly Glu His Ala Val Val Tyr Gly Ala Thr Ala Leu Ala Ala Val
                 20                  25                  30

Ser Leu Arg Ser Tyr Cys Lys Leu Gln Thr Thr Asn Asn Glu Ile
                 35                  40                  45

Val Ile Val Met Ser Asp Ile Gly Thr Glu Arg Arg Trp Asn Leu Gln
 50                  55                  60

Ser Leu Pro Trp Gln His Val Thr Val Glu Asn Val Gln His Pro Ala
 65                  70                  75                  80

Ser Ser Pro Asn Leu Asp Leu Leu Gln Gly Leu Gly Glu Leu Leu Lys
                 85                  90                  95

Asn Glu Glu Asn Gly Leu Ile His Ser Ala Met Leu Cys Thr Leu Tyr
                100                 105                 110

Leu Phe Thr Ser Leu Ser Ser Pro Ser Gln Gly Cys Thr Leu Thr Ile
                115                 120                 125

Ser Ser Gln Val Pro Leu Gly Ala Gly Leu Gly Ser Ser Ala Thr Ile
                130                 135                 140

Ser Val Val Val Ala Thr Ser Leu Leu Leu Ala Phe Gly Asn Ile Glu
145                 150                 155                 160

Pro Pro Ser Ser Asn Ser Leu Gln Asn Asn Lys Ala Leu Ala Leu Ile
                165                 170                 175

Glu Ala Trp Ser Phe Leu Gly Glu Cys Cys Ile His Gly Thr Pro Ser
                180                 185                 190

Gly Ile Asp Asn Ala Val Ala Thr Asn Gly Gly Leu Ile Ala Phe Arg
                195                 200                 205

Lys Ala Thr Ala His Gln Ser Ala Met Lys Glu Phe Leu Lys Pro Lys
                210                 215                 220

Asp Thr Leu Ser Val Met Ile Thr Asp Thr Lys Gln Pro Lys Ser Thr
225                 230                 235                 240

Lys Lys Leu Val Gln Gly Val Phe Glu Leu Lys Glu Arg Leu Pro Thr
                245                 250                 255

Val Ile Asp Ser Ile Ile Asp Ala Ile Asp Gly Ile Ser Lys Ser Ala
                260                 265                 270

Val Leu Ala Leu Thr Ser Glu Ser Asp Lys Asn Ser Ser Ala Lys Lys
                275                 280                 285

Leu Gly Glu Phe Ile Val Leu Asn Gln Lys Leu Leu Glu Cys Leu Gly
                290                 295                 300

Val Ser His Tyr Ser Ile Asp Arg Val Leu Gln Ala Thr Lys Ser Ile
305                 310                 315                 320

Gly Trp Thr Lys Leu Thr Gly Ala Gly Gly Gly Cys Thr Ile Thr
                325                 330                 335

Leu Leu Thr Pro Glu Cys Lys Glu Glu Glu Phe Lys Leu Cys Lys Glu
                340                 345                 350

Ser Leu Leu Ala His Lys Asn Ser Ile Tyr Asp Val Gln Leu Gly Gly
                355                 360                 365

Pro Gly Val Ser Val Val Thr Asp Ser Asp Ser Phe Phe Pro Gln Tyr
                370                 375                 380

Glu Ser Asp Phe Asp Phe Lys Lys Leu Asn Leu Leu Ser Lys Phe Asn
385                 390                 395                 400

Lys Tyr Tyr Ile

<210> SEQ ID NO 8
<211> LENGTH: 335
```

<212> TYPE: PRT
<213> ORGANISM: Pyrococcus abyssi

<400> SEQUENCE: 8

```
Met Pro Arg Leu Val Leu Ala Ser Ala Pro Ala Lys Ile Ile Leu Phe
1               5                   10                  15

Gly Glu His Ser Val Val Tyr Gly Lys Pro Ala Ile Ala Ser Ala Ile
                20                  25                  30

Asp Leu Arg Thr Tyr Val Arg Ala Glu Phe Asn Asp Ser Gly Asn Ile
            35                  40                  45

Lys Ile Glu Ala His Asp Ile Lys Thr Pro Gly Leu Ile Val Ser Phe
50                  55                  60

Ser Glu Asp Lys Ile Tyr Phe Glu Thr Asp Tyr Gly Lys Ala Ala Glu
65                  70                  75                  80

Val Leu Ser Tyr Val Arg His Ala Ile Glu Leu Val Leu Glu Glu Ala
                85                  90                  95

Asp Lys Arg Thr Gly Val Ser Val Ser Ile Thr Ser Gln Ile Pro Val
            100                 105                 110

Gly Ala Gly Leu Gly Ser Ser Ala Ala Val Ala Val Ala Thr Ile Gly
        115                 120                 125

Ala Val Ser Lys Leu Leu Asp Leu Glu Leu Ser Lys Glu Glu Ile Ala
130                 135                 140

Lys Met Gly His Lys Val Glu Leu Leu Val Gln Gly Ala Ser Ser Gly
145                 150                 155                 160

Ile Asp Pro Thr Val Ser Ala Ile Gly Gly Phe Leu Tyr Tyr Lys Gln
                165                 170                 175

Gly Glu Phe Glu His Leu Pro Phe Val Glu Leu Pro Ile Val Val Gly
            180                 185                 190

Tyr Thr Gly Ser Ser Gly Ser Thr Lys Glu Leu Val Ala Met Val Arg
        195                 200                 205

Arg Arg Tyr Glu Glu Met Pro Glu Leu Ile Glu Pro Ile Leu Glu Ser
210                 215                 220

Met Gly Lys Leu Val Asp Lys Ala Lys Glu Val Ile Ile Ser Lys Leu
225                 230                 235                 240

Asp Glu Glu Glu Lys Phe Leu Lys Leu Gly Glu Leu Met Asn Ile Asn
                245                 250                 255

His Gly Leu Leu Asp Ala Leu Gly Val Ser Thr Lys Lys Leu Ser Glu
            260                 265                 270

Leu Val Tyr Ala Ala Arg Thr Ala Gly Ala Ile Gly Ala Lys Leu Thr
        275                 280                 285

Gly Ala Gly Gly Gly Gly Cys Met Tyr Ala Leu Ala Pro Gly Lys Gln
290                 295                 300

Arg Glu Val Ala Thr Ala Ile Lys Ile Ala Gly Gly Thr Pro Met Ile
305                 310                 315                 320

Thr Arg Ile Ser Lys Glu Gly Leu Arg Ile Glu Val Arg Glu
                325                 330                 335
```

<210> SEQ ID NO 9
<211> LENGTH: 335
<212> TYPE: PRT
<213> ORGANISM: Pyrococcus horikoshii

<400> SEQUENCE: 9

```
Met Val Lys Tyr Val Leu Ala Ser Ala Pro Ala Lys Val Ile Leu Phe
1               5                   10                  15
```

-continued

Gly Glu His Ser Val Val Tyr Gly Lys Pro Ala Ile Ala Ser Ala Ile
            20                  25                  30

Glu Leu Arg Thr Tyr Val Arg Ala Gln Phe Asn Asp Ser Gly Asn Ile
        35                  40                  45

Lys Ile Glu Ala His Asp Ile Lys Thr Pro Gly Leu Ile Val Ser Phe
    50                  55                  60

Ser Glu Asp Lys Ile Tyr Phe Glu Thr Asp Tyr Gly Lys Ala Ala Glu
65                  70                  75                  80

Val Leu Ser Tyr Val Arg Tyr Ala Ile Glu Leu Ala Leu Glu Glu Ser
                85                  90                  95

Asp Lys Arg Val Gly Ile Asp Val Ser Ile Thr Ser Gln Ile Pro Val
            100                 105                 110

Gly Ala Gly Leu Gly Ser Ser Ala Ala Val Ala Val Ala Thr Ile Gly
        115                 120                 125

Ala Val Ser Arg Leu Leu Gly Leu Glu Leu Ser Lys Glu Glu Ile Ala
    130                 135                 140

Lys Leu Gly His Lys Val Glu Leu Leu Val Gln Gly Ala Ser Ser Gly
145                 150                 155                 160

Ile Asp Pro Thr Val Ser Ala Val Gly Gly Phe Leu Tyr Tyr Lys Gln
                165                 170                 175

Gly Lys Phe Glu Pro Leu Pro Phe Met Glu Leu Pro Ile Val Val Gly
            180                 185                 190

Tyr Thr Gly Ser Thr Gly Ser Thr Lys Glu Leu Val Ala Met Val Arg
        195                 200                 205

Lys Arg Tyr Glu Glu Met Pro Glu Leu Val Glu Pro Ile Leu Glu Ala
    210                 215                 220

Met Gly Lys Leu Val Asp Lys Ala Lys Glu Ile Ile Leu Ser Lys Leu
225                 230                 235                 240

Asp Glu Glu Glu Lys Leu Thr Lys Leu Gly Glu Leu Met Asn Ile Asn
                245                 250                 255

His Gly Leu Leu Asp Ala Leu Gly Val Ser Thr Lys Lys Leu Gly Glu
            260                 265                 270

Leu Val Tyr Ala Ala Arg Thr Ala Gly Ala Ile Gly Ala Lys Leu Thr
        275                 280                 285

Gly Ala Gly Gly Gly Gly Cys Met Tyr Ala Leu Ala Pro Gly Arg Gln
    290                 295                 300

Arg Glu Val Ala Thr Ala Ile Lys Ile Ala Gly Gly Ile Pro Met Ile
305                 310                 315                 320

Thr Arg Val Ser Arg Glu Gly Leu Arg Ile Glu Glu Val Ser Arg
                325                 330                 335

<210> SEQ ID NO 10
<211> LENGTH: 334
<212> TYPE: PRT
<213> ORGANISM: Pyrococcus furiosus

<400> SEQUENCE: 10

Met Lys Val Ile Ala Ser Ala Pro Ala Lys Val Ile Leu Phe Gly Glu
1               5                   10                  15

His Ser Val Val Tyr Gly Lys Pro Ala Ile Ala Ala Ile Asp Leu
            20                  25                  30

Arg Thr Phe Val Glu Ala Glu Leu Ile Arg Glu Lys Ile Arg Ile
        35                  40                  45

Glu Ala His Asp Ile Lys Val Pro Gly Leu Thr Val Ser Phe Ser Glu
    50                  55                  60

-continued

```
Asn Glu Ile Tyr Phe Glu Thr Asp Tyr Gly Lys Ala Ala Glu Val Leu
 65                  70                  75                  80

Ser Tyr Val Arg Glu Ala Ile Asn Leu Val Leu Glu Glu Ala Asp Lys
             85                  90                  95

Lys Asn Val Gly Ile Lys Val Ser Ile Thr Ser Gln Ile Pro Val Gly
            100                 105                 110

Ala Gly Leu Gly Ser Ser Ala Ala Val Ala Val Ala Thr Ile Gly Ala
            115                 120                 125

Val Ser Lys Leu Leu Gly Leu Glu Leu Ser Lys Glu Glu Ile Ala Lys
    130                 135                 140

Met Gly His Lys Thr Glu Leu Leu Val Gln Gly Ala Ser Ser Gly Ile
145                 150                 155                 160

Asp Pro Thr Val Ser Ala Ile Gly Gly Phe Ile Phe Tyr Glu Lys Gly
                165                 170                 175

Lys Phe Glu His Leu Pro Phe Met Glu Leu Pro Ile Val Val Gly Tyr
            180                 185                 190

Thr Gly Ser Ser Gly Pro Thr Lys Glu Leu Val Ala Met Val Arg Lys
        195                 200                 205

Arg Tyr Glu Glu Met Pro Glu Leu Ile Val Pro Ile Leu Glu Ala Met
    210                 215                 220

Gly Lys Val Val Glu Lys Ala Lys Asp Val Ile Leu Ser Asn Val Asp
225                 230                 235                 240

Lys Glu Glu Lys Phe Glu Arg Leu Gly Val Leu Met Asn Ile Asn His
                245                 250                 255

Gly Leu Leu Asp Ala Leu Gly Val Ser Thr Lys Lys Leu Ser Glu Leu
            260                 265                 270

Val Tyr Ala Ala Arg Val Ala Gly Ala Leu Gly Ala Lys Ile Thr Gly
        275                 280                 285

Ala Gly Gly Gly Gly Cys Met Tyr Ala Leu Ala Pro Asn Lys Gln Arg
    290                 295                 300

Glu Val Ala Thr Ala Ile Arg Ile Ala Gly Gly Thr Pro Met Ile Thr
305                 310                 315                 320

Glu Ile Ser Arg Glu Gly Leu Lys Ile Glu Glu Val Ile Lys
                325                 330

<210> SEQ ID NO 11
<211> LENGTH: 303
<212> TYPE: PRT
<213> ORGANISM: Methanobacterium thermoautotrophicum

<400> SEQUENCE: 11

Met Lys Ser Ser Ala Ser Ala Pro Ala Lys Ala Ile Leu Phe Gly Glu
  1               5                  10                  15

His Ala Val Val Tyr Ser Lys Pro Ala Ile Ala Ala Ile Asp Arg
             20                  25                  30

Arg Val Thr Val Thr Val Ser Glu Ser Ser Thr His Val Thr Ile
         35                  40                  45

Pro Ser Leu Gly Ile Arg His Ser Ser Glu Arg Pro Ser Gly Gly Ile
     50                  55                  60

Leu Asp Tyr Ile Gly Arg Cys Leu Glu Leu Tyr His Asp Ala Ser Pro
 65                  70                  75                  80

Leu Asp Ile Arg Val Glu Met Glu Ile Pro Ala Gly Ser Gly Leu Gly
             85                  90                  95

Ser Ser Ala Ala Leu Thr Val Ala Leu Ile Gly Ala Leu Asp Arg Tyr
```

-continued

```
                    100                 105                 110
His Gly Arg Asp His Gly Pro Gly Glu Thr Ala Ala Arg Ala His Arg
            115                 120                 125

Val Glu Val Asp Val Gln Gly Ala Ala Ser Pro Leu Asp Thr Ala Ile
        130                 135                 140

Ser Thr Tyr Gly Gly Leu Val Tyr Leu Asp Ser Gln Arg Arg Val Arg
145                 150                 155                 160

Gln Phe Glu Ala Asp Leu Gly Asp Leu Val Ile Ala His Leu Asp Tyr
                165                 170                 175

Ser Gly Glu Thr Ala Arg Met Val Ala Gly Val Ala Glu Arg Phe Arg
            180                 185                 190

Arg Phe Pro Asp Ile Met Gly Arg Ile Met Asp Thr Val Glu Ser Ile
        195                 200                 205

Thr Asn Thr Ala Tyr Arg Glu Leu Leu Arg Asn Asn Thr Glu Pro Leu
210                 215                 220

Gly Glu Leu Met Asn Leu Asn Gln Gly Leu Leu Asp Ser Met Gly Val
225                 230                 235                 240

Ser Thr Arg Glu Leu Ser Met Met Val Tyr Glu Ala Arg Asn Ala Gly
                245                 250                 255

Ala Ala Gly Ser Lys Ile Thr Gly Ala Gly Gly Gly Ser Ile Ile
            260                 265                 270

Ala His Cys Pro Gly Cys Val Asp Asp Val Val Thr Ala Leu Asn Arg
        275                 280                 285

Asn Trp Lys Ala Met Arg Ala Glu Phe Ser Val Lys Gly Leu Ile
        290                 295                 300

<210> SEQ ID NO 12
<211> LENGTH: 284
<212> TYPE: PRT
<213> ORGANISM: Archaeoglobus fulgidus

<400> SEQUENCE: 12

Met Ile Ala Ser Ala Pro Gly Lys Ile Ile Leu Phe Gly Glu His Ala
1               5                   10                  15

Val Val Tyr Gly Arg His Ala Val Val Ser Ala Ile Asn Leu Arg Cys
            20                  25                  30

Arg Val Ser Val Arg Lys Ser Asp Arg Phe Leu Ile Arg Ser Ser Leu
        35                  40                  45

Gly Glu Ser Gly Leu Asp Tyr Gln Arg His Pro Tyr Val Val Gln Ala
    50                  55                  60

Val Lys Arg Phe Gly Glu Leu Arg Asn Ile Pro Gly Ala Glu Ile Glu
65                  70                  75                  80

Ile Glu Ser Glu Ile Pro Ile Gly Ser Gly Leu Gly Ser Ser Ala Ala
                85                  90                  95

Val Ile Val Ala Thr Ile Ala Ala Leu Asn Ala Glu Phe Asp Gly Asp
            100                 105                 110

Met Asp Lys Glu Ala Ile Phe Gln Met Ala Lys Gln Val Glu Ile Asp
        115                 120                 125

Val Gln Gly Arg Ala Ser Gly Ile Asp Pro Phe Ile Ser Thr Phe Gly
    130                 135                 140

Gly Ser Trp Leu Phe Pro Glu Arg Arg Lys Val Glu Met Pro Phe Lys
145                 150                 155                 160

Phe Phe Val Ile Asn Phe Gly Ser Arg Ser Thr Ala Glu Met Val Ala
                165                 170                 175
```

```
Lys Val Ala Glu Leu Arg Glu Arg His Pro Glu Val Val Asp Lys Ile
            180                 185                 190

Phe Asp Ala Ile Asp Ala Ile Ser Leu Glu Ala Ser Asp Val Gly Ser
        195                 200                 205

Ala Glu Arg Leu Glu Leu Ile Ala Ile Asn Gln Ser Leu Leu Arg
    210                 215                 220

Ala Ile Gly Val Ser Asn Pro Glu Ile Asp Arg Thr Ile Ala Glu Leu
225                 230                 235                 240

Glu Arg Met Gly Leu Asn Ala Lys Ile Thr Gly Ala Gly Gly Gly
            245                 250                 255

Cys Ile Phe Gly Leu Phe Lys Gly Glu Lys Pro Lys Gly Ser Phe Ile
            260                 265                 270

Val Glu Pro Glu Lys Glu Gly Val Arg Ile Glu Glu
        275                 280

<210> SEQ ID NO 13
<211> LENGTH: 312
<212> TYPE: PRT
<213> ORGANISM: Methanococcus jannaschii

<400> SEQUENCE: 13

Met Ile Ile Glu Thr Pro Ser Lys Val Ile Leu Phe Gly Glu His Ala
1               5                   10                  15

Val Val Tyr Gly Tyr Arg Ala Ile Ser Met Ala Ile Asp Leu Thr Ser
            20                  25                  30

Thr Ile Glu Ile Lys Glu Thr Gln Glu Asp Glu Ile Ile Leu Asn Leu
        35                  40                  45

Asn Asp Leu Asn Lys Ser Leu Gly Leu Asn Leu Asn Glu Ile Lys Asn
    50                  55                  60

Ile Asn Pro Asn Asn Phe Gly Asp Phe Lys Tyr Cys Leu Cys Ala Ile
65                  70                  75                  80

Lys Asn Thr Leu Asp Tyr Leu Asn Ile Glu Pro Lys Thr Gly Phe Lys
                85                  90                  95

Ile Asn Ile Ser Ser Lys Ile Pro Ile Ser Cys Gly Leu Gly Ser Ser
            100                 105                 110

Ala Ser Ile Thr Ile Gly Thr Ile Lys Ala Val Ser Gly Phe Tyr Asn
        115                 120                 125

Lys Glu Leu Lys Asp Asp Glu Ile Ala Lys Leu Gly Tyr Met Val Glu
    130                 135                 140

Lys Glu Ile Gln Gly Lys Ala Ser Ile Thr Asp Thr Ser Thr Ile Thr
145                 150                 155                 160

Tyr Lys Gly Ile Leu Glu Ile Lys Asn Asn Lys Phe Arg Lys Ile Lys
                165                 170                 175

Gly Glu Phe Glu Glu Phe Leu Lys Asn Cys Lys Phe Leu Ile Val Tyr
            180                 185                 190

Ala Glu Lys Arg Lys Lys Thr Ala Glu Leu Val Asn Glu Val Ala
        195                 200                 205

Lys Ile Glu Asn Lys Asp Glu Ile Phe Lys Glu Ile Asp Lys Val Ile
    210                 215                 220

Asp Glu Ala Leu Lys Ile Lys Asn Lys Glu Asp Phe Gly Lys Leu Met
225                 230                 235                 240

Thr Lys Asn His Glu Leu Leu Lys Lys Leu Asn Ile Ser Thr Pro Lys
                245                 250                 255

Leu Asp Arg Ile Val Asp Ile Gly Asn Arg Phe Gly Phe Gly Ala Lys
            260                 265                 270
```

```
Leu Thr Gly Ala Gly Gly Gly Cys Val Ile Ile Leu Val Asn Glu
        275                 280                 285

Glu Lys Glu Lys Glu Leu Leu Lys Glu Leu Asn Lys Glu Asp Val Arg
    290                 295                 300

Ile Phe Asn Cys Arg Met Met Asn
305                 310

<210> SEQ ID NO 14
<211> LENGTH: 324
<212> TYPE: PRT
<213> ORGANISM: Aeropyrum pernix

<400> SEQUENCE: 14

Met Arg Arg Ala Ala Arg Ala Ser Ala Pro Gly Lys Val Ile Ile Val
1               5                   10                  15

Gly Glu His Phe Val Val Arg Gly Ser Leu Ala Ile Val Ala Ala Ile
            20                  25                  30

Gly Arg Arg Leu Arg Val Thr Val Arg Ser Gly Gly Lys Gly Ile Val
        35                  40                  45

Leu Glu Ser Ser Met Leu Gly Arg His Ser Ala Pro Leu Pro Gly Gln
    50                  55                  60

Gly Ala Ala Ala Lys Val Ser Pro Val Leu Glu Pro Tyr Ile Ala Val
65                  70                  75                  80

Leu Arg Ser Leu Ala Ala Arg Gly Tyr Ser Val Val Pro His Thr Ile
                85                  90                  95

Leu Val Glu Ser Gly Ile Pro Pro Arg Ala Gly Leu Gly Ser Ser Ala
            100                 105                 110

Ala Ser Met Val Ala Tyr Ala Leu Ser Tyr Ser Ala Met His Gly Asp
        115                 120                 125

Pro Leu Ser Ala Glu Asp Leu Tyr Ser Val Ala Met Glu Gly Glu Lys
    130                 135                 140

Ile Ala His Gly Lys Pro Ser Gly Val Asp Val Thr Ile Ala Val Arg
145                 150                 155                 160

Gly Gly Val Leu Ala Tyr Arg Arg Gly Glu Asn Pro Val Asp Ile Arg
                165                 170                 175

Pro Gly Leu Thr Gly Val Thr Leu Leu Val Ala Asp Thr Gly Val Glu
            180                 185                 190

Arg Arg Thr Arg Asp Val Val Glu His Val Leu Ser Ile Ala Asp Ala
        195                 200                 205

Leu Gly Glu Ala Ser Thr Tyr Ile Tyr Arg Ala Ala Asp Leu Ile Ala
    210                 215                 220

Arg Glu Ala Leu His Ala Ile Glu Lys Gly Asp Ala Glu Arg Leu Gly
225                 230                 235                 240

Leu Ile Met Asn Ala Ala Gln Gly Leu Leu Ser Ser Leu Gly Ala Ser
                245                 250                 255

Ser Leu Glu Ile Glu Thr Leu Val Tyr Arg Met Arg Ser Ala Gly Ala
            260                 265                 270

Leu Gly Ala Lys Leu Thr Gly Ala Gly Trp Gly Gly Cys Val Ile Gly
        275                 280                 285

Leu Phe Lys Glu Gly Glu Val Glu Arg Gly Leu Glu Ser Val Val Glu
    290                 295                 300

Ser Ser Ser Gln Ala Phe Thr Ala Ser Ile Ala Glu Glu Gly Ala Arg
305                 310                 315                 320

Leu Glu Glu Phe
```

<210> SEQ ID NO 15
<211> LENGTH: 387
<212> TYPE: PRT
<213> ORGANISM: Artificial Sequence
<220> FEATURE:
<223> OTHER INFORMATION: His6-Paracoccus zeaxanthinifaciens

<400> SEQUENCE: 15

```
Met Arg Gly Ser His His His His His His Ser Thr Gly Arg Pro Glu
1               5                   10                  15

Ala Gly Ala His Ala Pro Gly Lys Leu Ile Leu Ser Gly Glu His Ser
            20                  25                  30

Val Leu Tyr Gly Ala Pro Ala Leu Ala Met Ala Ile Ala Arg Tyr Thr
        35                  40                  45

Glu Val Trp Phe Thr Pro Leu Gly Ile Gly Glu Gly Ile Arg Thr Thr
    50                  55                  60

Phe Ala Asn Leu Ser Gly Gly Ala Thr Tyr Ser Leu Lys Leu Leu Ser
65                  70                  75                  80

Gly Phe Lys Ser Arg Leu Asp Arg Arg Phe Glu Gln Phe Leu Asn Gly
                85                  90                  95

Asp Leu Lys Val His Lys Val Leu Thr His Pro Asp Asp Leu Ala Val
            100                 105                 110

Tyr Ala Leu Ala Ser Leu Leu His Asp Lys Pro Pro Gly Thr Ala Ala
        115                 120                 125

Met Pro Gly Ile Gly Ala Met His His Leu Pro Arg Pro Gly Glu Leu
    130                 135                 140

Gly Ser Arg Thr Glu Leu Pro Ile Gly Ala Gly Met Gly Ser Ser Ala
145                 150                 155                 160

Ala Ile Val Ala Ala Thr Thr Val Leu Phe Glu Thr Leu Leu Asp Arg
                165                 170                 175

Pro Lys Thr Pro Glu Gln Arg Phe Asp Arg Val Arg Phe Cys Glu Arg
            180                 185                 190

Leu Lys His Gly Lys Ala Gly Pro Ile Asp Ala Ala Ser Val Val Arg
        195                 200                 205

Gly Gly Leu Val Arg Val Gly Gly Asn Gly Pro Gly Ser Ile Ser Ser
    210                 215                 220

Phe Asp Leu Pro Glu Asp His Asp Leu Val Ala Gly Arg Gly Trp Tyr
225                 230                 235                 240

Trp Val Leu His Gly Arg Pro Val Ser Gly Thr Gly Glu Cys Val Ser
                245                 250                 255

Ala Val Ala Ala Ala His Gly Arg Asp Ala Ala Leu Trp Asp Ala Phe
            260                 265                 270

Ala Val Cys Thr Arg Ala Leu Glu Ala Ala Leu Ser Gly Gly Ser
        275                 280                 285

Pro Asp Ala Ala Ile Thr Glu Asn Gln Arg Leu Leu Glu Arg Ile Gly
    290                 295                 300

Val Val Pro Ala Ala Thr Gln Ala Leu Val Ala Gln Ile Glu Glu Ala
305                 310                 315                 320

Gly Gly Ala Ala Lys Ile Cys Gly Ala Gly Ser Val Arg Gly Asp His
                325                 330                 335

Gly Gly Ala Val Leu Val Arg Ile Asp Asp Ala Gln Ala Met Ala Ser
            340                 345                 350

Val Met Ala Arg His Pro Asp Leu Asp Trp Ala Pro Leu Arg Met Ser
        355                 360                 365
```

-continued

```
Arg Thr Gly Ala Ala Pro Gly Pro Ala Pro Arg Ala Gln Pro Leu Pro
    370                 375                 380

Gly Gln Gly
385

<210> SEQ ID NO 16
<211> LENGTH: 1137
<212> TYPE: DNA
<213> ORGANISM: Paracoccus zeaxanthinifaciens

<400> SEQUENCE: 16
atgtcgaccg gcaggcctga agcaggcgcc catgccccgg gcaagctgat cctgtccggg      60
gaacattccg tgctctatgg tgcgcccgcg cttgccatgg ccatcgcccg ctataccgag     120
gtgtggttca cgccgcttgg cattggcgag gggatacgca cgacattcgc caatctctcg     180
ggcggggcga cctattcgct gaagctgctg tcggggttca gtcgcggct ggaccgccgg      240 ttcgagcagt tcctgaacgg cgacctaaag gtgcacaagg tcctgaccca tcccgacgat     300
ctggcggtct atgcgctggc gtcgcttctg cacgacaagc cgccggggac cgccgcgatg     360
ccgggcatcg gcgcgatgca ccacctgccg cgaccgggtg agctgggcag ccggacggag     420
ctgcccatcg gcgcgggcat ggggtcgtct gcggccatcg tcgcggccac cacggtcctg     480
ttcgagacgc tgctggaccg gcccaagacg cccgaacagc gcttcgaccg cgtccgcttc     540
tgcgagcggt tgaagcacgg caaggccggt cccatcgacg cggccagcgt cgtgcgcggc     600
gggcttgtcc gcgtgggcgg gaacgggccg ggttcgatca gcagcttcga tttgcccgag     660
gatcacgacc ttgtcgcggg acgcggctgg tactgggtac tgcacgggcg ccccgtcagc     720
gggaccggcg aatgcgtcag cgcggtcgcg gcggcgcatg gtcgcgatgc ggcgctgtgg     780
gacgccttcg cagtctgcac ccgcgcgttg gaggccgcgc tgctgtctgg gggcagcccc     840
gacgccgcca tcaccgagaa ccagcgcctg ctggaacgca tcggcgtcgt gccggcagcg     900
acgcaggccc tcgtggccca gatcgaggag gcgggtggcg cggccaagat ctgcggcgca     960
ggttccgtgc ggggcgatca cggcggggcg gtcctcgtgc ggattgacga cgcgcaggcg    1020
atggcttcgg tcatggcgcg ccatcccgac ctcgactggg cgcccctgcg catgtcgcgc    1080 acggggcgg cacccggccc cgcgccgcgt gcgcaaccgc tgccggggca gggctga       1137

<210> SEQ ID NO 17
<211> LENGTH: 1191
<212> TYPE: DNA
<213> ORGANISM: homo sapiens

<400> SEQUENCE: 17
atgttgtcag aagtcctact ggtgtctgct ccggggaaag tcatccttca tggagaacat      60
gccgtggtac atggcaaggt agcactggct gtatccttga acttgagaac attcctccgg     120
cttcaacccc acagcaatgg gaaagtggac ctcagcttac ccaacattgg tatcaagcgg     180
gcctgggatg tggccaggct tcagtcactg gacacaagct ttctggagca aggtgatgtc     240
acaacaccca cctcagagca agtggagaag ctaaaggagg ttgcaggctt gcctgacgac     300
tgtgctgtca ccgagcgcct ggctgtgctg gccttctctt acttataccrt gtccatctgc     360 cggaagcaga gggccctgcc gagcctggat atcgtagtgt ggtcggagct gccccccggg     420
gcgggcttgg gctccagcgc cgcctactcg gtgtgtctgg cagcagccct cctgactgtg     480
tgcgaggaga tcccaaaccc gctgaaggac ggggattgcg tcaacaggtg gaccaaggag     540
```

-continued

```
gatttggagc taattaacaa gtgggccttc aagggggaga gaatgattca cggaaccccc      600
tccggagtgg acaatgctgt cagcacctgg ggaggagccc tccgatacca tcaagggaag      660
atttcatcct taaagaggtc gccagctctc cagatcctgc tgaccaacac caaagtccct      720
cgcaatacca gggcccttgt ggctggcgtc agaaacaggc tgctcaagtt cccagagatc      780
gtggcccccc tcctgacctc aatagatgcc atctccctgg agtgtgagcg cgtgctggga      840
gagatggggg aagcccagc cccggagcag tacctcgtgc tggaagagct cattgacatg      900
aaccagcacc atctgaatgc cctcggcgtg ggccacgcct ctctggacca gctctgccag      960
gtgaccaggg cccgcggact tcacagcaag ctgactggcg caggcggtgg tggctgtggc     1020
atcacactcc tcaagccagg gctggagcag ccagaagtgg aggccacgaa gcaggccctg     1080
accagctgtg gctttgactg cttggaaacc agcatcggtg cccccggcgt ctccatccac     1140
tcagccacct ccctggacag ccgagtccag caagccctgg atggcctctg a              1191
```

<210> SEQ ID NO 18
<211> LENGTH: 1188
<212> TYPE: DNA
<213> ORGANISM: mouse

<400> SEQUENCE: 18

```
atgttgtcag aagccctgct ggtgtccgcc ccggggaagg tcatcctcca tggagaacac       60
gctgtggtcc atggcaaggt cgctctggca gcggccttga acttgagaac tttcctcctg      120
ctgcgaccgc agagcaatgg gaaagtgagc gtcaatttac ccaacatcgg tattaagcag      180
gtgtgggatg tgggcatgct tcagcgactg gacacgagct ttcttgagca aggtgatgtc      240
tcggtaccca ccttggagca actggagaag ctaaagaaga tgggggacct ccccagagac      300
cgtgcaggca atgaaggcat ggctctgctt gcctttctct acctgtacct ggcaatctgc      360
cggaagcaga ggacactccc gagcctggac atggtggtgt ggtcggaact tcccccccggg     420 gcaggcttgg gctccagcgc cgcctactct gtgtgtctgg cagccgccct cctgactgcc      480
tgtgaggagg tctccaaccc gctcaaggac ggggtctccg tcagcaggtg gcccgaggaa      540
gatctgaagt caatcaacaa gtgggccttc aagggggaga gagtgatcca tgggaaccct      600
tctggtgtgg acaatgccgt cagcacctgg ggcggagccc tgcgcttcca gcaagggacg      660
atgtcttcct tgaagagcct cccgtctctg cagatcctgc tcaccaacac caaggtcccg      720
cggagtacca aggcccttgt ggctgctgtc agaagcaggc tgaccaagtt ccctgagatt      780
gtggccccgc tgctgacctc cattgacgca atatccctgg agtgtgagcg cgtgctaggg      840
gagatggtgg cagctccagt tccggaacag tacctcgtac tagaagagct gatagacatg      900
aaccagcacc atctgaatgc tctcggggtg gccacaact ccctgaccca gctctgccaa       960
gtaacggcag cacacggact gcacagcaag ctgacgggcg ctggcggtgg cggctgtggc     1020
atcaccctcc tgaagccagg tctagagcaa gccacagtgg aggcagccaa gcaggccctg     1080
accagctgcg ggtttgactg ctgggagacc agcatcggcg cacccggagt ttccacacac     1140
tcagctgcag ctgtaggga cctgtccga caagccctgg gcctctga                   1188
```

<210> SEQ ID NO 19
<211> LENGTH: 1188
<212> TYPE: DNA
<213> ORGANISM: rat

<400> SEQUENCE: 19

```
atgttgtcag aagtcctgct ggtgtctgct ccagggaaag tcattctcca tggagaacat       60
```

-continued

```
gctgtggtcc atggcaaggt agctctggcg gtggccttga acttgagaac atttctcgtg    120
ctgcgaccgc agagcaatgg gaaagtgagc ctcaatttac caaacgtcgg tattaagcag    180
gtctgggatg tggccacact tcagctgctg gacacaggct ttcttgagca aggcgatgtc    240
ccggcaccca ccttggagca actggagaag ctgaagaagg tggcgggcct ccccgagac     300 tgtgtaggca acgaaggcct gtctctgctt gcctttctgt acctgtacct ggctatctgc    360
cggaaacaga ggacactccc aagcctggac atcatggtgt ggtcggaact gccccctggg    420
gcgggcttgg gctccagtgc agcctactcg gtgtgtgtgg cagccgccct cctgactgcc    480
tgtgaggagg tcaccaaccc gctcaaggac aggggctcca ttggcagttg gcccgaggag    540
gacctgaagt caattaacaa gtgggcctac gaggggagag agtgatccat gggaaccccc    600
tctggcgtgg acaattccgt cagcacctgg ggaggagccc tgcgctacca gcaagggaag    660
atgtcatcct tgaagaggct cccagctctg cagatcctgc tcaccaacac caaggtccca    720
cgaagcacca aggccctcgt ggctggcgtc agaagcaggc taatcaagtt ccctgagatc    780
atggccccgc tcctgacatc aattgacgca atctccctgg agtgtgagcg cgtgctggga    840
gagatggcgg ccgcaccagt cccagaacag taccttgtcc tagaagagct aatggacatg    900
aaccagcacc atctgaatgc ccttggtgtg ggccacgcct ccctggacca gctctgtcag    960
gtaacagcag cacatggact gcacagcaag ctgactggcg caggcggcgg cggctgtggc    1020 atcacccttcc tgaagccagg tctagagcga gcaaaagtgg aggccgccaa gcaggccctg    1080
accggctgcg ggtttgactg ctgggagacc agcattgagg cgcctgggt ctccatgcac     1140 tcagccacct ccatagagga ccctgtccga caagccctgg gcctctga                 1188
```

<210> SEQ ID NO 20
<211> LENGTH: 1137
<212> TYPE: DNA
<213> ORGANISM: Arabidopsis thaliana

<400> SEQUENCE: 20

```
atggaagtga agctagagc tcctgggaag atcatacttg caggggaaca cgctgttgtt     60
catggatcca ccgctgtagc tgccgccatt gatctctaca cttacgttac tctccgcttt    120
cctcttccat cagctgagaa caatgatagg cttacacttc agctcaagga catttccttg    180
gagttttcat ggtccttagc cagaatcaaa gaagcgattc cttatgattc aagcactctc    240
tgccgttcta cgccggcttc atgttcagag gagacccta aatcaattgc agttttggtt    300
gaagagcaaa atcttccaaa ggaaaagatg tggctctcct ctgggatctc cacgtttctc    360
tggttataca ccagaattat agggttcaat ccggctacag tagtcattaa ctctgagctt    420
ccatacgggt ctggcctcgg ttcatcagca gctttatgtg tagctctcac agctgctctc    480
cttgcttctt ctatttcaga gaaaacccgt ggtaacggtt ggtcatctct cgatgaaacc    540
aatcttgagt tgctaaataa atgggctttc gaaggcgaaa agatcatcca tgggaaacct    600
tctgggatag acaacaccgt cagtgcatac ggcaacatga tcaagttctg ctcaggcgag    660
ataactcggt tacaatccaa catgcctctg agaatgctaa ttaccaacac tagagttggg    720
cgaaacacaa aagctctggt ctctggtgtg tcacagagag cggtaagaca tcctgatgcg    780
atgaagtcag tgttcaacgc cgtggattct ataagcaaag agctcgctgc gatcattcag    840
tctaaagacg agacctcagt tacagaaaaa gaagagagaa taaaagaact catggagatg    900
aaccaaggtc tgctcctgtc aatgggggtt agccacagct caatcgaggc tgtgattcta    960
```

-continued

| | |
|---|---|
| accacggtca agcacaagct tgtctccaaa cttacaggag ctggtggcgg cggctgcgtc | 1020 |
| ctcactctat taccaaccgg gacggtggtg gacaaagtgg tggaggagct cgagtccagc | 1080 |
| ggttttcagt gtttcacggc attgattggt ggtaacggag ctcagatttg ctattga | 1137 |

<210> SEQ ID NO 21
<211> LENGTH: 1332
<212> TYPE: DNA
<213> ORGANISM: Saccharomyces cerevisiae

<400> SEQUENCE: 21

| | |
|---|---|
| atgtcattac cgttcttaac ttctgcaccg ggaaaggtta ttattttggt tgaacactct | 60 |
| gctgtgtaca acaagcctgc cgtcgctgct agtgtgtctg cgttgagaac ctacctgcta | 120 |
| ataagcgagt catctgcacc agatactatt gaattggact ccccggacat tagctttaat | 180 |
| cataagtggt ccatcaatga tttcaatgcc atcaccgagg atcaagtaaa ctcccaaaaa | 240 |
| ttggccaagg ctcaacaagc caccgatggc ttgtctcagg aactcgttag tcttttggat | 300 |
| ccgttgttag ctcaactatc cgaatccttc cactaccatg cagcgttttg tttcctgtat | 360 |
| atgtttgttt gcctatgccc ccatgccaag aatattaagt tttctttaaa gtctacttta | 420 |
| cccatcggtg ctgggttggg ctcaagcgcc tctatttctg tatcactggc cttagctatg | 480 |
| gcctacttgg gggggttaat aggatctaat gacttggaaa agctgtcaga aaacgataag | 540 |
| catatagtga atcaatgggc cttcataggt gaaaagtgta ttcacggtac cccttcagga | 600 |
| atagataacg ctgtggccac ttatggtaat gccctgctat ttgaaaaaga ctcacataat | 660 |
| ggaacaataa acacaaacaa ttttaagttc ttagatgatt cccagccat tccaatgatc | 720 |
| ctaacctata ctagaattcc aaggtctaca aaagatcttg ttgctcgcgt tcgtgtgttg | 780 |
| gtcaccgaga atttcctga agttatgaag ccaattctag atgccatggg tgaatgtgcc | 840 |
| ctacaaggct tagagatcat gactaagtta agtaaatgta aaggcaccga tgacgaggct | 900 |
| gtagaaacta ataatgaact gtatgaacaa ctattggaat tgataagaat aaatcatgga | 960 |
| ctgcttgtct caatcggtgt ttctcatcct ggattagaac ttattaaaaa tctgagcgat | 1020 |
| gatttgagaa ttggctccac aaaacttacc ggtgctggtg gcggcggttg ctctttgact | 1080 |
| ttgttacgaa gagacattac tcaagagcaa attgacagct tcaaaaagaa attgcaagat | 1140 |
| gattttagtt acgagacatt tgaaacagac ttgggtggga ctggctgctg tttgttaagc | 1200 |
| gcaaaaaatt tgaataaaga tcttaaaatc aaatccctag tattccaatt atttgaaaat | 1260 |
| aaaactacca caaagcaaca aattgacgat ctattattgc caggaaacac gaatttacca | 1320 |
| tggacttcat aa | 1332 |

<210> SEQ ID NO 22
<211> LENGTH: 1215
<212> TYPE: DNA
<213> ORGANISM: Schizosaccharomyces pombe

<400> SEQUENCE: 22

| | |
|---|---|
| atgtcaaaat cgcttattgt ttcgtcgcca ggaaaaacga ttttgtttgg ggaacatgcc | 60 |
| gttgtatatg gagctactgc gttagctgca gctgtatcgt tacggagtta ctgtaaatta | 120 |
| cagacgacta taacaatga atagtaatt gtgatgagtg atatagggac cgaacgccga | 180 |
| tggaatcttc aatcgctacc ttggcagcat gtaacagtgg aaaacgttca gcacccggca | 240 |
| tcatctccca atctggacct tttacaagga ttaggagagc tattaaaaaa tgaagaaaac | 300 |
| ggacttattc actcagcaat gctttgtacc ctttacttgt tcacgtcttt gtcttctcct | 360 |

```
tctcagggtt gtactttaac tattagctcc caagtacctt tgggtgctgg attaggtagt      420
agtgctacta tatcagttgt tgtcgctaca agtttactac tagcttttgg taatattgaa      480
cctcctagct caaattctct tcaaaacaac aaagcacttg cgttgataga ggcttggtct      540
tttctaggtg aatgctgtat tcatggaaca ccaagtggta ttgataatgc agtagcaaca      600
aatggaggac ttatcgcttt tcgtaaagct acagctcatc agagtgccat gaaagaattc      660
ttaaagccta agataccttt atctgttatg atcactgata ccaaacaacc aaaaagtact      720
aaaaaacttg tacaaggagt ttttgaactg aaggaaagac taccaactgt gattgactca      780
ataatagatg caatcgatgg catatcaaag tctgccgtcc tcgcattgac ttcggagagc      840
gataaaaact cctccgctaa aaagttagga gagtttattg ttcttaatca aaaactctta      900
gaatgcttgg gtgtatccca ttattccatt gatcgcgttt tacaagccac taagtcaatt      960
ggatggacga agcttacagg tgccggtggt ggaggttgta cgattacttt attaacacct     1020
gagtgcaaag aagaggaatt taagttatgt aaagaatcac tattagccca taaaaattct     1080
atttacgatg ttcaattagg tggacctggt gtttcagtgg taaccgactc agattcattt     1140
ttccctcaat atgagtctga ctttgatttt aaaaaattga atttactcag caaatttaat     1200
aaatattata tttaa                                                      1215

<210> SEQ ID NO 23
<211> LENGTH: 1008
<212> TYPE: DNA
<213> ORGANISM: Pyrococcus abyssi

<400> SEQUENCE: 23
atgccaaggt tagtgctggc gtcagctcca gcaaagataa tactcttcgg ggaacacagc       60
gttgtgtatg gaaagcctgc catagcatct gctattgact tgagaactta cgttagggcg      120
gagtttaatg attcgggaaa tataaagata gaagcccatg acataaaaac ccctgggcta      180
atagtttctt tttcagaaga caaaatttac ttcgagactg actatggaaa ggcagctgaa      240
gtgctgagtt acgttagaca cgccatagag ctcgtccttg aagaggctga taagaggact      300
ggggtcagcg tttcaataac gtctcaaatt ccagtaggtg ctggcctagg ttcttcagct      360
gccgtcgccg ttgctaccat cggtgccgtc tccaagttac ttgacctcga gcttagtaaa      420
gaggagatag ctaagatggg ccataaggtt gaactcctgg ttcagggagc ttcgagtggc      480
atagatccga cggtctcggc aataggaggg ttcttgtact ataagcaagg tgaatttgag      540
cacctaccat tcgtggagct tccaatagta gttggatata ccggctcaag tggctccaca      600
aaggaattag ttgcgatggt taggagaagg tacgaggaga tgcccgagtt aattgaaccc      660
attctagagt caatgggtaa gctcgtggat aaagctaagg aggtaataat atctaagctc      720
gatgaggagg aaaagttcct gaaattggga gagctcatga acataaatca tggccttctc      780
gatgccctag gtgtttcaac caaaaagcta agcgaactcg tctatgccgc tagaactgct      840
ggagcaattg gagccaagct aacgggggct ggggagggtg gatgcatgta cgctttagct      900
cctgggaagc agagggaggt tgctacggcc ataaagatag ctggcggaac tcccatgata      960
acgaggataa gcaaggaggg gcttagaata gaggaggtaa gggaatga                 1008

<210> SEQ ID NO 24
<211> LENGTH: 1008
<212> TYPE: DNA
<213> ORGANISM: Pyrococcus horikoshii
```

```
<400> SEQUENCE: 24
tcatcttgaa acctcctcta ttctcaatcc ttccctactt accctcgtta tcattggaat      60
tccaccagct atctttattg ccgtggcgac ttccctctgt ctcccagggg ccaaggcata     120
catacaccct ccaccaccag cacccgtaag ttttgcccca attgcaccag ccgttctagc     180
agcgtaaact aactcaccaa gcttcttcgt agacacccccc aaagcatcta aaagcccatg    240
atttatgttc attaactctc caagcttagt aagcttctcc tcttcatcga gctttgaaag    300
tattatctcc ttggccttat ccactaattt tcccattgcc tccaatatag gctccacaag    360
ttcgggcatt tcctcgtacc ttttccttac cattgccact aattctttag ttgaaccagt    420
agagccggtg taaccaacga ctatgggaag ctccatgaat gggagaggct caaactttcc    480
ttgcttataa tagaggaagc ctcccactgc agaaactgta ggatcaatgc cacttgaagc    540
tccctgcact agaagttcaa ctttatgccc aagctttgct atttcctcct tactcaattc    600
aaggccaagt aacctagaga ccgcaccaat tgtagcaact gcaaccgctg ctgaggaacc    660
caatccggcc ccaactggaa tttgagaggt tattgaaacg tcaataccaa ccctcttatc    720
agactcctcc agggcaagtt ctatggcata cctcacatag ctcaaaactt cagcggcctt    780
tccatagtct gtttcaaagt atatcttatc ctcggaaaac gagactatca atccaggagt    840
ttttatatca tgagcttcta tttttatatt acccgaatca ttgaattgag ctctaacata    900
tgttctaagt tctatagcag aagctatagc cggttttcca tagactacgc tatgttcccc    960
gaagagtatt acctttgcag gagctgaagc taaaacgtac ttaaccat                1008

<210> SEQ ID NO 25
<211> LENGTH: 1005
<212> TYPE: DNA
<213> ORGANISM: Pyrococcus furiosus

<400> SEQUENCE: 25
tcatttaatt acctcctcaa tttttaaccc ttctctgctg atttcagtta tcataggagt      60 tcccctgca attcttatag ctgtagcaac ttctctctgc ttgttcggtg ccaaggcata     120
catacaacct cctcccccag ccccagttat cttagctcct agggctcccg caaccctagc    180
cgcgtacact agttcactca acttttttagt tgaaacaccc aaagcatcta aaagaccgtg    240
attaatgttc atcaaaaccc caagcctttc aaattttttcc tccttatcaa catttgaaag    300
tattacatcc ttggctttct cgacaacttt tcccatagcc tctaatatgg gaacaatcaa    360
ctcgggcatc tcctcatatc ttttcctaac cattgcaact aactccttag ttggacctga    420
ggagcccgtg tatccaacaa ctattggaag ctccatgaag ggaaggtgtt caaatttacc    480
cttttcatag aatataaacc ccctattgc agagaccgtt gggtctatac cacttgacgc    540
accttgaaca gtaattcag tcttgtgacc catcttagct atttcctcct tacttagctc    600
aagtcctagt aactttgata cagccccaat tgtggctact gccacggcag cagaagagcc    660
caatccagca ccaactggaa tttgagaagt tatgctaacc ttaataccaa cattttttctt    720 atctgcctcc tctaaaacta aatttattgc ctctctaaca tagctcaaaa cttcagctgc    780
ttttccataa tctgtctcga aatatatctc attttcagaa aatgaaaccg taagtccagg    840
aactttaatg tcatgagctt caattcttat tttttctcc cgaattagct cagcctccac    900
aaaagttcgt aaatcaatgg cagcagctat cgctggcttt ccgtaaacta cgctatgctc    960
tccaaaaaga ataactttg cgggagctga ggctataact ttcat                  1005
```

<210> SEQ ID NO 26
<211> LENGTH: 912
<212> TYPE: DNA
<213> ORGANISM: Methanobacterium thermoautotrophicum

<400> SEQUENCE: 26

```
ttgaagtcgt cggcatccgc acctgccaag gccattcttt ttggtgaaca cgcagtggtc      60
tacagcaagc cggcaatagc agccgccata gaccgcaggg tgactgtaac cgtaagtgaa     120
tccagcagca cccatgtaac catcccctcc ctgggtatac gccacagttc agagagacca     180
tccggtggca tcctggacta catcgggagg tgcctcgagc tttaccatga cgcatcaccc     240
cttgacatca gggtggagat ggagataccc gccggttcag gcctaggttc atcggctgca     300
ctcaccgttg cactgatagg tgccctcgac aggtaccatg gaaggggatca tggacccggg     360
gagacagcag ccagggccca cagggtggag gttgatgtac agggagccgc cagcccccctt    420
gacacagcca tcagcaccta tggggccctt gtataccttg acagccagag gagggtgagg     480
cagtttgagg ccgacctggg ggaccttgta atagcacacc ttgactattc aggggaaaca     540
gccaggatgg ttgccggcgt agctgaaagg ttcaggagat cccggatat catggggagg     600
ataatggaca cagttgagtc cataaccaat acagcataca gggaacttct aaggaacaac     660
acagaacccc tgggggagct catgaacctc aaccaggggc tgctggactc catgggcgtt     720
tccacacgtg aactttcaat gatggtctat gaggcaagga acgccggggc agcaggttca     780
aagatcacag gagccggcgg cggcgggagc ataatagccc actgcccggg atgtgtggat     840
gatgttgtca cggcccttaa caggaactgg aaagccatga gggcagagtt ttcggttaag     900
ggactcatct aa                                                         912
```

<210> SEQ ID NO 27
<211> LENGTH: 855
<212> TYPE: DNA
<213> ORGANISM: Archaeoglobus fulgidus

<400> SEQUENCE: 27

```
tcactcttca attctgacac cctccttttc gggctcgact atgaagctcc ctttcggctt      60
ctctcccttg aacaggccga atatacaccc ccaccaccc gctccagtta ttttcgcatt      120
caaacccatc ctttcgagct ctgcaatggt tctgtcgatt tcgggattgc tcaccccctat    180
cgccctcaga agcgactggt ttatggctat gagctcctca agtctttcag cgctgccaac    240
atcgctcgcc tcaagggaga ttgcgtcgat agcgtcaaat attttatcca caacctcagg    300
atgcctctct ctcagctcag caacttttgc gaccatctca gccgttgacc tgctgccaaa    360
gttgataacg aagaacttga acggcatctc gacctttcta cgctcaggga aaagccacga    420
acctccaaag gtggatatga acgggtctat tccgctcgcc cttccctgaa cgtcaatctc    480
aacctgcttc gccatctgga agatggcctc tttatccata tccccatcga actctgcatt    540
cagagcagct attgtggcaa caatcaccgc cgcagagctg cccagcccag agccaatcgg    600
tatttcgctc tcaatctcaa tttcagcacc cggaatattt ctaagctccc caaacctctt    660
aacagcctgc acgacgtagg gatgcctttg atagtccagc ccgctctctc ctaacgaaga    720
cctaatcaga aacctgtcag attttctcac cgacactctg catctaaggt taatcgctga    780
caccaccgca tgcctaccgt aaaccaccgc atgctcgccg aacagaatta tctttccggg    840
tgctgatgca atcat                                                      855
```

<210> SEQ ID NO 28

<211> LENGTH: 939
<212> TYPE: DNA
<213> ORGANISM: Methanococcus jannaschii

<400> SEQUENCE: 28

```
atgataattg aaacaccatc aaaagttata ctattcggag agcatgcagt tgtttatggt      60
tatagagcta tatctatggc tattgattta acatcaacca tagaaataaa agaaacacaa     120
gaagatgaga taattttaaa cctaaatgac ttgaataaaa gcttaggttt gaacttaaat     180
gagataaaaa atatcaatcc aaataacttt ggagatttta atactgcct  ctgtgcaatt     240
aaaaacactt tagattattt aaatatagag ccaaaaactg ttttaaaaat taacattagc     300
tcaaaaattc aataagttg  tggtttggga agctctgcct caataacaat tggaactata     360
aaagctgtaa gtggatttta taataaagag cttaaagatg atgagattgc aaaacttgga     420
tatatggttg agaaagaaat ccaaggtaag gcaagcatta cagacacttc gacaataacg     480
tataaaggta tcttagaaat aaaaaacaac aagtttagaa aaattaaagg agagtttgaa     540
gaattttaa  aaaattgcaa gttttaatt  gtttatgctg aaaaaaggaa gaaaaaaact     600
gctgagttag ttaatgaagt tgccaagatt gaaaataaag atgagatatt taaagagata     660
gacaaagtta ttgatgaagc tttaaaaatc aaaaataaag aagattttgg gaaattgatg     720
actaaaaacc acgagttgtt aaaaaagcta aatatctcaa caccaaaact tgatagaatt     780
gtagatattg ggaatagatt tggttttggg gcaaaattaa ctggagctgg aggggagga    840
tgtgtaataa tcttagttaa tgaagaaaaa gagaaagagc ttttaaaaga actaaataaa     900
gaagatgtaa ggattttaa  ctgcagaatg atgaattaa                            939
```

<210> SEQ ID NO 29
<211> LENGTH: 975
<212> TYPE: DNA
<213> ORGANISM: Aeropyrum pernix

<400> SEQUENCE: 29

```
atgaggaggg ctgctagggc gtctgccccg gggaaagtta taatcgttgg agaacacttc      60
gtcgtcagag gctccctggc gatagtggcg gccataggca gaaggctccg cgtcaccgtg     120
agaagcgggg gcaaggggat tgtgcttgag agcagcatgc taggccgcca cagcgccccg     180
ctaccaggcc agggtgcagc ggctaaggta agccccgtcc tcgagccgta catagcagtg     240
ttgagaagtc tggctgcaag gggctatagc gtagtgcccc atacaatatt ggtggagagc     300
ggcatacccc ctagggcagg tctcggtagc agcgccgcca gcatggtagc ctatgctcta     360
tcatactcgg ccatgcatgg tgaccccctc tcggctgagg acctctacag tgttgctatg     420
gagggcgaga agatagcgca tggtaagccg agcggtgttg acgtaaccat agccgttagg     480
gggggagtcc tggcttacag gaggggcgag aacccggtgg atataaggcc ggggcttaca     540
ggtgtcactc tgcttgttgc cgacacgggt gtcgagaggc gtactaggga tgttgtcgag     600
catgttctct ccattgcgga cgccttggga gaggcatcga cctacatata tagggcggca     660
gacttgatag cgagagaagc cctccatgcg atagaaaagg gagacgccga gaggctaggt     720
cttataatga atgcagccca gggccttctc tcatctcttg gggcgtcgtc actagaaata     780
gaaacactag tatatcggat gaggagtgcc ggggccctgg gtgcaaagct aacgggagct     840
ggatgggggg gctgtgtgat agggcttttc aaggagggtg aggtcgaacg ggggctagag     900
tctgtggtag agagttcaag ccaggctttc accgcgtcaa tagcagagga gggtgctaga     960
ctcgaggagt tctag                                                      975
```

<210> SEQ ID NO 30
<211> LENGTH: 432
<212> TYPE: PRT
<213> ORGANISM: Phaffia rhodozyma ATCC 96594

<400> SEQUENCE: 30

```
Lys Glu Glu Ile Leu Val Ser Ala Pro Gly Lys Val Ile Leu Phe Gly
1               5                   10                  15

Glu His Ala Val Gly His Gly Val Thr Gly Ile Ala Ala Ser Val Asp
            20                  25                  30

Leu Arg Cys Tyr Ala Leu Leu Ser Pro Thr Ala Thr Thr Thr Thr Ser
        35                  40                  45

Ser Ser Leu Ser Ser Thr Asn Ile Thr Ile Ser Leu Thr Asp Leu Asn
    50                  55                  60

Phe Thr Gln Ser Trp Pro Val Asp Ser Leu Pro Trp Ser Leu Ala Pro
65                  70                  75                  80

Asp Trp Thr Glu Ala Ser Ile Pro Glu Ser Leu Cys Pro Thr Leu Leu
                85                  90                  95

Ala Glu Ile Glu Arg Ile Ala Gly Gln Gly Gly Asn Gly Gly Glu Arg
            100                 105                 110

Glu Lys Val Ala Thr Met Ala Phe Leu Tyr Leu Leu Val Leu Leu Ser
        115                 120                 125

Lys Gly Lys Pro Ser Glu Pro Phe Glu Leu Thr Ala Arg Ser Ala Leu
    130                 135                 140

Pro Met Gly Ala Gly Leu Gly Ser Ser Ala Ala Leu Ser Thr Ser Leu
145                 150                 155                 160

Ala Leu Val Phe Leu Leu His Phe Ser His Leu Ser Pro Thr Thr Thr
                165                 170                 175

Gly Arg Glu Ser Thr Ile Pro Thr Ala Asp Thr Glu Val Ile Asp Lys
            180                 185                 190

Trp Ala Phe Leu Ala Glu Lys Val Ile His Gly Asn Pro Ser Gly Ile
        195                 200                 205

Asp Asn Ala Val Ser Thr Arg Gly Gly Ala Val Ala Phe Lys Arg Lys
    210                 215                 220

Ile Glu Gly Lys Gln Glu Gly Gly Met Glu Ala Ile Lys Ser Phe Thr
225                 230                 235                 240

Ser Ile Arg Phe Leu Ile Thr Asp Ser Arg Ile Gly Arg Asp Thr Arg
                245                 250                 255

Ser Leu Val Ala Gly Val Asn Ala Arg Leu Ile Gln Glu Pro Glu Val
            260                 265                 270

Ile Val Pro Leu Leu Glu Ala Ile Gln Gln Ile Ala Asp Glu Ala Ile
        275                 280                 285

Arg Cys Leu Lys Asp Ser Glu Met Glu Arg Ala Val Met Ile Asp Arg
    290                 295                 300

Leu Gln Asn Leu Val Ser Glu Asn His Ala His Leu Ala Ala Leu Gly
305                 310                 315                 320

Val Ser His Pro Ser Leu Glu Glu Ile Ile Arg Ile Gly Ala Asp Lys
                325                 330                 335

Pro Phe Glu Leu Arg Thr Lys Leu Thr Gly Ala Gly Gly Gly Gly Cys
            340                 345                 350

Ala Val Thr Leu Val Pro Asp Asp Phe Ser Thr Glu Thr Leu Gln Ala
        355                 360                 365

Leu Met Glu Thr Leu Val Gln Ser Ser Phe Ala Pro Tyr Ile Ala Arg
```

```
            370             375             380
Val Gly Gly Ser Gly Val Gly Phe Leu Ser Ser Thr Lys Ala Asp Pro
385             390                 395                 400

Glu Asp Gly Glu Asn Arg Leu Lys Asp Gly Leu Val Gly Thr Glu Ile
            405                 410                 415

Asp Glu Leu Asp Arg Trp Ala Leu Lys Thr Gly Arg Trp Ser Phe Ala
            420                 425                 430
```

<210> SEQ ID NO 31
<211> LENGTH: 4135
<212> TYPE: DNA
<213> ORGANISM: Phaffia rhodozyma ATCC96594

<400> SEQUENCE: 31

```
actgactcgg ctaccggaaa atatctttc aggacgcctt gatcgttttg acaacacca      60
tgatgtcacc atatcttcag cggccgttgg agctaggagt agacattgta tacgactctg    120
gaacaaagta tttgagtgga caccacgatc tcatggctgg tgtgattact actcgtactg    180
aggagattgg gaaggttcgt gcttgcttgc tttgaatgtc gtgcctaaag ccattgccat    240
aagacagagt ctgatctatg tcgtttgcct acaacagaga atggcctggt tcccaaatgc    300
tatgggaaat gcattgtctc cgttcgactc gttccttctt ctccgaggac tcaaaacact    360
tcctctccga ctggacaagc agcaggcctc atctcacctg atcgcctcgt acttacacac    420
cctcggcttt cttgttcact accccggtct gccttctgac cctgggtacg aacttcataa    480
ctctcaggcg agtggtgcag gtgccgtcat gagctttgag accggagata tcgcgttgag    540
tgaggccatc gtgggcggaa cccgagtttg gggaatcagt gtcagtttcg agccgtgaa     600
cagtttgatc agcatgcctt gtctaatgag gttagttctt atgccttctt ttcgcgcctt    660
ctaaaatttc tggctgacta attgggtcgg tctttccgtt cttgcatttc agtcacgcat    720
ctattcctgc tcaccttcga gccgagcgag gtctccccga acatctgatt cgactgtgtg    780
tcggtattga ggaccctcac gatttgcttg atgatttgga ggcctctctt gtgaacgctg    840
gcgcaatccg atcagtctct acctcagatt catcccgacc gctcactcct cctgcctctg    900
attctgcctc ggacattcac tccaactggg ccgtcgaccg agccagacag ttcgagcgtg    960
ttaggccttc taactcgaca gccggcgtcg aaggacagct tgccgaactc aatgtagacg   1020
atgcagccag acttgcgggc gatgagagcc aaaaagaaga aattcttgtc agtgcaccgg   1080
gaaaggtcat tctgttcggc gaacatgctg taggccatgg tgttgtgagt gagaaatgaa   1140
agctttatgc tctcattgca tcttaacttt tcctcgcctt ttttgttctc ttcatcccgt   1200
cttgattgta gggatgcccc cctttgcccc tttcccttc ttgcatctgt ctatatttcc    1260
ttatacattt cgctcttaag agcgtctagt tgtaccttat aacaaccttt ggttttagca   1320
tcctttgatt attcatttct ctcatccttc ggtcagaggc tttcggccat ctttacgtct   1380
gattagattg taatagcaag aactatcttg ctaagccttt tctcttcctc ttcctcctat   1440
ataaatcgaa ttcactttcg gacatgttta ttttggggaa atcatcaagg ggtgggggc    1500
caatcccgac actaattttc tgctcacgtc aaaactcagc gttcagaatc agtcactgac   1560
cctgatacgt gtctctatgt gtgtgggtgt acgtgcgaat tgtgactcga cgttctacgc   1620
ttaaaaacag accgggatcg ctgcttccgt tgatcttcga tgctacgctc ttctctcacc   1680
cactgctacg acaacaacat catcgtcgtt atcgtctaca acattaccca tctccctaac   1740
ggacctgaac tttacgcagt cttggcctgt tgattctctt ccttggtcac ttgcgcctga   1800
```

```
ctggactgag gcgtctattc cagaatctct ctgcccgaca ttgctcgccg aaatcgaaag    1860
gatcgctggt caaggtggaa acggaggaga aagggagaag gtggcaacca tggcattctt    1920
gtatttgttg gtgctattga gcaaagggaa gccaaggtag gttttttctg tctcttcttt    1980
ttgcctataa agactcttaa ctgacggaga aagtgttggg tttcttcctt cggggggttca   2040 atcaattaaa gtgagccgtt cgagttgacg gctcgatctg cgcttccgat gggagctggt    2100
ctgggttcat ccgccgctct atcgacctct cttgccctag tctttcttct ccacttttct    2160
cacctcagtc caacgacgac tggcagagaa tcaacaatcc cgacggccga cacagaagta    2220
attgacaaat gggcgttctt agctgaaaaa gtcatccatg gaaatccgag tgggattgat    2280
aacgcggtca gtacgagagg aggcgctgtt gctttcaaaa gaaagattga gggaaaacag    2340
gaaggtggaa tggaagcgat caagaggtac gcagacacgg tgcttcatat gccatactcc    2400
agtctgattg acccatgatg aacgtctttc tacatttcga atatagcttc acatccattc    2460
gattcctcat cacagattct cgtatcgaaa gggatacaag atctctcgtt gcaggagtga    2520
atgctcgact gattcaggag ccagaggtga tcgtcccttt gttggaagcg attcagcaga    2580
ttgccgatga ggctattcga tgcttgaaag attcagagat ggaacgtgct gtcatgatcg    2640
atcgacttca agttagttct tgttcctttc aagactcttt gtgacattgt gtcttatcca    2700
tttcatcttc tttttttcttc cttcttctgc agaacttggt ctccgagaac cacgcacacc    2760
tagcagcact tggcgtgtcc cacccatccc tcgaagagat tatccggatc ggtgctgata    2820
agcctttcga gcttcgaaca aagttgacag gcgccggtgg aggtggttgc gctgtaaccc    2880
tggtgcccga tggtaaagtc tctccttttc tcttccgtcc aagcgacaca tctgaccgat    2940
gcgcatcctg tacttttggt caaccagact tctcgactga aacccttcaa gctcttatgg    3000
agacgctcgt tcaatcatcg ttcgcccctt atattgcccg agtgggtggt tcaggcgtcg    3060
gattcctttc atcaactaag gccgatccgg aagatgggga aacagactt aaagatgggc    3120 tggtgggaac ggagattgat gagctagaca gatgggcttt gaaaacgggt cgttggtctt    3180
ttgcttgaac gaaagatagg aaacggtgat tagggtacag atcctttgct gtcattttta    3240
caaaacactt tcttatgtct tcatgactca acgtatgccc tcatctctat ccatagacag    3300
cacggtacct ctcaggtttc aatacgtaag cgttcatcga caaaacatgc ggcacacgaa    3360
aacgagtgga tataagggag aagagagata ttagagcgaa aagagaaga gtgagagagg    3420 aaaaaaataa ccgagaacaa cttattccgg tttgttagaa tcgaagatcg agaaatatga    3480
agtacatagt ataaagtaaa gaagagaggt ttacctcaga ggtgtgtacg aaggtgagga    3540
caggtaagag gaataattga ctatcgaaaa aagagaactc aacagaagca ctgggataaa    3600
gcctagaatg taagtctcat cggtccgcga tgaaagagaa attgaaggaa gaaaaagccc    3660
ccagtaaaca atccaaccaa cctcttggac gattgcgaaa cacacacacg cacgcggaca    3720
tatttcgtac acaaggacgg gacattcttt ttttatatcc gggtggggag agagagggtt    3780
atagaggatg aatagcaagg ttgatgtttt gtaaaaggtt gcagaaaaag gaaagtgaga    3840
gtaggaacat gcattaaaaa cctgcccaaa gcgatttata tcgttcttct gttttcactt    3900
ctttccgggc gctttcttag accgcggtgg tgaagggtta ctcctgccaa ctagaagaag    3960
caacatgagt caaggattag atcatcacgt gtctcatttg acgggttgaa agatatattt    4020
agatactaac tgcttcccac gccgactgaa aagatgaatt gaatcatgtc gagtggcaac    4080
gaacgaaaga acaaatagta agaatgaatt actagaaaag acagaatgac tagaa          4135
```

<210> SEQ ID NO 32
<211> LENGTH: 1164
<212> TYPE: DNA
<213> ORGANISM: Artificial sequence
<220> FEATURE:
<223> OTHER INFORMATION: Paracoccus zeaxanthinifaciens I17T

<400> SEQUENCE: 32

```
atgagaggat cgcatcacca tcaccatcac tcgaccggca ggcctgaagc aggcgcccat    60
gccccgggca agctgaccct gtccggggaa cattccgtgc tctatggtgc gcccgcgctt   120
gccatggcca tcgcccgcta taccgaggtg tggttcacgc cgcttggcat ggcgaggggg   180
atacgcacga cattcgccaa tctctcgggc ggggcgacct attcgctgaa gctgctgtcg   240
gggttcaagt cgcggctgga ccgccggttc gagcagttcc tgaacggcga cctaaaggtg   300
cacaaggtcc tgacccatcc cgacgatctg gcggtctatg cgctggcgtc gcttctgcac   360
gacaagccgc cggggaccgc cgcgatgccg ggcatcggcg cgatgcacca cctgccgcga   420
ccgggtgagc tgggcagccg gacggagctg cccatcggcg cgggcatggg gtcgtctgcg   480
gccatcgtcg cggccaccac ggtcctgttc gagacgctgc tggaccggcc caagacgccc   540
gaacagcgct tcgaccgcgt ccgcttctgc gagcggttga agcacggcaa ggccggtccc   600
atcgacgcgg ccagcgtcgt gcgcggcggg cttgtccgcg tgggcgggaa cgggccgggt   660
tcgatcagca gcttcgattt gcccgaggat cacgaccttg tcgcgggacg cggctggtac   720
tgggtactgc acgggcgccc cgtcagcggg accggcgaat gcgtcagcgc ggtcgcggcg   780
gcgcatggtc gcgatgcggc gctgtgggac gccttcgcag tctgcacccg cgcgttggag   840
gccgcgctgc tgtctggggg cagccccgac gccgccatca ccgagaacca gcgcctgctg   900
gaacgcatcg gcgtcgtgcc ggcagcgacg caggccctcg tggcccagat cgaggaggcg   960
ggtggcgcgg ccaagatctg cggcgcaggt tccgtgcggg gcgatcacgg cggggcggtc  1020
ctcgtgcgga ttgacgacgc gcaggcgatg gcttcggtca tggcgcgcca tcccgacctc  1080
gactgggcgc ccctgcgcat gtcgcgcacg ggggcggcac ccggccccgc gccgcgtgcg  1140
caaccgctgc cggggcaggg ctga                                        1164
```

<210> SEQ ID NO 33
<211> LENGTH: 1164
<212> TYPE: DNA
<213> ORGANISM: Artificial sequence
<220> FEATURE:
<223> OTHER INFORMATION: Paracoccus zeaxanthinifaciens I17T, G47D, K93E, P132S

<400> SEQUENCE: 33

```
atgagaggat cgcatcacca tcaccatcac tcgaccggca ggcctgaagc aggcgcccat    60
gccccgggca agctgaccct gtccggggaa cattccgtgc tctatggtgc gcccgcgctt   120
gccatggcca tcgcccgcta taccgaggtg tggttcacgc cgcttgacat ggcgaggggg   180
atacgcacga cattcgccaa tctctcgggc ggggcgacct attcgctgaa gctgctgtcg   240
gggttcaagt cgcggctgga ccgccggttc gagcagttcc tgaacggcga cctaaaggtg   300
cacgaggtcc tgacccatcc cgacgatctg gcggtctatg cgctggcgtc gcttctgcac   360
gacaagccgc cggggaccgc cgcgatgccg ggcatcggcg cgatgcacca cctgccgcga   420
tccggtgagc tgggcagccg gacggagctg cccatcggcg cgggcatggg gtcgtctgcg   480
gccatcgtcg cggccaccac ggtcctgttc gagacgctgc tggaccggcc caagacgccc   540
gaacagcgct tcgaccgcgt ccgcttctgc gagcggttga agcacggcaa ggccggtccc   600
```

```
atcgacgcgg  ccagcgtcgt  gcgcggcggg  cttgtccgcg  tgggcgggaa  cgggccgggt      660
tcgatcagca  gcttcgattt  gcccgaggat  cacgaccttg  tcgcgggacg  cggctggtac      720
tgggtactgc  acgggcgccc  cgtcagcggg  accggcgaat  gcgtcagcgc  ggtcgcggcg      780
gcgcatggtc  gcgatgcggc  gctgtgggac  gccttcgcag  tctgcacccg  cgcgttggag      840
gccgcgctgc  tgtctggggg  cagccccgac  gccgccatca  ccgagaacca  gcgcctgctg      900
gaacgcatcg  gcgtcgtgcc  ggcagcgacg  caggccctcg  tggcccagat  cgaggaggcg      960
ggtggcgcgg  ccaagatctg  cggcgcaggt  tccgtgcggg  gcgatcacgg  cggggcggtc     1020
ctcgtgcgga  ttgacgacgc  gcaggcgatg  gcttcggtca  tggcgcgcca  tcccgacctc     1080
gactgggcgc  ccctgcgcat  gtcgcgcacg  ggggcggcac  ccggccccgc  gccgcgtgcg     1140
caaccgctgc  cggggcaggg  ctga                                              1164
```